(12) United States Patent
Tran et al.

(10) Patent No.: US 10,176,642 B2
(45) Date of Patent: Jan. 8, 2019

(54) SYSTEMS AND METHODS FOR COMPUTER ASSISTED OPERATION

(71) Applicants: Bao Tran, Saratoga, CA (US); Ha Tran, Saratoga, CA (US)

(72) Inventors: Bao Tran, Saratoga, CA (US); Ha Tran, Saratoga, CA (US)

(*) Notice: Subject to any disclaimer, the term of this patent is extended or adjusted under 35 U.S.C. 154(b) by 0 days.

(21) Appl. No.: 15/450,710

(22) Filed: Mar. 6, 2017

(65) Prior Publication Data

US 2017/0323481 A1    Nov. 9, 2017

Related U.S. Application Data

(63) Continuation-in-part of application No. 15/148,739, filed on May 6, 2016.

(60) Provisional application No. 62/193,584, filed on Jul. 17, 2015.

(51) Int. Cl.
| | |
|---|---|
| G06F 3/01 | (2006.01) |
| G06K 9/00 | (2006.01) |
| G06K 9/46 | (2006.01) |
| G06F 19/00 | (2018.01) |
| G06T 19/00 | (2011.01) |
| G16H 50/50 | (2018.01) |
| H04N 5/232 | (2006.01) |

(52) U.S. Cl.
CPC ............ *G06T 19/006* (2013.01); *G06F 3/013* (2013.01); *G06F 3/017* (2013.01); *G06F 19/00* (2013.01); *G06K 9/00771* (2013.01); *G06K 9/4671* (2013.01); *G16H 50/50* (2018.01); *H04N 5/23212* (2013.01); *H04N 5/23219* (2013.01); *G06K 2209/17* (2013.01)

(58) Field of Classification Search
CPC ... G06T 19/006; G06T 2215/16; G06T 11/60; G06T 15/50; G06T 2210/21; G06T 7/90; G06Q 30/06; G06Q 30/0643; G06Q 30/0601; G06Q 30/0623
USPC .......................................... 348/53; 345/633
See application file for complete search history.

(56) References Cited

U.S. PATENT DOCUMENTS

| | | |
|---|---|---|
| 6,155,490 A | 12/2000 | Ackley |
| 6,452,088 B1 | 9/2002 | Schmidt |
| 7,762,945 B2 | 7/2010 | Blumenthal |
| 8,096,654 B2 | 1/2012 | Amirparviz |
| 8,265,949 B2 | 9/2012 | Haddad |
| D701,206 S | 3/2014 | Luckey |
| 8,711,495 B2 | 4/2014 | Topliss |
| 8,947,456 B2 | 2/2015 | Chen |
| 8,950,867 B2 | 2/2015 | Macnamara |
| 9,552,674 B1 * | 1/2017 | Jayadevaprakash et al. ............... G06T 19/006 |
| 2004/0132439 A1 | 7/2004 | Tyagi |
| 2008/0062338 A1 | 3/2008 | Herzog |

(Continued)

*Primary Examiner* — Deirdre L Beasley
(74) *Attorney, Agent, or Firm* — Tran & Associates

(57) ABSTRACT

An augmented reality method includes selecting an image of an object to be installed; converting the image into a 3D model; capturing a view of an environment and selecting a place to insert the 3D model; overlaying the 3D model with the view of the environment in a mashed-up and aligned manner wherein the 3D model view is displayed contemporaneously and contiguously to form an augmented reality view; and enabling user interaction with the displayed 3D model view to update the 3D model of the environment in the 3D modeling system.

20 Claims, 27 Drawing Sheets

(56) References Cited

U.S. PATENT DOCUMENTS

| | | | |
|---|---|---|---|
| 2012/0038629 A1* | 2/2012 | Brown | A61B 3/113 345/419 |
| 2012/0193806 A1 | 8/2012 | Orbach | |
| 2012/0231424 A1* | 9/2012 | Calman | G09B 25/04 434/72 |
| 2013/0044042 A1 | 2/2013 | Olsson | |
| 2013/0125027 A1 | 5/2013 | Abovitz | |
| 2014/0002472 A1 | 1/2014 | Sobeski | |
| 2014/0003762 A1 | 1/2014 | Macnamara | |
| 2014/0071539 A1 | 3/2014 | Gao | |
| 2014/0222462 A1 | 8/2014 | Shakil | |
| 2014/0267420 A1 | 9/2014 | Schowengerdt | |
| 2014/0285522 A1* | 9/2014 | Kim | G06T 19/006 345/633 |
| 2014/0306866 A1 | 10/2014 | Miller | |
| 2014/0347491 A1 | 11/2014 | Connor | |
| 2014/0368373 A1* | 12/2014 | Crain | G01S 5/02 342/5 |
| 2015/0016777 A1 | 1/2015 | Abovitz | |
| 2015/0116356 A1* | 4/2015 | Alon | G01C 21/206 345/633 |
| 2015/0148650 A1 | 5/2015 | Pugh | |
| 2015/0161821 A1 | 6/2015 | Mazula | |
| 2015/0235610 A1* | 8/2015 | Miller | G09G 5/006 345/633 |
| 2015/0325047 A1* | 11/2015 | Conner | G06T 19/006 345/633 |
| 2016/0026253 A1* | 1/2016 | Bradski | G02B 27/225 345/8 |
| 2016/0033770 A1* | 2/2016 | Fujimaki et al. | G06T 19/006 345/8 |
| 2016/0140868 A1* | 5/2016 | Lovett | G09B 19/0053 434/118 |
| 2016/0253745 A1* | 9/2016 | Lee | G06Q 30/06 705/27.2 |
| 2016/0379408 A1* | 12/2016 | Wright | G06T 19/006 345/633 |
| 2017/0061693 A1* | 3/2017 | Kohler | G06T 19/006 |
| 2017/0064279 A1* | 3/2017 | Chien | H04N 13/0018 |
| 2017/0091607 A1* | 3/2017 | Emeis | H04W 4/023 |
| 2017/0161824 A1* | 6/2017 | Ramos | G06Q 30/0643 |
| 2017/0169610 A1* | 6/2017 | King | G06T 19/006 |
| 2017/0323449 A1* | 11/2017 | Aonuma | G06T 7/20 |

\* cited by examiner

FIG. 1F
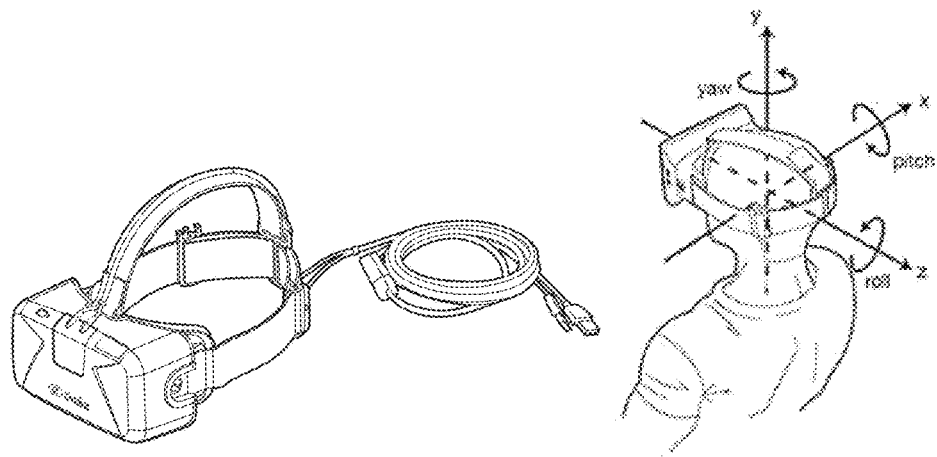
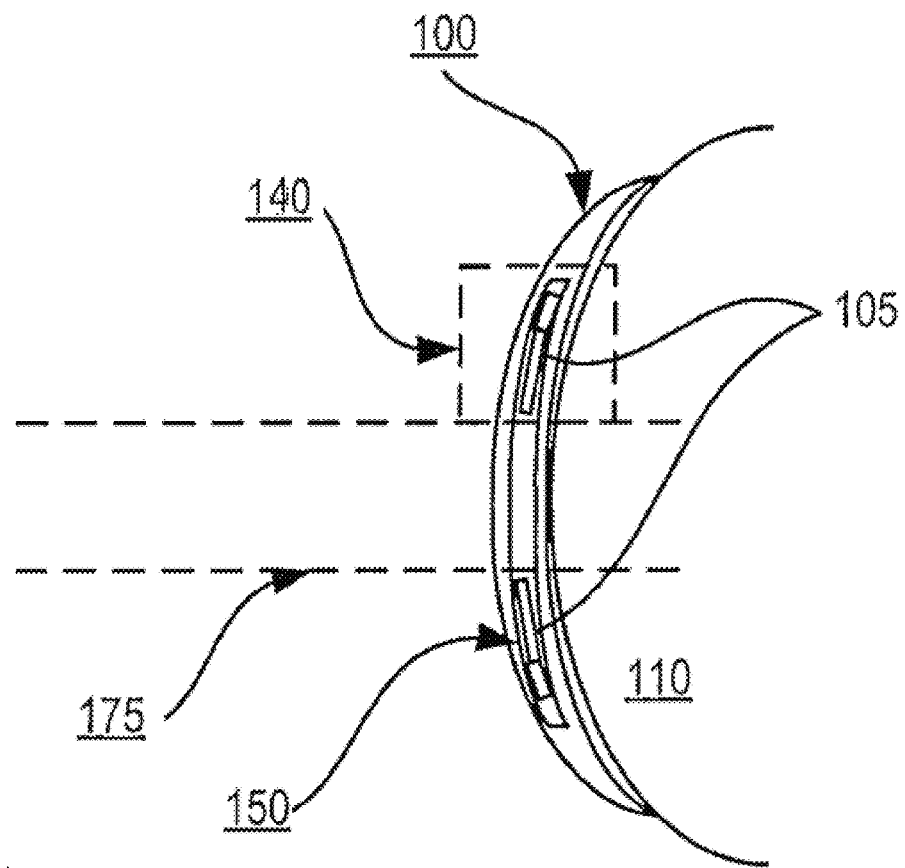
FIG. 2A

SYSTEMS AND METHODS FOR COMPUTER ASSISTED OPERATION

BACKGROUND

The present invention relates to computer-aided reality systems.

Modern "virtual reality" apparatus typically include video and audio signal generators that provide signals to a headset in accordance with instructions received from a controller. The headset projects a near field image inches away from the viewer, typically completely occupying the field of the vision of the viewer's eyes. Most such virtual reality systems alter the view presented to the viewer in response to the position of the viewer's head, as sensed by the headset, such that the view changes in much the same manner that a far field image received by the human eye would vary. Other system have presented an image to a viewer by scanning the viewer's eye or eyes with a modulated beam of light. Such systems directly present the image to the viewer's retinas, thereby advantageously obviating the need for either far field or near field projection screens.

U.S. Pat. No. 6,454,411 discloses an apparatus for directly projecting an image onto a retina includes an optical source for generating a light beam to be focused on a retina. A projection device sweeps the light beam along the retina in an ellipsoidal pattern such that a higher spatial concentration of light pixels impinge a central portion of the retina than a peripheral portion thereof. A controller is coupled to the optical source and the projection device for modulating the light beam such that a higher temporal concentration of light pixels impinge a central portion of the retina than a peripheral portion thereof.

SUMMARY

Systems and methods are presented for augmented reality (AR) or virtual reality (VR).

In one aspect, an augmented reality method includes selecting an image of an object to be installed; converting the image into a 3D model; capturing a view of a environment and selecting a place to insert the 3D model; overlaying the 3D model with the view of the environment in a mashed-up and aligned manner wherein the 3D model view is displayed contemporaneously and contiguously to form an augmented reality view; and enabling user interaction with the displayed 3D model view to update the 3D model of the environment in the 3D modeling system.

Advantages of the system may include one or more of the following. With Augmented Reality apps, the user can see a 360-degree view of products and a 3D representation in the desired space of the consumer's home. The technology can help consumers and reduce friction in the purchasing process. Online retailers can offer a printable marker to launch a similar experience and provide consumers with convenience. Augmented Reality offers a host of shopping options for catalog and online retailers, providing an effective visualization of products and a seamless path to purchase. Augmented Reality can be used to give customers more reasons to visit a brick-and-mortar store. The system provides consumers with the opportunity to interact with products and receive rewards. With an Augmented Reality retail display, a company's sales team can demo the display with ease and share multiple displays at one time. That increases the efficiency of the sales team and reduces costs. AR can create the tools to equip your sales team with the power to reach and exceed sales goals. Using 3D and AR/VR environments as part of a training methodology allows students or workforce to experience an entirely new side of training. The technology breathes life back into traditional computer based learning and re-awakens the enthusiasm in users who are used to AR/VR technology in other circles outside of training. The system applies e-learning to impart the theoretical understanding and knowledge then virtual reality scenarios to test the information learned in a life-like situation to give users the complete package. The VR enables a client to view the competency of the learners, see the decisions they make and how they then react to the consequences. VR e-learning can be used to simulate the way equipment responds; emulate the way machinery works or to replicate soft skills such as human actions and behavior. AR/VR simulations use basic principles of learning to produce fun, compelling and memorable end results. By modeling equipment in AR/VR, possibly down to the last detail a company could distribute a training program to all employees or learners that will allow them to interact with the AR/VR, follow best practice procedures or carry out fault finding scenarios, all without having to access (and possibly damage) the real item. Complicated pieces of equipment, processes or systems can be recreated using a number of techniques. This form of e-learning allows users to learn about mechanisms and processes that would be physically or logistically difficult to do so in other conditions. Highly interactive, VR environments can be used to help teach how to properly handle dangerous conditions. By creating an environment which simulates a potentially harmful real-life situation or replicating a piece of dangerous equipment, the interactive scenarios remove these concerns and help the user gain a knowledge and understanding of the subject matter without being put into a costly or harmful environment. The system can be used for dating to show matching people and how to approach them. The system can be used in medical applications. The system can also be used in manufacturing designs. The system can provide augmented bionic vision, among others. Other advantages exist as well.

BRIEF DESCRIPTION OF THE DRAWINGS

FIG. 1F shows one virtual reality (VR) implementation using a lens;

FIG. 2A shows a representation of a region of the retinal vascularization of an eye;

FIG. 18A shows an exemplary AR surgical system, while

DESCRIPTION

Figure 1A:
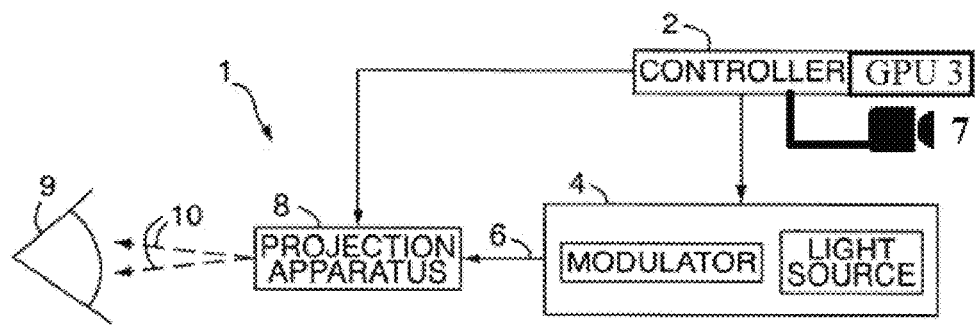
FIG. 1A illustrates a system 1 for projecting an image onto a human retina and for scanning the eye for medical application such as glucose sensing or for emotion sensing when blood vessels dilate.

FIG. 1A illustrates a system 1 for projecting an image onto a human retina and for scanning the eye. Using waveguides, 3D objects can be viewed from the projections. Data from the scan can be used for medical application such as glucose sensing or for emotion sensing when blood vessels dilate. The system 1 can be used in virtual reality applications, augmented reality applications, or a combination thereof.

The system 1 includes a controller 2 with graphical processing units (GPUs) 3 which generates signals in accordance with processes detailed hereinafter for presentation to a modulated optical source 4, which provides a modulated optical beam 6 to a projection apparatus 8. One or more cameras 7 can capture video images that can be projected by the projection apparatus 8 to stimulate the neurons on the eye of a blind person to enable the blind person to see at least a part of the video. The one or more cameras 7 can aim at the retina or can aim in the viewing direction of a user, depending on the application. The projection apparatus scans an image onto the retina of the eye 9 of a viewer, as indicated by reference numeral 10. The modulated light source includes a laser or other light source, which can be used for generation of an optical image. Preferably, the light source is a laser. The modulated light source can also include a discrete optical modulator, which is addressable and receives control signals from the controller 2. The optical modulator 4 can be of a known type, and is capable of modulating an optical beam with sufficient bandwidth to allow for presentation of the image to the viewer. Those skilled in the art will note that in certain embodiments, the light source may be modulated directly, without the inclusion of the discrete optical modulator. The on-chip laser light source emits a laser light beam that travels through the lens and a partially-silvered mirror. The laser light beam is reflected off a MEMS scanning mirror that is oscillating to provide a scan. The MEMS scanning mirror can be a resonate transducer, as known in the art. This device can be made to resonate at a desired frequency, either in one direction or in two directions. The resonate transducer may use a mechanically free beam of polysilicon and may also be positioned on thin membranes or diaphragms, cantilevers, and other flexure type mechanisms. The resonant frequency may be induced electronically by the scanner electronics, as known in the art. The MEMS scanning mirror has a mirrored surface and resonates at a controlled frequency in the horizontal and vertical direction, can produce a rastering scan pattern when a laser light source is reflected from its surface. The MEMS scanning mirror may be fabricated using integrated circuit techniques such as surface micromachining Alternative fabrication techniques also exist such as bulk micromachining, LIGA (a German acronym referring to lithography, electroforming, and injection molding), or LIGA-like machining, as known in the art. Additional fabrication techniques such as chemical-mechanical polishing may be performed to improve the optical quality of the mirrored surface by reducing the surface roughness.

The light emitting spots are produced by microns-sized diodes/lasers pumping phosphors located above the diodes/lasers. The individual spots of light used to make an image can all be of the same color (monochromatic) or of different colors. In the multiple color operation, the present invention uses a single or monochromatic pump source rather than discrete diode/laser sources of different colors. The lasers are fabricated in a two dimensional ("2D") array format with established semiconductor processing techniques and practices. The 2D laser arrays are then integrated with nonlinear optical processes such as up-conversion (anti-Stokes process) in order to obtain multiple color outputs. Using photons with nonlinear up-conversion materials to obtain visible light output from a display device provides an advantage toward miniaturization of the present display. Using miniature (microns-sized) light emitting structures, such as surface emitting laser diodes, further allows for the miniaturization of the entire system concept illustrated in FIG. 1A to a much smaller system or package. The system uses two-dimensional arrays (m×n), of light emitting elements (photons), to miniaturize the display system to the generic manifestation illustrated in FIG. 1A. Miniaturization is also complemented through components and materials integrations in such areas as the use and integration of micro-lens array technology and the integration of the up-conversion (phosphor) materials directly onto the surfaces of the optics themselves.

Figure 1B:
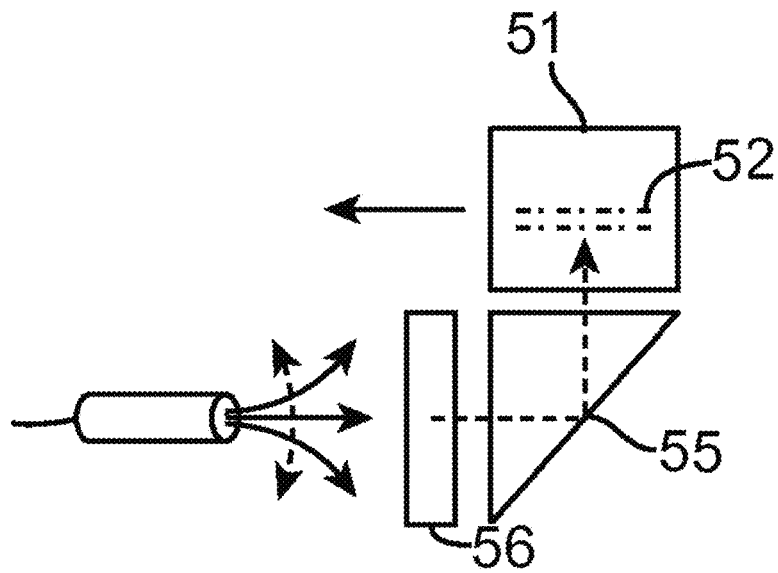
FIG. 1B shows an exemplary waveguide for delivering images.

One embodiment uses a primary waveguide includes one or more primary planar waveguides 51 (only one show in FIG. 1B), and one or more diffractive optical elements (DOEs) 52 associated with each of at least some of the primary planar waveguides 51. As best illustrated in FIG. 1B, the primary planar waveguides 51 each have at least a first end and a second end, the second end opposed to the first end along a length of the primary planar waveguide 1. The primary planar waveguides 1 each have a first face and a second face, at least the first and the second faces (forming an at least partially internally reflective optical path along at least a portion of the length 110 of the primary planar waveguide 1. The primary planar waveguide(s) 51 may take a variety of forms which provides for substantially total internal reflection (TIR) for light striking the faces at less than a defined critical angle. The planar waveguides 51 may, for example, take the form of a pane or plane of glass, fused silica, acrylic, or polycarbonate. The DOEs (illustrated by dash-dot double line) may take a large variety of forms which interrupt the TIR optical path, providing a plurality of optical paths between an interior and an exterior of the planar waveguide 51 extending along at least a portion of the length of the planar waveguide 51. The DOEs may advantageously combine the phase functions of a linear diffraction grating with that of a circular or radial symmetric lens, allowing positioning of apparent objects and focus plane for apparent objects. Such may be achieved on a frame-by-frame, subframe-by-subframe, or even pixel-by-pixel basis.

The primary planar waveguide 51 is preferably at least partially transparent. Such allows one or more viewers to view the physical objects (i.e., the real world) on a far side of the primary planar waveguide 1 relative to a vantage of the viewer. This may advantageously allow viewers to view the real world through the waveguide and simultaneously view digital imagery that is relayed to the eye(s) by the waveguide. In some implementations a plurality of waveguides systems may be incorporated into a near-to-eye display. For example, a plurality of waveguides systems may be incorporated into a head-worn, head-mounted, or helmet-mounted display—or other wearable display. In some implementations, a plurality of waveguides systems may be incorporated into a head-up display (HUD), that is not worn (e.g., an automotive HUD, avionics HUD). In such implementations, multiple viewers may look at a shared waveguide system or resulting image field. Multiple viewers may, for example see or optically perceive a digital or virtual object from different viewing perspectives that match each viewer's respective locations relative to the waveguide system.

The optical system is not limited to use of visible light, but may also employ light in other portions of the electromagnetic spectrum (e.g., infrared, ultraviolet) and/or may employ electromagnetic radiation that is outside the band of "light" (i.e., visible, UV, or IR), for example employing electromagnetic radiation or energy in the microwave or X-ray portions of the electromagnetic spectrum.

In some implementations, a scanning light display is used to couple light into a plurality of primary planar waveguides. The scanning light display can comprise a single light source that forms a single beam that is scanned over time to form an image. This scanned beam of light may be intensity-modulated to form pixels of different brightness levels. Alternatively, multiple light sources may be used to generate multiple beams of light, which are scanned either with a shared scanning element or with separate scanning elements to form imagery. These light sources may comprise different wavelengths, visible and/or non-visible, they may comprise different geometric points of origin (X, Y, or Z), they may enter the scanner(s) at different angles of incidence, and may create light that corresponds to different portions of one or more images (flat or volumetric, moving or static). The light may, for example, be scanned to form an image with a vibrating optical fiber.

The optical coupler subsystem collimates the light emerging from the scanning fiber cantilever The collimated light is reflected by mirrored surface 55 into a narrow distribution planar waveguide which contains at least one diffractive optical element (DOE). The collimated light propagates vertically along the distribution planar waveguide by total internal reflection, and in doing so repeatedly intersects with the DOE with a low diffraction efficiency. This causes a fraction (e.g., 10%) of the light to be diffracted toward an edge of the larger primary planar waveguide 51 at each point of intersection with the DOE and a fraction of the light to continue on its original trajectory down the length of the distribution planar waveguide via TIR. At each point of intersection with the DOE, additional light is diffracted toward the entrance of the primary waveguide. By dividing the incoming light into multiple outcoupled sets, the exit pupil of the light is expanded vertically by the DOE in the distribution planar waveguide. This vertically expanded light coupled out of distribution planar waveguide enters the edge of the primary planar waveguide 51. Light entering primary waveguide 51 propagates horizontally along the primary waveguide 51 via TIR. As the light intersects with DOE at multiple points as it propagates horizontally along at least a portion of the length of the primary waveguide 1 via TIR. The DOE may advantageously be designed or configured to have a phase profile that is a summation of a linear diffraction grating and a radially symmetric diffractive lens. The DOE may advantageously have a low diffraction efficiency. At each point of intersection between the propagating light and the DOE, a fraction of the light is diffracted toward the adjacent face of the primary waveguide 51 allowing the light to escape the TIR, and emerge from the face of the primary waveguide 51. The radially symmetric lens aspect of the DOE additionally imparts a focus level to the diffracted light, both shaping the light wavefront (e.g., imparting a curvature) of the individual beam as well as steering the beam at an angle that matches the designed focus level. A plurality of beams can extend geometrically to a focus point, and each beam is advantageously imparted with a convex wavefront profile with a center of radius at focus point to produce an image or virtual object at a given focal plane. The generation thereby of a multi-focal volumetric display, image or light fieldcan be done, and the system can include one or more sources of red, green, and blue laser light optically coupled into a proximal end of a single mode optical fiber.

A computer database of graphical imagery is addressed by graphics processing units (GPUs) 3 in the controller 2, such that each point (or pixel) along a sinusoidal path laser light represents an x-y pixel coordinate in the database so as to reconstruct a coherent image to a viewer and modulated to fit physiology of the eye. For example, since at a small distance from the fovea (FIG. 1C) the human eye has very poor ability to resolve sharpness or color, the system can supple the human visual cortex and brain's processing to integrate the entire visual field into a cohesive image. For example, the middle of the retina, where the minimum photon flux is presented due to the maximum velocity of the raster scan, is dimmer that the ends of the retina, which receive a maximum flux of photons. The prior art systems consequently must, at a minimum, compensate for the foregoing natural occurring phenomena to even the brightness of each of the pixels. Further, with a high concentration of image-sensing cones at the eye's fovea, the controller handles rapidly declining cone concentration as a function of distance from the fovea to the periphery of the retina. The controller drives the retinal illumination as center-weighted, which can be the inverse of the illumination. In one embodiment, illumination of just the central portion can be sufficient to create the desired image.

In the light source, a mirror oscillates sinusoidally, such as in an ellipsoidal pattern, which causes the formation of high-resolution imagery in a concentrated zone, while substantially lowering resolution in a circular field around that zone. By coupling the location of this zone of high resolution to the eye's foveal area via an eye tracking mechanism, as discussed below, a very high apparent resolution image is provided. System bandwidth requirements are reduced. Rather than a standard pixel grid in the horizontal and vertical axes, the computer can be tasked to generate pixels in an ellipsoidal sweep with a rotating central axis. This concentrates a large number of pixels into a central zone. The laser beam can be swept in sinusoidal patterns in such a manner that each sweep of the laser beam crosses at a single point in the x-y field, while the sweep precesses, so that a "frame" of image is represented by a circular field. The crossing point can be moved to any position within the field, via proper modulation of a mirror. As the laser beam is swept through a spiral pattern, it can be modulated in brightness and focus so that as the beam sweeps through the single point it is highly focused, yet much less bright. As the beam sweeps away from the point, it can grow grows brighter and less focused, so that the resultant circular field is of even apparent brightness. In this manner the beam crossing point 802 can be of extremely high resolution (since virtually every sweep passes through it) and of extremely high temporal information (since each sweep represents a small fraction of a "frame" representing one complete spiral sweep filling the entire circular field. For example, one complete spiral sweep of the circular field could occur in one-sixtieth ({fraction (1/60)}th) of a second, and consist of 525 precessing sinusoidal sweeps; thus, the field could contain the same information as a field of NTSC video. In contrast to this focus point of all sweeps, the periphery of the field drops off in clarity and information responsive, such as in direct proportion, to the distance from the focus point. At the periphery of the field, resolution is low. Thus, the visual information of a frame (or field) of an image is more concentrated at the crossing point, and more diffuse at the periphery.

One embodiment uses a plurality of cameras 7 to provide a gesture control feature. A pair of light sources can be disposed to either side of cameras and controlled byan image-analysis system. In some embodiments where the object of interest is a person's hand or body, use of infrared light can allow the motion-capture system to operate under a broad range of lighting conditions and can avoid various inconveniences or distractions that may be associated with directing visible light into the region where the person is moving. However, a particular wavelength or region of the electromagnetic spectrum is required.

It should be stressed that the foregoing arrangement is representative and not limiting. For example, lasers or other light sources can be used instead of LEDs. For laser setups, additional optics (e.g., a lens or diffuser) may be employed to widen the laser beam (and make its field of view similar to that of the cameras). Useful arrangements can also include short- and wide-angle illuminators for different ranges. Light sources are typically diffuse rather than specular point sources; for example, packaged LEDs with light-spreading encapsulation are suitable.

In operation, cameras 7 are oriented toward a region of interest in which an object of interest (in this example, a hand) and one or more background objects can be present. Light sources illuminate the region. In some embodiments, one or more of the light sources and cameras are disposed below the motion to be detected, e.g., where hand motion is to be detected, beneath the spatial region where that motion takes place. This is an optimal location because the amount of information recorded about the hand is proportional to the number of pixels it occupies in the camera images, the hand will occupy more pixels when the camera's angle with respect to the hand's "pointing direction" is as close to perpendicular as possible. Because it is uncomfortable for a user to orient his palm toward a screen, the optimal positions are either from the bottom looking up, from the top looking down (which requires a bridge) or from the screen bezel looking diagonally up or diagonally down. In scenarios looking up there is less likelihood of confusion with background objects (clutter on the user's desk, for example) and if it is directly looking up then there is little likelihood of confusion with other people out of the field of view (and also privacy is enhanced by not imaging faces). In this arrangement, image-analysis system can quickly and accurately distinguish object pixels from background pixels by applying a brightness threshold to each pixel. For example, pixel brightness in a CMOS sensor or similar device can be measured on a scale from 0.0 (dark) to 1.0 (fully saturated), with some number of gradations in between depending on the sensor design. The brightness encoded by the camera pixels scales standardly (linearly) with the luminance of the object, typically due to the deposited charge or diode voltages. In some embodiments, light sources 808, 810 are bright enough that reflected light from an object at distance rO produces a brightness level of 1.0 while an object at distance rB=2rO produces a brightness level of 0.25. Object pixels can thus be readily distinguished from background pixels based on brightness. Further, edges of the object can also be readily detected based on differences in brightness between adjacent pixels, allowing the position of the object within each image to be determined. Correlating object positions between images from cameras 7 allows image-analysis system to determine the location in 3D space of object 814, and analyzing sequences of images allows image-analysis system to reconstruct 3D motion of object using conventional motion algorithms.

In identifying the location of an object in an image according to an embodiment of the present invention, light sources are turned on. One or more images are captured using cameras. In some embodiments, one image from each camera is captured. In other embodiments, a sequence of images is captured from each camera. The images from the two cameras can be closely correlated in time (e.g., simultaneous to within a few milliseconds) so that correlated images from the two cameras can be used to determine the 3D location of the object. A threshold pixel brightness is applied to distinguish object pixels from background pixels. This can also include identifying locations of edges of the object based on transition points between background and object pixels. In some embodiments, each pixel is first classified as either object or background based on whether it exceeds the threshold brightness cutoff. Once the pixels are classified, edges can be detected by finding locations where background pixels are adjacent to object pixels. In some embodiments, to avoid noise artifacts, the regions of background and object pixels on either side of the edge may be required to have a certain minimum size (e.g., 2, 4 or 8 pixels).

In other embodiments, edges can be detected without first classifying pixels as object or background. For example, $\Delta\beta$ can be defined as the difference in brightness between adjacent pixels, and $|\Delta\beta|$ above a threshold can indicate a transition from background to object or from object to background between adjacent pixels. (The sign of $\Delta\beta$ can indicate the direction of the transition.) In some instances where the object's edge is actually in the middle of a pixel, there may be a pixel with an intermediate value at the boundary. This can be detected, e.g., by computing two brightness values for a pixel i: $\beta L=(\beta i+\beta i-1)/2$ and $\beta R=(\beta i+\beta i+1)/2$, where pixel (i-1) is to the left of pixel i and pixel (i+1) is to the right of pixel i. If pixel i is not near an edge, $|\beta L-\beta R|$ will generally be close to zero; if pixel is near an edge, then $|\beta L-\beta R|$ will be closer to 1, and a threshold on $|\beta L-\beta R|$ can be used to detect edges.

In some instances, one part of an object may partially occlude another in an image; for example, in the case of a hand, a finger may partly occlude the palm or another finger. Occlusion edges that occur where one part of the object partially occludes another can also be detected based on smaller but distinct changes in brightness once background pixels have been eliminated.

Detected edges can be used for numerous purposes. For example, as previously noted, the edges of the object as viewed by the two cameras can be used to determine an approximate location of the object in 3D space. The position of the object in a 2D plane transverse to the optical axis of the camera can be determined from a single image, and the offset (parallax) between the position of the object in time-correlated images from two different cameras can be used to determine the distance to the object if the spacing between the cameras is known.

Further, the position and shape of the object can be determined based on the locations of its edges in time-correlated images from two different cameras, and motion (including articulation) of the object can be determined from analysis of successive pairs of images. An object's motion and/or position is reconstructed using small amounts of information. For example, an outline of an object's shape, or silhouette, as seen from a particular vantage point can be used to define tangent lines to the object from that vantage point in various planes, referred to herein as "slices." Using as few as two different vantage points, four (or more) tangent lines from the vantage points to the object can be obtained in a given slice. From these four (or more) tangent lines, it is possible to determine the position of the object in the slice and to approximate its cross-section in the slice, e.g., using one or more ellipses or other simple closed curves. As another example, locations of points on an object's surface in a particular slice can be determined directly (e.g., using a time-of-flight camera), and the position and shape of a cross-section of the object in the slice can be approximated by fitting an ellipse or other simple closed curve to the points. Positions and cross-sections determined for different slices can be correlated to construct a 3D model of the object, including its position and shape. A succession of images can be analyzed using the same technique to model motion of the object. Motion of a complex object that has multiple separately articulating members (e.g., a human hand) can be modeled using these techniques.

More particularly, an ellipse in the xy plane can be characterized by five parameters: the x and y coordinates of the center (xC, yC), the semimajor axis, the semiminor axis, and a rotation angle (e.g., angle of the semimajor axis relative to the x axis). With only four tangents, the ellipse is underdetermined. However, an efficient process for estimating the ellipse in spite of this fact involves making an initial working assumption (or "guess") as to one of the parameters and revisiting the assumption as additional information is gathered during the analysis. This additional information can include, for example, physical constraints based on properties of the cameras and/or the object. In some circumstances, more than four tangents to an object may be available for some or all of the slices, e.g., because more than two vantage points are available. An elliptical cross-section can still be determined, and the process in some instances is somewhat simplified as there is no need to assume a parameter value. In some instances, the additional tangents may create additional complexity. In some circumstances, fewer than four tangents to an object may be available for some or all of the slices, e.g., because an edge of the object is out of range of the field of view of one camera or because an edge was not detected. A slice with three tangents can be analyzed. For example, using two parameters from an ellipse fit to an adjacent slice (e.g., a slice that had at least four tangents), the system of equations for the ellipse and three tangents is sufficiently determined that it can be solved. As another option, a circle can be fit to the three tangents; defining a circle in a plane requires only three parameters (the center coordinates and the radius), so three tangents suffice to fit a circle. Slices with fewer than three tangents can be discarded or combined with adjacent slices.

To determine geometrically whether an object corresponds to an object of interest comprises, one approach is to look for continuous volumes of ellipses that define an object and discard object segments geometrically inconsistent with the ellipse-based definition of the object—e.g., segments that are too cylindrical or too straight or too thin or too small or too far away—and discarding these. If a sufficient number of ellipses remain to characterize the object and it conforms to the object of interest, it is so identified, and may be tracked from frame to frame.

In some embodiments, each of a number of slices is analyzed separately to determine the size and location of an elliptical cross-section of the object in that slice. This provides an initial 3D model (specifically, a stack of elliptical cross-sections), which can be refined by correlating the cross-sections across different slices. For example, it is expected that an object's surface will have continuity, and discontinuous ellipses can accordingly be discounted. Further refinement can be obtained by correlating the 3D model with itself across time. An object of interest can be brightly illuminated during the times when images are being captured. In some embodiments, the silhouettes of an object are extracted from one or more images of the object that reveal information about the object as seen from different vantage points. While silhouettes can be obtained using a number of different techniques, in some embodiments, the silhouettes are obtained by using cameras to capture images of the object and analyzing the images to detect object edges.

Figure 1C:
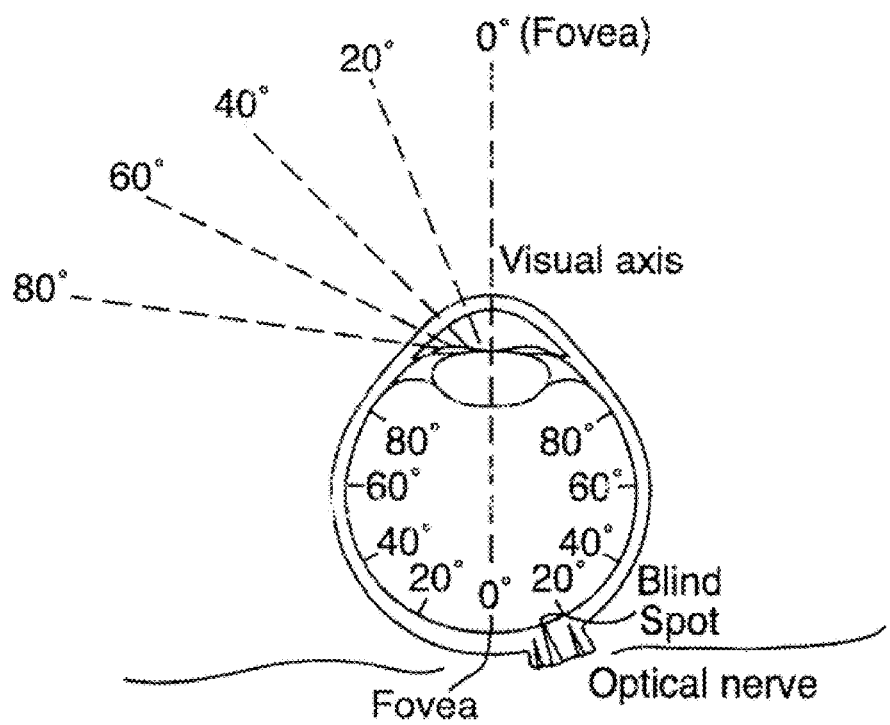
FIG. 1C shows an exemplary fovea visualization system.
Figure 1D:
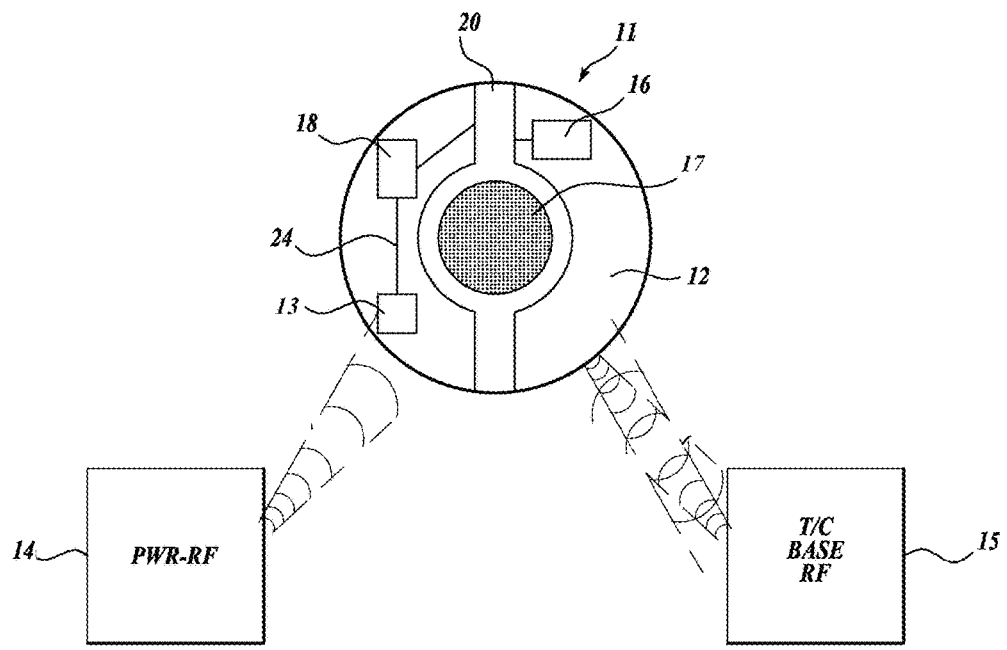
FIG. 1D shows one augmented reality (AR) implementation using a lens.

FIG. 1D shows one AR implementation of the system of FIG. 1A as a lens. The system in FIG. 1C shows schematically an active contact lens system in accordance with the present invention, which includes an active contact lens 11, a power supply 14 and a base station 15. The active contact lens 11 is formed on a transparent substrate 12, and includes one or more of a semi-transparent display 14, a display drive circuit 16, a data communications circuit 18, an energy transfer antenna 20, a biosensor module 22, and embedded interconnects 24 that functionally connect the various components assembled on the substrate 12. Preferably, the power supply 14 is an RF power supply and the energy transfer antenna 20 is an RF energy transfer antenna adapted to receive power via radio frequency waves for powering the components of the active contact lens 11. Preferably, the base station 15 is an RF ultra-low-power base station adapted to send and receives encrypted data via radio waves to and from the active contact lens 11, as described in more detail below. It is contemplated that the energy transfer antenna 20 may also be utilized for transmitting and/or receiving data for the data communications circuit 18. Alternatively, a separate antenna (not shown) may be provided in the data communications circuit 18 for exchanging data with the active contact lens 11.

The active contact lens 11 places a display 17 with light sources, for example lasers or OLEDs, substantially on the surface of cornea. For generating a sharp image on a user's retina from light generated by the display 17, the system can do: i) assembling or fabricating microlenses (not shown) under each pixel of the display 17 to form a collimated beam that may be projected to the retina such that the beam is interpreted as a far-field source; or ii) forming artificial images by determining the proper pixel switching algorithms using conventional imaging transformations. The active contact lens 11 may incorporate the semi-transparent display 17 that allows for providing visual information to the user; and/or the active contact lens 11 may incorporate one or more biosensors 13, for example to continuously monitor physiological and immunological conditions of the user.

The system includes EKG, EEG and EMG sensors on the eye, along with temperature sensors. The system also includes impedance sensors for bioelectrical impedance analysis (BIA) in estimating body composition, and in particular body fat. BIA determines the electrical impedance, or opposition to the flow of an electric current through body tissues which can then be used to calculate an estimate of total body water (TBW). TBW can be used to estimate fat-free body mass and, by difference with body weight, body fat.

In one embodiment, micro-acoustic elements (piezoelectric elements) may be placed insider or on a surface of the lens to transmit audible signals through bone resonance through the skull and to the cochlea. In other embodiments, the audible signals transmitted to the user using the micro-acoustic elements may be transmitted. High quality audio can be sent for secure voice communication or for listening to music/video. The audio can be an alarm or warning as well, for example, when the cardiac rhythm is determined to be outside a predetermined threshold based on monitored changes of the retinal vascularization. For example, the audible signal may be a recommended action and/or warning based on cardiac rhythm or an abnormal condition.

The radio frequency (RF) power supply 14 powers the active contact lens 11 through a base antenna (not shown) which is designed to cooperate with the RF energy transfer antenna 20 positioned on the active contact lens 11 to power the active elements on the lens 11 through the data communications circuit 18. It is contemplated that the power supply 14 may conveniently be worn by the user (for example, attached to a belt, integrated into the user's cloths, etc.) to provide a fully mobile system, and keep the power supply 14 in close proximity to the active contact lens 11. The RF ultra low-power encrypted telecommunication base station 15, which may be constructed separate from or integral with the power supply 14, exchanges data with the active contact lens 11. It is contemplated that the base station 15 may also be adapted to be worn by the user.

In one embodiment, a clear solar cell layer in the 3D chip can be used to generate power. In another embodiment, when not displaying, a bank of parallel LEDs can be used to generate electric power from light. The LED PN junctions are photovoltaic. While solar cells are made with a large area PN junction, a LED has only a small surface area and is not as efficient. Deposited on the same layer as the TFT and above the pixel electrode is a transparent power-generating element. In one embodiment, the power generating element is a semiconductor layer made using an amorphous silicon (a-Si) photodiode that generates photoelectric current. In this embodiment, light is absorbed only from the surface and in areas where the LCD is 'off' using an antireflective coating. The coating transforms the device into a 2-way mirror. The anti-reflective coating can consist of the amorphous silicon layer itself. By carefully choosing the layer thicknesses, light coming from under the silicon layer will be transmitted, while sunlight will be reflected and diffused back into the amorphous silicon layer. Another embodiment uses a photoactive, doped liquid crystal such as crystals with titanyl phthalocyanines (TiOPc). TiOPc is quite suitable as a photoreceptive material for liquid crystal diodes because TiOPc has sufficient light sensitivity at long wavelength region between 600 nm to 850 nm. The crystal can be formed by distributing a charge generation material (CGM) in a resin, among others. As for such CGM, for example, inorganic photoconductive materials such as selenium or alloys thereof, CdS, CdSe, CdSSe, ZnO, ZnS, metal or non-metal phthalocyanine compounds; azo compounds such as bisazo compounds, trisazo compounds, such as squarium compounds, azurenium compounds, perylene compounds, indigo compounds, quinacridone compounds, polyquinone-type compounds, cyanine dyes, xanthene dyes and transportation complexes composed of poly-N-carbazoles and trinitrofluorenone can be used. These compounds may be used either individually or two or more kinds in combination. The crystal becomes opaque when the electrodes force a voltage across it, meaning that photons are captured inside the crystal. The photons generate electron-hole pairs similar to those in a solar cell. The generated electron hole pairs flow to the biasing terminals, effectively supplying power. In this embodiment, no special coatings are needed, since light does not need to be preferentially reflected, and is only absorbed in pixels that are intentionally opaque. The pixel addressing circuitry turns pixel into an opaque state by applying a voltage across the pixel. This pixel can then capture all light impinging upon it from both the backlight and top without affecting the contrast of the display. In this embodiment, the more photons absorbed in the dark pixels, the higher the resulting contrast. Thus, by using appropriate photoactive liquid crystal, a portion of the absorbed photons can be turned into usable electrical power.

One embodiment harvests electricity from WiFi signals or cellular signals that are omnipresent. An ultra-wideband rectifying antenna used to convert microwave energy to DC power. This energy-scavenging antenna can be formed as part of a 3D chip with sensors, antennas and super-capacitors onto paper or flexible polymers. The antenna can generate energy from WiFi, cellular signal, radio signal, and TV signals as well as electric power lines.

The data exchanged between the active contact lens 11 and the base station 15 may include, for example, data to the display drive circuit 16 to refresh pixels in the display 17 to display the desired visual information. Concurrently, the biosensor(s) 13, typically disposed on the surface of the lens 11, may sample and analyze the corneal interstitial fluid, detect heart rate data, or the like. Biomarker measurement results are relayed back to the base station 15, which may be used to assess the user's health condition. The incorporation of biosensor(s) 13 onto the active contact lens 11 allows, for example, continuous sampling of the interstitial fluid on a user's cornea. This fluid is in indirect contact with blood serum via the capillaries in the structure of the eye and contains many of the markers that are used in blood analysis to determine a person's health condition. The sampling and analysis of this fluid allows for continuous assessment of a user's fatigue level and early detection of infectious components without taking a blood sample. The same interstitial fluid can be used to assess the user's blood glucose level allowing for continuous glucose monitoring without blood sampling for diabetic patients.

The system can use a bio-battery or an energy storing device that is powered by organic compounds, usually being glucose, such as the glucose in human blood. When enzymes in human bodies break down glucose, several electrons and protons are released. Therefore, by using enzymes to break down glucose, bio-batteries directly receive energy from glucose. These batteries then store this energy for present or later use. Like any cell battery, bio-batteries contain an anode, cathode, separator and electrolyte with each component layered on top of another in a 3D structure that is deposited on the plastic 3D chip. Between the anode and the cathode lies the electrolyte which contains a separator. The main function of the separator is to keep the cathode and anode separated, to avoid electrical short circuits. This system as a whole, allows for a flow of protons (H+) and electrons (e−) which ultimately generates electricity. Bio batteries are based on the amount of glucose available. The body decomposes materials to glucose (if they are not already in the proper stage) is the main step in getting the cycle started. Materials can be converted into glucose through the process of enzymatic hydrolysis. Enzymatic hydrolysis is the process in which cellulose (an insoluble substance) is converted to glucose by the addition of enzymes. Once glucose is present, oxygen and other enzymes can act on it to further produce protons and electrons. The bio-batteries use enzymes to convert glucose into energy. When glucose first enters the battery, it enters through the anode. In the anode the sugar is broken down, producing both electrons and protons: Glucose→Gluconolactone+2H++2e−. These electrons and protons produced now play an important role in creating energy. They travel through the electrolyte, where the separator redirects electrons to go through the mediator to get to the cathode.[1] On the other hand, protons are redirected to go through the separator to get to the cathode side of the battery. The cathode then consists of an oxidation reduction reaction. This reaction uses the protons and electrons, with the addition of oxygen gas, to produce water: O2+4H++4e− →2H2O. There is a flow created from the anode to the cathode which is what generates the electricity in the bio-battery. The flow of electrons and protons in the system are what create this generation of electricity.

Components of the system may also be included in a 3D plastic chip with a plurality of layers of components fabricated thereon. For example, the 3D plastic chip can be monolithic such as those discussed in U.S. Patent Application 20120193806 entitled 3D SEMICONDUCTOR DEVICE, among others. In some embodiments, the retinal vascularization monitoring components may be attached as a portion of a layer. In some of the embodiments discussed herein, the battery elements may be fabricated as part of the 3D IC device, or may be included as elements in a stacked layer. It may be noted as well that other embodiments may be possible where the battery elements are located externally to the stacked integrated component layers. Still further diversity in embodiments may derive from the fact that a separate battery or other energization component may also exist within the media insert, or alternatively these separate energization components may also be located externally to the media insert. In some embodiments, these media inserts with 3D IC layers may assume the entire annular shape of the media insert. Alternatively in some cases, the media insert may be an annulus whereas the stacked integrated components may occupy just a portion of the volume within the entire shape.

The active contact lens system allows for full situational awareness and mobility by enabling real-time information display to permit quick decision-making. The potential applications in gaming, virtual reality, and training are innumerable, and will be readily apparent to persons of skill in these arts.

Figure 1E:
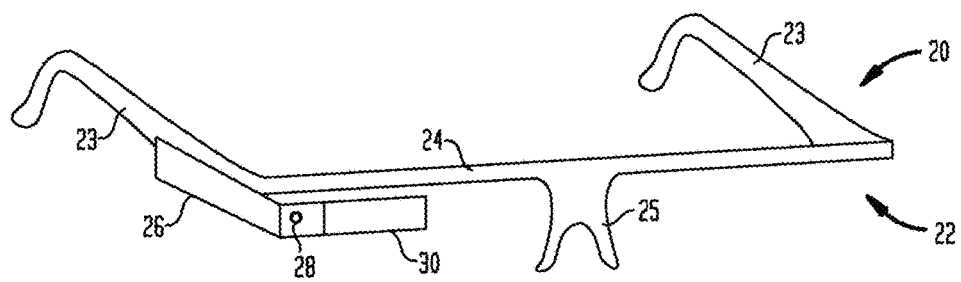
FIG. 1E shows one AR implementation using eye glasses.

FIG. 1E illustrates an example system 20 for receiving, transmitting, and displaying data. The system 20 is shown in the form of a wearable computing device eyeglass 22. The wearable computing device 22 may include side-arms 23, a center frame support 24, and a bridge portion with nosepiece 25. In the example shown in FIG. 1D, the center frame support 24 connects the side-arms 23. The wearable computing device 22 does not include lens-frames containing lens elements. The wearable computing device 22 may additionally include an onboard computing system 26 and a video camera 28.

The wearable computing device 22 may include a single lens element 30 that may be coupled to one of the side-arms 23 or the center frame support 24. The lens element 30 may include a display such as the laser projector described above, and may be configured to overlay computer-generated graphics upon the user's view of the physical world. In one example, the single lens element 30 may be coupled to the inner side (i.e., the side exposed to a portion of a user's head when worn by the user) of the extending side-arm 23. The single lens element 30 may be positioned in front of or proximate to a user's eye when the wearable computing device 22 is worn by a user. For example, the single lens element 30 may be positioned below the center frame support 24.

Video Feature Tracking and Matching

The GPU 3 can help with recognizing objects, as well as rasterizing the laser paintings to the eye. In one embodiment, the CPU and GPUs are in one device with a heterogeneous multicore microprocessor architecture, combining a general purpose processing core(s) and basic graphics core(s) into one processor package, with different clocks for the graphics core and the central processing core. The GPUs provide thousands of processors for parallel processing, similar to the way the brain operates in parallel.

In one embodiment, a KLT tracking process and a SIFT feature extraction process to enable real-time processing of high resolution video. The KLT tracking process computes displacement of features or interest points between consecutive video frames when image motion is fairly small. Feature selection is done by finding maximas of a saliency measure (minimum eigen-values of the 2×2 structure matrix obtained from gradient vectors. It is evaluated over the complete image and a subsequent non-maximal suppression is performed. Assuming a local translational model between subsequent video frames, the feature displacements are computed using Newton's method to minimize the sum of squared distances (SSD) within a tracking window around the feature position in the two images.

A multi-resolution KLT tracker allows handling larger image motion while multiple tracking iterations at each scale increases its accuracy. Features tracks are often lost after a few frames of tracking; hence new features are selected in a particular video frame only after tracking features in a few successive frames. This maintains a roughly fixed number of features in the tracker.

GPU-KLT maps these various steps to sets of different fragment programs. The multi-resolution pyramid of the image and its gradients are computed by a series of two-pass separable convolutions performed in fragment programs. The KLT cornerness map is computed in two render passes. The first pass computes the minimum eigen value of the 2×2 gradient matrix at each pixel and the two passes together accumulate the cornerness value within a 7×7 window centered at each pixel. During feature re-selection, the neighborhood of existing features is invalidated; early Z-culling avoids computations in these image regions. The cornerness map is transferred back to the CPU where non-maximal suppression is done to build the final feature-list. KLT tracking performs a fixed number of tracking iterations at each image resolution starting with the coarsest pyramid level. Each tracking iteration constructs a linear system of equations in two unknowns for each interest point, AX=B and directly solves them to update the estimated displacement. All steps are performed on the GPU. A SSD residual is computed between the two image patches of a particular KLT feature in order to reject features tracked inaccurately. Conditional statements are avoided in fragment programs by tracking a constant number of features and rejecting inaccurate tracks after the final tracking iteration on the GPU and before reading back the feature-list.

The Scale Invariant Feature Transform (SIFT) process performs extraction of interest points invariant to translation, rotation, scaling and illumination changes in images. It first constructs a Gaussian scale-space pyramid from the input image while also calculating the gradients and difference-of-gaussian (DOG) images at these scales. Interest points are detected at the local extremas within the DOG scale space. Once multiple keypoints have been detected at different scales, the image gradients in the local region around each feature point are encoded using orientation histograms and represented in the form of a rotationally invariant feature descriptor. The construction of the Gaussian scale space pyramid is accelerated on the GPU using fragment programs for separable convolution. The intensity image, gradients and the DOG values are stored in a RGBA texture and computed in the same pass. Blending operations in graphics hardware are used to find local extremas in the DOG pyramid in parallel at all pixel locations. The Depth test and the Alpha test is used to threshold these keypoints; The local principal curvatures of the image intensity around the keypoint is inspected; this involves computing the ratio of eigenvalues of the 2£2 Hessian matrix of the image intensity at that point. The keypoint locations are implicitly computed in image-sized, binary buffers, one for each scale in the pyramid. A fragment program compresses (a factor of 32) the binary bitmap into RGBA data, which is readback to the CPU and decoded there. At this stage, a list of keypoints and their scales have been retrieved. Since reading back the gradient pyramid (stored in texture memory) to the CPU is expensive, the subsequent steps in SIFT are also performed on the GPU. Gradient vectors near the keypoint location are Gaussian weighted and accumulated inside an orientation histogram by another fragment program. The orientation histogram is read back to the CPU, where its peaks are detected. Computing histograms on the GPU is expensive and doing it on the CPU along with a small readback is a little faster. The final step involves computing 128 element SIFT descriptors. These consist of a set of orientation histograms built from 16£16 image patches in invariant local coordinates determined by the associated keypoint scale, location and orientation. SIFT descriptors cannot be efficiently computed completely on the GPU, as histogram bins must be blended to remove quantization noise. This step is partitioned between the CPU and the GPU. Each feature's gradient vector patch is resampled, weighted using a Gaussian mask using blending support on the GPU. The resampled and weighted gradient vectors are collected into a tiled texture block which is subsequently transferred back to the CPU and then used to compute the descriptors. This CPU-GPU partition was done to minimize data readback from the GPU since transferring the whole gradient pyramid back to the CPU is impractical. Moreover texture re-sampling and blending are efficient operations on the GPU and are performed there. This also produces a compact tiled texture block which can be transferred to the CPU in a single readback. GPU-SIFT gains a large speed-up in the Gaussian scale-space pyramid construction and keypoint localization steps. The compressed readback of binary images containing feature positions reduces the readback data-size by a factor of 32. The feature orientation and descriptors computation is partitioned between the CPU and GPU in a way that minimizes data transfer from GPU to CPU.

Video Compression

In one embodiment, the video feature tracking and matching described above is used to compress video. The operation is as follows:

1) send the first few minutes of video using conventional or compressed video and simultaneously determine predetermine facial and body features;

2) after the start up period, for each frame determine whether the current frame only has facial/body changes and if so look for an updated position of the features and transmit a vector indicating facial and body feature changes to the remote computer the remote computer converts the vector of changed facial features to an image of the user's face and body position 3) otherwise, there are significant changes to the frame and so loop back to (1) to do a fresh compression cycle.

The process achieves a very high compression ratio since only a vector of feature position changes are sent as a vector and the vector is converted back into frame image by the remote computer. Moreover, if significant scene changes occur (such as new participants entering the conference, or participant picks up a book and show book to the camera), then the system reverts back to H.264 compression of full image.

Face Recognition

Face detection can be performed on board the camera for autofocus of the camera. Additionally, the face detection can be used to identify regions in the video that should be encoded at high resolution for certain applications.

A parallelized implementation of convolutional neural networks (CNNs) is done with parallelizing the detection process using the GPU. The convolutional network consists of a set of layers each of which contains one or more planes. Approximately centered and normalized images enter at the input layer. Each unit in a plane receives input from a small neighborhood in the planes of the previous layer. The idea of connecting units to local receptive fields dates back to the 1960s with the perceptron and Hubel and Wiesel's discovery of locally sensitive, orientation-selective neurons in the cat's visual system. The general strategy of a convolutional network is to extract simple features at a higher resolution, and then convert them into more complex features at a coarser resolution. The simplest was to generate coarser resolution is to sub-sample a layer by a factor of 2. This, in turn, is a clue to the convolutions kernel's size.

The weights forming the receptive field for a plane are forced to be equal at all points in the plane. Each plane can be considered as a feature map which has a fixed feature detector that is convolved with a local window which is scanned over the planes in the previous layer. Multiple planes are usually used in each layer so that multiple features can be detected. These layers are called convolutional layers.

The GPU supports a fast, automatic system for face recognition which is a combination of a local image sample representation, a self-organizing map network, and a convolutional network for face recognition. For the images in the training set, a fixed size window is stepped over the entire image and local image samples are extracted at each step. At each step the window is moved by 4 pixels. Next, a self-organizing map (e.g. with three dimensions and five nodes per dimension) is trained on the vectors from the previous stage. The SOM quantizes the 25-dimensional input vectors into 125 topologically ordered values. The three dimensions of the SOM can be thought of as three features. The SOM can be replaced with the Karhunen-Loeve transform. The KL transform projects the vectors in the 25-dimensional space into a 3-dimensional space. Next, the same window as in the first step is stepped over all of the images in the training and test sets. The local image samples are passed through the SOM at each step, thereby creating new training and test sets in the output space created by the self-organizing map. (Each input image is now represented by 3 maps, each of which corresponds to a dimension in the SOM. The size of these maps is equal to the size of the input image divided by the step size. A convolutional neural network, or alternatively a multilayer perceptron neural network, is trained on the newly created training set.

The self-organizing map provides a quantization of the image samples into a topological space where inputs that are nearby in the original space are also nearby in the output space, which results in invariance to minor changes in the image samples, and the convolutional neural network provides for partial invariance to translation, rotation, scale, and deformation. Substitution of the Karhunen-Lo'eve transform for the self organizing map produced similar but slightly worse results. The method is capable of rapid classification, requires only fast, approximate normalization and preprocessing, and consistently exhibits better classification performance than the eigenfaces approach on the database considered as the number of images per person in the training database is varied from 1 to 5.

Face Detection/Gesture Detection

As discussed above, a parallelized implementation of convolutional neural networks (CNNs) is done with parallelizing the detection process using the GPU. This can be used for autofocus of the camera. Once the face is detected, the GPUs can also be used to detect gestures as commands. Motion features are first computed on the input image sequence (stationary camera assumed). The face detector is then employed to obtain a user-centric representation, and again a classifier to discriminate between gestures is learned using a variant of AdaBoost. A real-time version of this classifier is deployed using the GPU.

To calculate the motion features, the optical flow for each frame is determined. The optical flow vector field F is then split into horizontal and vertical components of the flow, Fx and Fy, each of which is then half-wave rectified into four non-negative channels Fx+, Fx−, Fy+, Fy−. A channel corresponding to motion magnitude F0 is obtained by computing the L2 norm of the four basic channels. These five non-negative channels are then normalized to facilitate gesture recognition in soft-real time where frame rates can be variable, and to account for different speed of motion by different users.

Given a vector v that represents the optical flow for a given pixel, the system computes $v=v/(\|v\|+e)$, where e is used to squash optical flow vectors with very small magnitude introduced by noise. Next, each of the five channels is box-filtered to reduce sensitivity to small translations by the user performing the gesture. This final set of five channels: ˆFx+, ˆFx−, ˆFy+, ˆFy−, ˆF0 will be used as the motion features for each frame.

A gesture is represented as a collection of movements required to complete a single phase of the gesture, rather than just capture a subset of the gesture phase. Hence, the system aggregates the motion features over a temporal history of the last k frames, for some k which is large enough to capture all frames from a gesture phase.

Face detection is used to create a normalized, user centric view of the user. The image is scaled based on the radius of the detected face, and is then cropped and centered based on the position of the face. The frame is cropped and resized to a 50×50 pixel region centered around the user. All five motion feature channels described above are flattened into a single vector which will be used to determine the gesture being performed.

A multi-class boosting process AdaBoost is used such as the one at http://multiboost.sourceforge.net AdaBoost takes the motion features as input. The supervised training is based on a set of labeled gestures. A set of weak learners is generated based on thresholding value from a particular component of the motion feature vector. The output of the final strong learner on motion feature v for class label is determined using weights chosen by AdaBoost.

Panaroma Stitching

The GPUs 3 of can perform panaroma stitching so that the user can see a 180 degree immersive view. The GPU operations are done pipeline fashion as follows: Radial Distortion Correction. Next, the GPUs perform Keypoint Detection & Extraction (Shi-Tomasi/SIFT). Keypoint Matching is done, and the GPUs recover Homography (RANSAC). Next, the GPUs create a Laplacian Pyramid. A Projective Transform is done, and a Multi-Band Blend is the last stage of the pipeline.

Object Recognition

The CPU/GPU can identify video objects and then generate metadata for video objects contained within the captured video frames. For each of the captured video frames, the CPU/GPUs may execute program instructions to: (i) detect whether the video frame contains a video object, (ii) generate meta data for each detected video object, and (iii) cause data storage to store the relevant portions of the video and the metadata describing objects in the video for search purposes.

Generating the metadata may be carried out in various ways. For instance, generating the meta data may be carried out by segmenting video objects within a video frame and then representing features of each segmented video object. As an example, the feature representation may be color appearance information, that is, the analytical data may comprise color data based on the color or colors of a video object. The analytical data based on the color or colors of a video object may include any of a variety of color data. For example, for any given video object, the color data may include Red Green Blue (RGB) color space data, Hue Saturation Value (HSV) color space data, YCrCb color space data, and/or YUV color space data.

As another example, the metadata may include data based on pixel intensity, data indicating which pixels are part of the video object, a unique identifier of the video object, and/or structural information associated with the video object. The structural information may include information pertaining to edges, curvature, and/or texture of the video object, for example. The structural information may include information that indicates how close a structure of the video object matches a circle, rectangle, star, or some other arbitrary shape. The metadata may also include confidence measures of the other types of data in the metadata. The confidence measures may indicate a determination of how likely a video object is a given type of object, such as a vehicle, person, animal, bag, or some other type of object.

In one embodiment, the GPU detects an object using color and then tracks the object by:

1. Create a masking image by comparing each pixel with a target color value. Convert pixels that fall within the range to white, and convert those that fall outside the range to black.

2. Find the centroid of the target color. The centroid of the tracked color defines the center position for the overlay image. A multipass pixel-processing kernel is used to compute a location. The output of this phase is a 1×1-pixel image, containing the coordinate of the centroid in the first two components (pixel.rg) and the area in the third component (pixel.b). The area is used to estimate the distance of the object from the camera.

3. Composite an image over the detected object. Assuming the shape of the object does not change with respect to the frame, then the change in area of the tracked color is proportional to the square of the distance of the object from the viewer. This information is used to scale the overlay image, so that the overlay image increases or decreases in size appropriately.

In another embodiment, Shape-Based Matching (SBM) is used for recognizing partially occluded objects which is very robust against illumination changes. It is closely related to correlation. The main difference is that SBM uses the inner product of normalized edge gradient vectors as similarity measure instead of raw image intensity. To recognize an object, the search image is correlated with the model using the similarity measure of SBM. The model image is fitted in all possible translations within the search image and a score is assigned to each position. As correlation based methods do not cope with any other object transformation those must be handled by evaluating the results of multiple correlations.

In one embodiment, a Hough transform (HT) can be used to recognize any analytically describable shape]. A generalization of the Hough transform (GHT) who manages any discrete shape is also available [1]. Ulrich presents a modification of the generalized Hough transform (MGHT), gaining real-time performance by taking advantage of resolution hierarchies, which is not as straight forward as it might first seem. The principles of it are described below. Initially, a model of the object to be recognized is generated. A gradient map is generated from the model image and edges are extracted. Then a table, mapping edge gradient direction (represented as an angle) to offset vectors to the center of the model, is created.

In the search procedure a gradient map of the search image is used. For each gradient direction (represented as an angle) a number of displacement vectors are looked up using the table. A vote is placed on each position pointed at by a displacement vector. If the point belongs to an edge of the object, at least one of the vectors point at the center of the object that is to be found, and a vote will be placed for that position. After this is done, a peak has appeared in the voting space at the center of the object as this is the single point that the most dislocation vectors points at (at least one for each gradient belonging to the edge of the object in the search image).

To utilize a resolution pyramid the model image is divided into tiles for all levels but the coarsest. A separate lookup table is generated for each tile. Searching then begins with a regular search at the coarsest pyramid level which yields a coarse position of the object which will be refined for each level in the pyramid.

In the refinement, the entire gradient map is considered as before, but only the mapping table connected to the tiles that have dislocation vectors pointing to a neighborhood of the known position are evaluated for each gradient. This way the amount of votes to place, and the voting space itself is much smaller than before.

In another embodiment, a chamfer distance transform of an edge image is used as a model. Another edge image is extracted from the search image. To find the position of the object a similarity measure is evaluated for each potential position (as for cross correlation). The similarity measure is the mean distance from each edge in the search image to the closest edge in the model for the current translation. This is obtained by accumulating samples from the distance map of the model for each edge in the search image. If there is a perfect match, the mean distance is 0.

Other object recognition techniques can be used to tap into the GPU's parallel stream processing.

Eye Scanning System

In one mode, the LED of the display 17 can be operated in reverse as an image sensor. In this mode, one of the LED is used to project light into the retina, and the remaining LEDs are operated in reverse as imaging sensors.

Figure 2B:
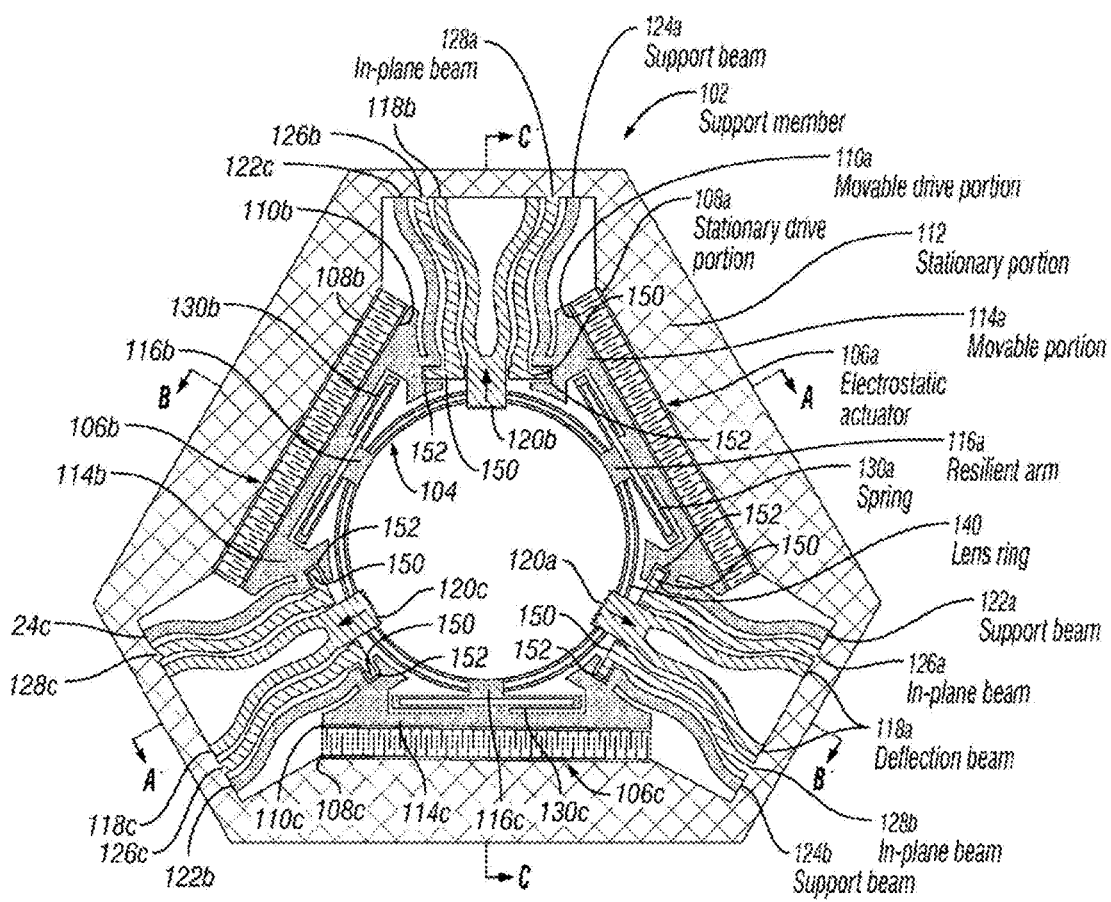
FIGS. 2B-2C show an exemplary autofocus engine.

Referring now to FIG. 2A, a representation of a region of the retinal vascularization of an eye is depicted. In particular, a series of vessels are shown as they would be viewed from the anterior portion of the eye by an imaging scanner. In the present exemplary representation, the vessels branch off each other forming a dense pattern that can be useful to study the vessel tortuosity, the angle and number of bifurcations, and the length to width ratio. Monitoring temporal changes of the vessels or their overall structures can be useful to predict risk to cardiac conditions including, for example, microvascular disease or diabetes, and cardiac rhythm. The region of the retinal vascularization of an eye of FIG. 2A is illustrated with a digital overlay useful for the analysis of changes of the retinal vascularization. In particular, the exemplary overlay can be useful to divide the observed region of the retinal vascularization into concentric grid sections that can be used for filtering and/or image segmentation. In some embodiments, grid sections may take other forms such including line patterns and the like. Concentric grid sections however may be preferred for filtering and image segmentation due to the arcuate shape of the cornea conforming to the spherical shape of the eye. When eye movement or flickering prevents processing of the different segmented portions, image processing techniques that include edge recognition can be used to connect the different segments allowing for the analysis of the portion of the retinal vascularization being monitored. In the present example, changes of each vessel may be identified in relation to each of the particular concentric regions A, B, or C. By focusing the image analysis to a specific portion/region, the amount of image processing and analysis can be reduced thereby lowering power and processing requirements. For example, the frequency in which each of the regions is imaged can be alternated depending on the changes in pulse detected. In another scenario, only a first region that includes a segment of a pulsating vessel may be monitored until a change that falls outside a predetermined threshold is detected. Average changes in vessel diameter during the cardiac cycle may be approximately 1.2 μm for arteries and 1.6 μm for veins. Accordingly, a signal may be outputted once a change in diameter of an identified artery is less than 0.8 μm and greater than 1.6 μm over a short period of time. Similarly, a change in the diameter of a vein that is less than 1.2 μm or greater than 2.0 μm may trigger a signal. The signal may activate additional sensors, increase the rate of image capture, record the abnormality, and/or send a message to the user. The message can be sent to the user via an audio signal and/or a visual signal provided by the ophthalmic device itself or a device in wireless communication with the ophthalmic device. The width or diameter of a vessel may be monitored at point 45. Point 45 may have been identified as a positive pulsating point of reference during an initial retinal examination using high definition imaging technique including mydriatic and/or nonmydriatic retinal screenings. When an abnormal change in diameter or rate of pulsations is initially detected, point of reference 45 can be analyzed in conjunction with point of reference 610 pointing to the same vessel. Analysis at both points of reference may be used to provide the system with more measurements for the determination of blood pressure, for example. In some embodiments, other reference points on pulsating/non-pulsating vessels in a different region may also be monitored, simultaneously or in alternating modes, to ensure that the change is uniform throughout the vascularization. For example, at additional point of reference 55 in region C.

The device 100 of the present disclosure may be a contact lens resting on the anterior surface of a patient's eye 110. The contact lens may be a soft hydrogel lens and can include a silicone containing component. A "silicone-containing component" is one that contains at least one [—Si—O—] unit in a monomer, macromer or prepolymer. Preferably, the total Si and attached O are present in the silicone-containing component in an amount greater than about 20 weight percent, and more preferably greater than 30 weight percent of the total molecular weight of the silicone-containing component. Useful silicone-containing components preferably comprise polymerizable functional groups such as acrylate, methacrylate, acrylamide, methacrylamide, vinyl, N-vinyl lactam, N-vinylamide, and styryl functional groups.

Embedded by the hydrogel portion partially or entirely, or in some embodiments placed onto the hydrogel portion, can be a functionalized media insert 150. The media insert 150 can be used to encapsulate functionalized elements 105, including electronic and electromechanical elements, and in some embodiments one or more energy source (in section 140 magnified in FIG. 2B). In some embodiments, the functionalized elements 105 can preferably be located outside of the optical zone 175, such that the device does not interfere with the patient's sight. Functionalized elements 105 may be powered through an external means, energy harvesters, and/or energization elements contained in the ophthalmic device 100. For example, in some embodiments the power may be received using an antenna receiving RF signals that is in communication with the electronic elements 105.

Optical Correction

An optical correction media insert 150 can be used and can be fully encapsulated to protect and contain the electronic components. In certain embodiments, the encapsulating material may be semi-permeable, for example, to prevent specific substances, such as water, from entering the media insert and to allow specific substances, such as ambient gasses, fluid samples, and/or the byproducts of reactions within energization elements, to penetrate and/or escape from the media insert. The media insert may be included in/or the lens, which may also comprise a polymeric biocompatible material. The device may include a rigid center, soft skirt design wherein a central rigid optical element comprises the media insert. In some specific embodiments, the media insert may be in direct contact with the atmosphere and/or the corneal surface on respective anterior and posterior surfaces, or alternatively, the media insert may be encapsulated in the device. The periphery of the ophthalmic device may be a soft skirt material, including, for example, a hydrogel material. The system can provide an environment to monitor the retinal microvascularization.

Figure 2C:
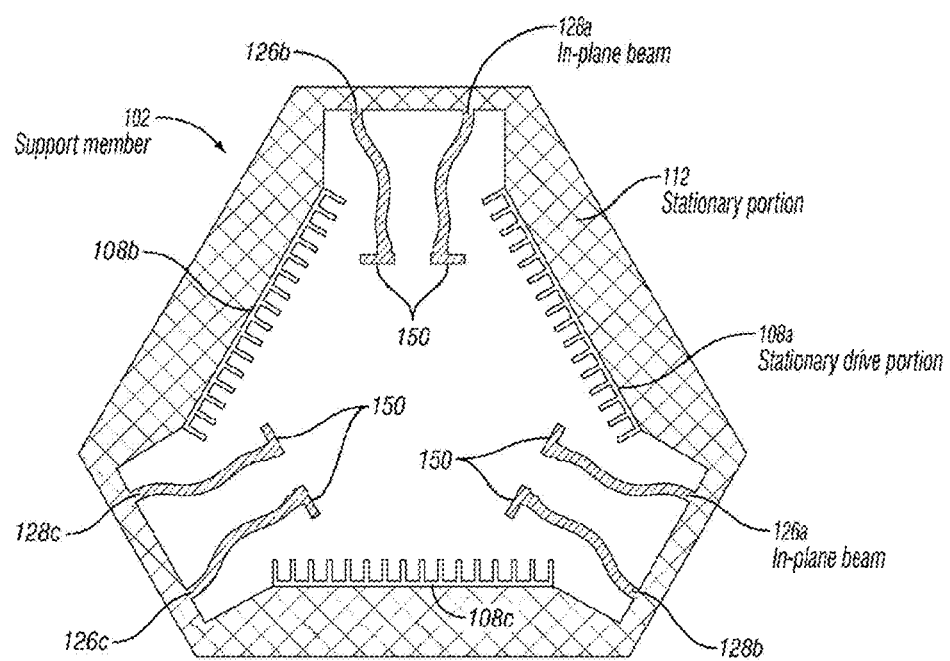

The insert 150 can be a conventional contact lens, or can be computer controlled to provide the best focusing, in particular for elder patients with short and long range reading issues that require bifocal glasses. In one embodiment shown in FIGS. 2B-2C, lens element 103 is a single lens element of a lens stack that is mounted within a camera. Representatively, as illustrated in FIG. 1A, lens element 103 is mounted within autofocus actuator 100. Lens stack 105, which includes lens elements 105A, 105B and 105C, and image sensor 107 are mounted behind lens element 103. The object of interest 119 is positioned in front of lens element 103. According to this arrangement, when lens element 103 is in the resting position, it is at a focal position of maximum focus distance, i.e., a position for focus at infinity. Thus, adjusting lens element 103 in a direction of arrow 117 moves lens element 103 closer to the object of interest and decreases the focus distance so that the associated camera can focus on objects, which are outside of the focus distance when lens element 103 is in the resting state. This second focal position can be any focal position other than the focal position for focus at infinity. Representatively, when power is applied to actuator 100, lens element 103 moves in a direction of arrow 117 to any number of focal positions within the range of movement. The range of movement is preferably any range which ensures that deflection beam 118 remains in a deflected or biased position. For example, the range of movement may be between the resting focal position illustrated in FIG. 1A (see also FIG. 2A) and the plane of support member 102.

Movement of lens element 103 may be driven by electrostatic actuator 106. In one embodiment, electrostatic actuator 106 may be a comb drive having a stationary drive portion 108 and a movable drive portion 110. Stationary drive portion 108 and movable drive portion 110 may include fingerswhich interlock with one another to drive movement of stationary drive portion 108 with respect to movable drive portion 110. Representatively, in one embodiment, stationary drive portion 108 is mounted to support member 102 while movable drive portion 110 is suspended in front of stationary drive portion 108 such that the application of a voltage moves movable drive portion 110 in a direction of arrow 117 while stationary drive portion remains stationary.

To move movable drive portion 110 in the desired direction when a voltage is applied, movable drive portion 110 must be displaced with respect to stationary drive portion 108 in the resting or non-actuated state as such that application of pulls movable drive portion 110 toward stationary drive portion 108. Displacement of movable drive portion 110 with respect to stationary drive portion 108 is achieved by deflection beam 118. In particular, in one embodiment, deflection beam 118 is an elongated structure that extends radially inward from support member 102 to lens element 103. Deflection beam 118 may frictionally engage with the edge of lens element 103 such that when lens element 103 is loaded into support member 102 in a downward direction (i.e., toward lens stack 105), lens element 103 applies an outward force to deflection beam 118. In one embodiment, the force moves deflection beam 118 radially outwards. Since this force is in turn applied along a length of deflection beam 118, the beam becomes unstable and buckles. This creates a bi-stable configuration in which the beam snaps out of plane, notionally in either direction. The direction of deflection may be controlled by the direction of insertion of the lens element. In this case, the deflection beam 118 buckles in a downward direction, which in turn displaces movable drive portion 110 below stationary drive portion 108. Movable drive portion 110, and in turn lens element 103, will remain in this position until a voltage sufficient to overcome the downward force of deflection beam 118 and pull movable drive portion 110 toward stationary drive portion 108 is applied.

It is important that deflection beam 118 remain in some degree of the buckled configuration during operation. To maintain the buckled configuration, the range of movement of lens element 103 may be limited using any suitable limiting structure or system. For example, in one embodiment, front case 109 having retaining arms 113A, 113B is positioned along the front face of support member 102. Retaining arms 113A, 113B are positioned above resilient arm 116 and deflection beam 118 and extend down into the plane of support member. Retaining arms 113A, 113B are dimensioned to contact and stop deflection beam 118 and resilient arm 116 from passing above the support member plane as movable drive portion 110 drives lens element 103 in a direction of arrow 117. This in turn, limits the movement of lens element 103 to just below the plane of support member 102. A back case 111 may further be attached to a bottom face of support member 102 such that actuator 100 is enclosed within front case 109 and back case 111.

It is contemplated that any other suitable structure or system may be implemented to limit the range of movement of lens element 103 so that deflection beam 118 remains in a deflected state which is below the plane of support member 102. For example, a single retaining arm that limits movement of movable drive portion 110 may be used. Alternatively, the voltage applied to actuator 100 may be controlled so as not to raise deflection beam 118 beyond the desired deflected position.

In particular, movable drive portion 110A is connected to movable portion 114A, support beams 122A, 124A and lens ring 140. In addition, deflection beams 118A are connected to lens ring 140. Thus, movement of movable drive portion 110A also drives movement of each of these components in the same direction. Meanwhile, in-plane beams 126A and 128A are independent from the moveable components and attached to stationary portion 112. Thus, in-plane beams 126A and 128A remain stationary when movable drive portion 110A moves. The loading of a lens element within lens ring 140 applies an outward force to support ends 120A, 120B and 120C causing deflection beams 118A, 118B and 118C to buckle and assume an out-of-plane configuration. When lens element 103 is loaded into lens ring 140, a force in a direction of arrows 304 is applied to support ends 120A, 120B and 120C causing the associated deflection beams 118A, 118B and 118C to buckle. The buckling of deflection beams 118A, 118B and 118C draws the movable ends attached to lens ring 140 out-of-plane in a direction parallel to the direction in which lens element 103 is loaded into lens ring 140. For example, in this embodiment, lens element 103 is loaded from above and pressed down into lens ring 140. Deflection beams 118A, 118B and 118C will therefore deflect and pull lens ring 140 to a position that is below the plane of support member 102. This position can be considered the resting position of autofocus actuator 100 or position of the actuator in the non-actuated state. In other words, the position of autofocus actuator 100 when power is not being applied. As can further be seen from this view, when deflection beam 118A deflects, it also pulls movable drive portion 110A down with respect to stationary drive portion 108A. Thus, movable drive portion 110A and stationary drive portion 108A are displaced relative to each other along the optical axis in the non-actuated state. Deflection beams 118B, 118C and their associated drive portions 108B, 110E and 108C, 110C operate in a similar manner. Since the in-plane beams, for example in-plane beams 126A, 128A and stationary portion 112 are independent from the movable components, these features remain in-plane with respect to support member 102. It is further noted that in some embodiments, the outward force, illustrated by arrow 304, on lens ring 140 caused by loading of lens element 103 within lens ring, will cause other portions of lens ring 140 to be drawn inward. In particular, the portions of lens ring 140 attached to resilient arms 116A, 116B and 116C may be pulled radially inward to allow the outward force in the direction of arrows 304. Each of resilient arms 116A, 116B and 116C may include spring members 130A, 130B and 130C, respectively. Spring members 130A, 130B and 130C help to maintain in-plane alignment of the electrostatic actuators 106A, 106B and 106C in that they allow resilient arms 116A, 116B and 116C, respectively, to expand in response to the radially inward force without pulling the movable drive portion away from the stationary drive portion.

Retinal Vascularization

Figure 2D:
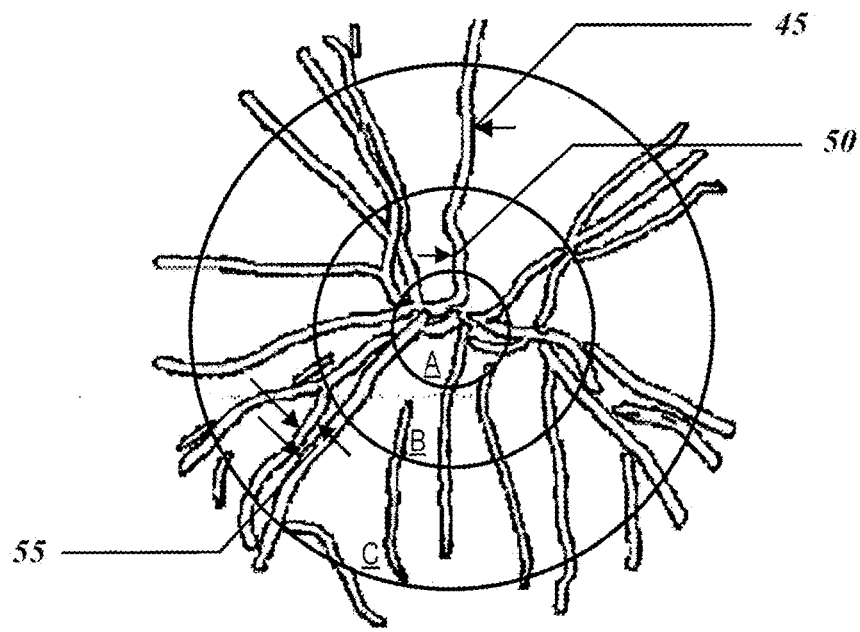
FIG. 2D shows an exemplary system to detect eye abnormality and other vital signs such as heart rate, blood pressure, among others.

Referring now to FIG. 2D, an enlarged portion 140 of the cross section depicted in FIG. 2A showing aspects of the retinal vascularization monitoring system is depicted. In particular, the enlarged portion 140 illustrates a hydrogel portion 116 of the ophthalmic device 100 resting on ocular fluid 112 on the anterior surface of the eye 110. Ocular fluid 112 can include any one, or a combination of: tear fluid, aqueous humour, vitreous humour, and other interstitial fluids located in the eye. The hydrogel portion 116 may encapsulate the media insert 150 which in some embodiments can include energization elements 118, such as a battery and a load, along with components of the retinal vascularization monitoring system 126.

The retinal vascularization monitoring system 126 can include a wireless communication element 120, such as a RF antenna in connection with a controller 122. The controller 122 can be used to control a piezoelectric transducer 130, a pick up 135, and an electronic feedback circuit including an amplifier 124 and a band-pass filter 126 which can all be powered through the energization elements 118 contained within the media insert 150. The piezoelectric transducer 130 and the pick-up 135 can resonate a signal and measure the change in the return signal to image one or more portions of the retinal vascularization. The piezo-electric transducer may be placed in contact with the retina. Upon the application of electrical pulses, ultrasound pulses emanate from it for them to echo back to the surface and converted back to electrical pulses that can then be processed by the system and formed into an image. The images can be produced by surfaces or boundaries between two different types of tissues, such as the vessels forming part of the retina and the vitreous humour of the eye. Because the vitreous humour is a relatively homogenous gelatinous mass with insignificant amounts of solid matter, an identified portion of the retinal vascularization may be imaged by changing the focal depth from the transducer. The focal depth can be adjusted by changing the time delay between the electrical pulses. By sending ultrasound pulses at different depths around an identified pulsating vessel, the imaging definition required to identify small temporal changes in width and displacement can be achieved.

Retinal Scanning for Authentication

In one embodiment, the system can monitor retinal vascularization in an identified region/zone having portions of one or more pulsating vessels. These regions/zones can be identified using imaging systems or cameras that are capable of reproducing high definition images of the microvascularization in the retina. Imaging systems may include non-invasive OCT systems, or any other highly reliable mydriatic or nonmydriatic diagnostic imaging method used for geometrical measurements of retinal structures. Depth, shape, relative position, and structure of the vascularization may be pre-programmed into the ophthalmic device in order to lower processing/energy consumption requirements and reliably identify the target points in the areas monitored. In preferred embodiments, target points can be easily identifiable image features, such as, edges, crossing, or line boundaries of vessels.

In one embodiment, a computer can be locked after a period of inactivity. When the user returns to the computer, a moving object can be shown on the display screen of the computing system for the user to look at. The system then performs eye tracking and can determine that a path associated with the eye movement of the user substantially matches a path associated with the moving object on the display and switch to be in an unlocked mode of operation including unlocking the computer.

Eye Exercise

The treatment of amblyopia, weak eye, and strabismus, incorporates the old-fashioned patching principle with eye-exercising programs by performing various manners of intermittent occlusion, termed herein: occlusion-and-exercising sessions. Additionally, the occlusion-and-exercising sessions are designed to avoid predictability. This is done by using a plurality of time intervals, preferably between three and ten each, for occlusion and for no occlusion. For example, six time intervals may be provided for occlusion and six time intervals may be provided for no occlusion. When the number of intervals is large enough, for example, greater than three, predictability is avoided, even if the intervals are used in sequence. It will be appreciated that the number of occlusion and no occlusion intervals need not be equal, and that a greater number of intervals, for example, 20 or 501 may be used. Thus, in accordance with the present invention, a session, which may last, for example, between 20 minutes and ten hours, is constructed of a repeated sequence of occlusion and no-occlusion intervals. It will be appreciated that gradual transitions may also be employed between no occlusion and occlusion intervals.

Amblyopia treatment, in accordance with the present invention, is preferably employed in stages, which may be constructed as follows:

i. An initiating stage: The initiating stage is preferably employed during the first few weeks of treatment. During the initiating stage, the occlusion-and-exercising session each day is relatively short, preferably about three hours a day, occlusion intervals are relatively short, preferably, less than 100 seconds, and no occlusion intervals are relatively long, preferably greater than 60 seconds.

ii. A core stage: The core stage is preferably employed following the initiating stage, for between several months and about a year, or possibly longer. It represents the bulk of the treatment. During the core stage, the occlusion-and-exercising session each day is relatively long, preferably about eight hours a day, occlusion intervals are relatively long, preferably, greater than 60 seconds, and no occlusion intervals are preferably between 30 and 600 seconds.

iii. A maintenance stage: The maintenance stage is preferably employed following the core stage, for about 1 year. It will be appreciated that shorter or longer periods are also possible. During the maintenance stage, the occlusion-and-exercising session each day is very short, preferably about one hour a day, occlusion intervals are relatively long, preferably, greater than 60 seconds, and no occlusion intervals are preferably between 30 and 600 seconds.

It will be appreciated that the occlusion-and-exercising session each day may be broken up into several sessions, whose duration is as that of the recommended daily session, provided they are applied during the same day.

Restoring Sights for the Blind

One embodiment captures sights observable from one or more eyes. The video information is then provided to the laser sweeper that paints the rods and cones. Such laser energy deposition on the rods/cones causes a particular image to be displayed on the blind eye. The result is vision for the blind.

Food Intake Determination

In an example, the AR/VR can estimate a three-dimensional volume of each type of food, The imaging device can estimate the quantities of specific foods from pictures or images of those foods by volumetric analysis of food from multiple perspectives and/or by three-dimensional modeling of food from multiple perspectives. The system can use projected laser beams to create a virtual or optical fiduciary marker in order to measure food size or scale. In an example, pictures of food can be taken at different times. In an example, a camera can be used to take pictures of food before and after consumption. The amount of food that a person actually consumes (not just the amount ordered or served) can be estimated by the difference in observed food volume from the pictures before and after consumption.

In an example, images of food can be automatically analyzed in order to identify the types and quantities of food consumed. In an example, pictures of food taken by a camera or other picture-taking device can be automatically analyzed to estimate the types and amounts of specific foods, ingredients, or nutrients that a person is consumes. In an example, an initial stage of an image analysis system can comprise adjusting, normalizing, or standardizing image elements for better food segmentation, identification, and volume estimation. These elements can include: color, texture, shape, size, context, geographic location, adjacent food, place setting context, and temperature (infrared). In an example, a device can identify specific foods from pictures or images by image segmentation, color analysis, texture analysis, and pattern recognition.

In various examples, automatic identification of food types and quantities can be based on: color and texture analysis; image segmentation; image pattern recognition; volumetric analysis based on a fiduciary marker or other object of known size; and/or three-dimensional modeling based on pictures from multiple perspectives. In an example, a device can collect food images that are used to extract a vector of food parameters (such as color, texture, shape, and size) that are automatically associated with vectors of food parameters in a database of such parameters for food identification. In an example, a device can collect food images that are automatically associated with images of food in a food image database for food identification. In an example, specific ingredients or nutrients that are associated with these selected types of food can be estimated based on a database linking foods to ingredients and nutrients. In another example, specific ingredients or nutrients can be measured directly. In various examples, a device for measuring consumption of food, ingredient, or nutrients can directly (or indirectly) measure consumption at least one selected type of food, ingredient, or nutrient.

In an example, selected types of foods, ingredients, and/or nutrients can be identified by the patterns of light that are reflected from, or absorbed by, the food at different wavelengths. In an example, a light-based sensor can detect food consumption or can identify consumption of a specific food, ingredient, or nutrient based on the reflection of light from food or the absorption of light by food at different wavelengths. In an example, an optical sensor can detect fluorescence. In an example, an optical sensor can detect whether food reflects light at a different wavelength than the wavelength of light shone on food. In an example, an optical sensor can be a fluorescence polarization immunoassay sensor, chemiluminescence sensor, thermoluminescence sensor, or piezoluminescence sensor. In an example, a light-based food-identifying sensor can collect information concerning the wavelength spectra of light reflected from, or absorbed by, food. In an example, an optical sensor can be a chromatographic sensor, spectrographic sensor, analytical chromatographic sensor, liquid chromatographic sensor, gas chromatographic sensor, optoelectronic sensor, photochemical sensor, and photocell. In an example, an optical sensor can analyze modulation of light wave parameters by the interaction of that light with a portion of food. In an example, an optical sensor can detect modulation of light reflected from, or absorbed by, a receptor when the receptor is exposed to food. In an example, an optical sensor can emit and/or detect white light, infrared light, or ultraviolet light. In an example, a light-based food-identifying sensor can identify consumption of a selected type of food, ingredient, or nutrient with a spectral analysis sensor. In various examples, a food-identifying sensor can identify a selected type of food, ingredient, or nutrient with a sensor that detects light reflection spectra, light absorption spectra, or light emission spectra. In an example, a spectral measurement sensor can be a spectroscopy sensor or a spectrometry sensor. In an example, a spectral measurement sensor can be a white light spectroscopy sensor, an infrared spectroscopy sensor, a near-infrared spectroscopy sensor, an ultraviolet spectroscopy sensor, an ion mobility spectroscopic sensor, a mass spectrometry sensor, a backscattering spectrometry sensor, or a spectrophotometer. In an example, light at different wavelengths can be absorbed by, or reflected off, food and the results can be analyzed in spectral analysis.

In an example, a food-consumption monitor or food-identifying sensor can be a microphone or other type of sound sensor. In an example, a sensor to detect food consumption and/or identify consumption of a selected type of food, ingredient, or nutrient can be a sound sensor. In an example, a sound sensor can be an air conduction microphone or bone conduction microphone. In an example, a microphone or other sound sensor can monitor for sounds associated with chewing or swallowing food. In an example, data collected by a sound sensor can be analyzed to differentiate sounds from chewing or swallowing food from other types of sounds such as speaking, singing, coughing, and sneezing.

In an example, a sound sensor can include speech recognition or voice recognition to receive verbal input from a person concerning food that the person consumes. In an example, a sound sensor can include speech recognition or voice recognition to extract food selecting, ordering, purchasing, or consumption information from other sounds in the environment.

In an example, a sound sensor can be worn or held by a person. In an example, a sound sensor can be part of a general purpose device, such as a cell phone or mobile phone, which has multiple applications. In an example, a sound sensor can measure the interaction of sound waves (such as ultrasonic sound waves) and food in order to identify the type and quantity of food that a person is eating.

In an example, a food-consumption monitor or food-identifying sensor can be a chemical sensor. In an example, a chemical sensor can include a receptor to which at least one specific nutrient-related analyte binds and this binding action creates a detectable signal. In an example, a chemical sensor can include measurement of changes in energy wave parameters that are caused by the interaction of that energy with food. In an example, a chemical sensor can be incorporated into a smart utensil to identify selected types of foods, ingredients, or nutrients. In an example, a chemical sensor can be incorporated into a portable food probe to identify selected types of foods, ingredients, or nutrients. In an example, a sensor can analyze the chemical composition of a person's saliva. In an example, a chemical sensor can be incorporated into an intraoral device that analyzes microsamples of a person's saliva. In an example, such an intraoral device can be adhered to a person's upper palate.

In various examples, a food-consumption monitor or food-identifying sensor can be selected from the group consisting of: receptor-based sensor, enzyme-based sensor, reagent based sensor, antibody-based receptor, biochemical sensor, membrane sensor, pH level sensor, osmolality sensor, nucleic acid-based sensor, or DNA/RNA-based sensor; a biomimetic sensor (such as an artificial taste bud or an artificial olfactory sensor), a chemiresistor, a chemoreceptor sensor, a electrochemical sensor, an electroosmotic sensor, an electrophoresis sensor, or an electroporation sensor; a specific nutrient sensor (such as a glucose sensor, a cholesterol sensor, a fat sensor, a protein-based sensor, or an amino acid sensor); a color sensor, a colorimetric sensor, a photochemical sensor, a chemiluminescence sensor, a fluorescence sensor, a chromatography sensor (such as an analytical chromatography sensor, a liquid chromatography sensor, or a gas chromatography sensor), a spectrometry sensor (such as a mass spectrometry sensor), a spectrophotometer sensor, a spectral analysis sensor, or a spectroscopy sensor (such as a near-infrared spectroscopy sensor); and a laboratory-on-a-chip or microcantilever sensor.

In an example, a food-consumption monitor or food-identifying sensor can be an electromagnetic sensor. In an example, a device for measuring food consumption or identifying specific nutrients can emit and measure electromagnetic energy. In an example, a device can expose food to electromagnetic energy and collect data concerning the effects of this interaction which are used for food identification. In various examples, the results of this interaction can include measuring absorption or reflection of electromagnetic energy by food. In an example, an electromagnetic sensor can detect the modulation of electromagnetic energy that is interacted with food.

In an example, an electromagnetic sensor that detects food or nutrient consumption can detect electromagnetic signals from the body in response to the consumption or digestion of food. In an example, analysis of this electromagnetic energy can help to identify the types of food that a person consumes. In an example, a device can measure electromagnetic signals emitted by a person's stomach, esophagus, mouth, tongue, afferent nervous system, or brain in response to general food consumption. In an example, a device can measure electromagnetic signals emitted by a person's stomach, esophagus, mouth, tongue, afferent nervous system, or brain in response to consumption of selected types of foods, ingredients, or nutrients.

In various examples, a sensor to detect food consumption or identify consumption of a selected type of nutrient can be selected from the group consisting of: neuroelectrical sensor, action potential sensor, ECG sensor, EKG sensor, EEG sensor, EGG sensor, capacitance sensor, conductivity sensor, impedance sensor, galvanic skin response sensor, variable impedance sensor, variable resistance sensor, interferometer, magnetometer, RF sensor, electrophoretic sensor, optoelectronic sensor, piezoelectric sensor, and piezocapacitive sensor.

In an example, a food-consumption monitor or food-identifying sensor can be a location sensor. In an example, such a sensor can be geographic location sensor or an intra-building location sensor. A device for detecting food consumption and/or indentifying a selected type of food, ingredient, or nutrient consumed can use information concerning a person's location as part of the means for food consumption detection and/or food identification. In an example, a device can identify when a person in a geographic location that is associated with probable food consumption. In an example, a device can use information concerning the person's geographic location as measured by a global positioning system or other geographic location identification system. In an example, if a person is located at a restaurant with a known menu or at a store with a known food inventory, then information concerning this menu or food inventory can be used to narrow down the likely types of food being consumed. In an example, if a person is located at a restaurant, then the sensitivity of automated detection of food consumption can be adjusted. In an example, if a person is located at a restaurant or grocery store, then visual, auditory, or other information collected by a sensor can be interpreted within the context of that location.

In an example, a device can identify when a person is in a location within a building that is associated with probable food consumption. In an example, if a person is in a kitchen or in a dining room within a building, then the sensitivity of automated detection of food consumption can be adjusted. In an example, a food-consumption monitoring system can increase the continuity or level of automatic data collection when a person is in a restaurant, in a grocery store, in a kitchen, or in a dining room. In an example, a person's location can be inferred from analysis of visual signals or auditory signals instead of via a global positioning system. In an example, a person's location can be inferred from interaction between a device and local RF beacons or local wireless networks.

In an example, a sensor to monitor, detect, or sense food consumption or to identify consumption of a selected type of food, ingredient, or nutrient can be a wearable sensor that is worn by the person whose food consumption is monitored, detected, or sensed. In an example, a wearable food-consumption monitor or food-identifying sensor can be worn directly on a person's body. In an example a wearable food-consumption monitor or food-identifying sensor can be worn on, or incorporated into, a person's clothing.

In various examples, a device for measuring a person's consumption of at least one selected type of food, ingredient, or nutrient can provide feedback to the person that is selected from the group consisting of: feedback concerning food consumption (such as types and amounts of foods, ingredients, and nutrients consumed, calories consumed, calories expended, and net energy balance during a period of time); information about good or bad ingredients in nearby food; information concerning financial incentives or penalties associated with acts of food consumption and achievement of health-related goals; information concerning progress toward meeting a weight, energy-balance, and/or other health-related goal; information concerning the calories or nutritional components of specific food items; and number of calories consumed per eating event or time period.

In various examples, a device for measuring a person's consumption of at least one selected type of food, ingredient, or nutrient can provide feedback to the person that is selected from the group consisting of: augmented reality feedback (such as virtual visual elements superimposed on foods within a person's field of vision); changes in a picture or image of a person reflecting the likely effects of a continued pattern of food consumption; display of a person's progress toward achieving energy balance, weight management, dietary, or other health-related goals; graphical display of foods, ingredients, or nutrients consumed relative to standard amounts (such as embodied in pie charts, bar charts, percentages, color spectrums, icons, emoticons, animations, and morphed images); graphical representations of food items; graphical representations of the effects of eating particular foods; holographic display; information on a computer display screen (such as a graphical user interface);

lights, pictures, images, or other optical feedback; touch screen display; and visual feedback through electronically-functional eyewear.

In various examples, a device for measuring a person's consumption of at least one selected type of food, ingredient, or nutrient can provide feedback to the person that is selected from the group consisting of: advice concerning consumption of specific foods or suggested food alternatives (such as advice from a dietician, nutritionist, nurse, physician, health coach, other health care professional, virtual agent, or health plan); electronic verbal or written feedback (such as phone calls, electronic verbal messages, or electronic text messages); live communication from a health care professional; questions to the person that are directed toward better measurement or modification of food consumption; real-time advice concerning whether to eat specific foods and suggestions for alternatives if foods are not healthy; social feedback (such as encouragement or admonitions from friends and/or a social network); suggestions for meal planning and food consumption for an upcoming day; and suggestions for physical activity and caloric expenditure to achieve desired energy balance outcomes.

In an example, a device for measuring a person's consumption of at least one selected type of food, ingredient, or nutrient can identify and track the selected types and amounts of foods, ingredients, or nutrients that the person consumes in an entirely automatic manner. In an example, such identification can occur in a partially automatic manner in which there is interaction between automated and human identification methods.

In an example, a device for measuring a person's consumption of at least one selected type of food, ingredient, or nutrient can identify and track food consumption at the point of selection or point of sale. In an example, a device for monitoring food consumption or consumption of selected types of foods, ingredients, or nutrients can approximate such measurements by tracking a person's food selections and purchases at a grocery store, at a restaurant, or via a vending machine. Tracking purchases can be relatively easy to do, since financial transactions are already well-supported by existing information technology. In an example, such tracking can be done with specific methods of payment, such as a credit card or bank account. In an example, such tracking can be done with electronically-functional food identification means such as bar codes, RFID tags, or electronically-functional restaurant menus. Electronic communication for food identification can also occur between a food-consumption monitoring device and a vending machine.

In an example, a device for measuring a person's consumption of at least one selected type of food, ingredient, or nutrient can identify food using information from a food's packaging or container. In an example, this information can be detected optically by means of a picture or optical scanner. In an example, food can be identified directly by automated optical recognition of information on food packaging, such as a logo, label, or barcode. In various examples, optical information on a food's packaging or container that is used to identify the type and/or amount of food can be selected from the group consisting of: bar code, food logo, food trademark design, nutritional label, optical text recognition, and UPC code. With respect to meals ordered at restaurants, some restaurants (especially fast-food restaurants) have standardized menu items with standardized food ingredients. In such cases, identification of types and amounts of food, ingredients, or nutrients can be conveyed at the point of ordering (via an electronically-functional menu) or purchase (via purchase transaction). In an example, food can be identified directly by wireless information received from a food display, RFID tag, electronically-functional restaurant menu, or vending machine. In an example, food or its nutritional composition can be identified directly by wireless transmission of information from a food display, menu, food vending machine, food dispenser, or other point of food selection or sale and a device that is worn, held, or otherwise transported with a person.

However, there are limitations to estimating food consumption based on food selections or purchases in a store or restaurant. First, a person might not eat everything that they purchase through venues that are tracked by the system. The person might purchase food that is eaten by their family or other people and might throw out some of the food that they purchase. Second, a person might eat food that they do not purchase through venues that are tracked by the system. The person might purchase some food with cash or in venues that are otherwise not tracked. The person might eat food that someone else bought, as when eating as a guest or family member. Third, timing differences between when a person buys food and when they eat it, especially for non-perishable foods, can confound efforts to associate caloric intake with caloric expenditure to manage energy balance during a defined period of time. For these reasons, a robust device for measuring food consumption should (also) be able to identify food at the point of consumption.

In an example, a device, method, or system for measuring a person's consumption of at least one selected type of food, ingredient, or nutrient can identify and track a person's food consumption at the point of consumption. In an example, such a device, method, or system can include a database of different types of food. In an example, such a device, method, or system can be in wireless communication with an externally-located database of different types of food. In an example, such a database of different types of food and their associated attributes can be used to help identify selected types of foods, ingredients, or nutrients. In an example, a database of attributes for different types of food can be used to associate types and amounts of specific ingredients, nutrients, and/or calories with selected types and amounts of food.

In an example, such a database of different types of foods can include one or more elements selected from the group consisting of: food color, food name, food packaging bar code or nutritional label, food packaging or logo pattern, food picture (individually or in combinations with other foods), food shape, food texture, food type, common geographic or intra-building locations for serving or consumption, common or standardized ingredients (per serving, per volume, or per weight), common or standardized nutrients (per serving, per volume, or per weight), common or standardized size (per serving), common or standardized number of calories (per serving, per volume, or per weight), common times or special events for serving or consumption, and commonly associated or jointly-served foods.

In an example, a picture of a meal as a whole can be automatically segmented into portions of different types of food for comparison with different types of food in a food database. In an example, the boundaries between different types of food in a picture of a meal can be automatically determined to segment the meal into different food types before comparison with pictures in a food database. In an example, a picture of a meal with multiple types of food can be compared as a whole with pictures of meals with multiple types of food in a food database. In an example, a picture of a food or a meal comprising multiple types of food can be compared directly with pictures of food in a food database.

In an example, a picture of food or a meal comprising multiple types of food can be adjusted, normalized, or standardized before it is compared with pictures of food in a food database. In an example, food color can be adjusted, normalized, or standardized before comparison with pictures in a food database. In an example, food size or scale can be adjusted, normalized, or standardized before comparison with pictures in a food database. In an example, food texture can be adjusted, normalized, or standardized before comparison with pictures in a food database. In an example, food lighting or shading can be adjusted, normalized, or standardized before comparison with pictures in a food database.

In an example, a food database can be used to identify the amount of calories that are associated with an indentified type and amount of food. In an example, a food database can be used to identify the type and amount of at least one selected type of food that a person consumes. In an example, a food database can be used to identify the type and amount of at least one selected type of ingredient that is associated with an identified type and amount of food. In an example, a food database can be used to identify the type and amount of at least one selected type of nutrient that is associated with an identified type and amount of food. In an example, an ingredient or nutrient can be associated with a type of food on a per-portion, per-volume, or per-weight basis.

In an example, a vector of food characteristics can be extracted from a picture of food and compared with a database of such vectors for common foods. In an example, analysis of data concerning food consumption can include comparison of food consumption parameters between a specific person and a reference population. In an example, data analysis can include analysis of a person's food consumption patterns over time. In an example, such analysis can track the cumulative amount of at least one selected type of food, ingredient, or nutrient that a person consumes during a selected period of time.

In various examples, data concerning food consumption can be analyzed to identify and track consumption of selected types and amounts of foods, ingredients, or nutrient consumed using one or more methods selected from the group consisting of: linear regression and/or multivariate linear regression, logistic regression and/or probit analysis, Fourier transformation and/or fast Fourier transform (FFT), linear discriminant analysis, non-linear programming, analysis of variance, chi-squared analysis, cluster analysis, energy balance tracking, factor analysis, principal components analysis, survival analysis, time series analysis, volumetric modeling, neural network and machine learning.

In an example, a device for measuring a person's consumption of at least one selected type of food, ingredient, or nutrient can identify the types and amounts of food consumed in an automated manner based on images of that food. In various examples, food pictures can be analyzed for automated food identification using methods selected from the group consisting of: image attribute adjustment or normalization; inter-food boundary determination and food portion segmentation; image pattern recognition and comparison with images in a food database to identify food type; comparison of a vector of food characteristics with a database of such characteristics for different types of food; scale determination based on a fiduciary marker and/or three-dimensional modeling to estimate food quantity; and association of selected types and amounts of ingredients or nutrients with selected types and amounts of food portions based on a food database that links common types and amounts of foods with common types and amounts of ingredients or nutrients. In an example, automated identification of selected types of food based on images and/or automated association of selected types of ingredients or nutrients with that food can occur within a wearable or hand-held device. In an example, data collected by a wearable or hand-held device can be transmitted to an external device where automated identification occurs and the results can then be transmitted back to the wearable or hand-held device.

In an example, a device and system for measuring a person's consumption of at least one selected type of food, ingredient, or nutrient can take pictures of food using a digital camera. In an example, a device and system for measuring a person's consumption of at least one selected type of food, ingredient, or nutrient can take pictures of food using an imaging device selected from the group consisting of: smart watch, smart bracelet, fitness watch, fitness bracelet, watch phone, bracelet phone, wrist band, or other wrist-worn device; arm bracelet; and smart ring or finger ring. In an example, a device and system for measuring a person's consumption of at least one selected type of food, ingredient, or nutrient can take pictures of food using an imaging device selected from the group consisting of: smart phone, mobile phone, cell phone, holophone, and electronic tablet.

In an example, a device and system for measuring a person's consumption of at least one selected type of food, ingredient, or nutrient can take pictures of food using an imaging device selected from the group consisting of: smart glasses, visor, or other eyewear; electronically-functional glasses, visor, or other eyewear; augmented reality glasses, visor, or other eyewear; virtual reality glasses, visor, or other eyewear; and electronically-functional contact lens. In an example, a device and system for measuring a person's consumption of at least one selected type of food, ingredient, or nutrient can take pictures of food using an imaging device selected from the group consisting of: smart utensil, fork, spoon, food probe, plate, dish, or glass; and electronically-functional utensil, fork, spoon, food probe, plate, dish, or glass. In an example, a device and system for measuring a person's consumption of at least one selected type of food, ingredient, or nutrient can take pictures of food using an imaging device selected from the group consisting of: smart necklace, smart beads, smart button, neck chain, and neck pendant.

In an example, an imaging device can take multiple still pictures or moving video pictures of food. In an example, an imaging device can take multiple pictures of food from different angles in order to perform three-dimensional analysis or modeling of the food to better determine the volume of food. In an example, an imaging device can take multiple pictures of food from different angles in order to better control for differences in lighting and portions of food that are obscured from some perspectives. In an example, an imaging device can take multiple pictures of food from different angles in order to perform three-dimensional modeling or volumetric analysis to determine the three-dimensional volume of food in the picture. In an example, an imaging device can take multiple pictures of food at different times, such as before and after an eating event, in order to better determine how much food the person actually ate (as compared to the amount of food served). In an example, changes in the volume of food in sequential pictures before and after consumption can be compared to the cumulative volume of food conveyed to a person's mouth by a smart utensil to determine a more accurate estimate of food volume consumed. In various examples, a person can be prompted by a device to take pictures of food from different angles or at different times.

In an example, a device that identifies a person's food consumption based on images of food can receive food images from an imaging component or other imaging device that the person holds in their hand to operate. In an example, a device that identifies a person's food consumption based on images of food can receive food images from an imaging component or other imaging device that the person wears on their body or clothing. In an example, a wearable imaging device can be worn in a relatively fixed position on a person's neck or torso so that it always views the space in front of a person. In an example, a wearable imaging device can be worn on a person's wrist, arm, or finger so that the field of vision of the device moves as the person moves their arm, wrist, and/or fingers. In an example, a device with a moving field of vision can monitor both hand-to-food interaction and hand-to-mouth interaction as the person moves their arm, wrist, and/or hand. In an example, a wearable imaging device can comprise a smart watch with a miniature camera that monitors the space near a person's hands for possible hand-to-food interaction and monitors the near a person's mouth for hand-to-mouth interaction.

In an example, selected attributes or parameters of a food image can be adjusted, standardized, or normalized before the food image is compared to images in a database of food images or otherwise analyzed for identifying the type of food. In various examples, these image attributes or parameters can be selected from the group consisting of: food color, food texture, scale, image resolution, image brightness, and light angle.

In an example, a device and system for identifying types and amounts of food consumed based on food images can include the step of automatically segmenting regions of a food image into different types or portions of food. In an example, a device and system for identifying types and amounts of food consumed based on food images can include the step of automatically identifying boundaries between different types of food in an image that contains multiple types or portions of food. In an example, the creation of boundaries between different types of food and/or segmentation of a meal into different food types can include edge detection, shading analysis, texture analysis, and three-dimensional modeling. In an example, this process can also be informed by common patterns of jointly-served foods and common boundary characteristics of such jointly-served foods.

In an example, estimation of specific ingredients or nutrients consumed from information concerning food consumed can be done using a database that links specific foods (and quantities thereof) with specific ingredients or nutrients (and quantities thereof). In an example, food in a picture can be classified and identified based on comparison with pictures of known foods in a food image database. In an example, such food identification can be assisted by pattern recognition software. In an example, types and quantities of specific ingredients or nutrients can be estimated from the types and quantities of food consumed.

In an example, attributes of food in an image can be represented by a multi-dimensional food attribute vector. In an example, this food attribute vector can be statistically compared to the attribute vector of known foods in order to automate food identification. In an example, multivariate analysis can be done to identify the most likely identification category for a particular portion of food in an image. In various examples, a multi-dimensional food attribute vector can include attributes selected from the group consisting of: food color; food texture; food shape; food size or scale; geographic location of selection, purchase, or consumption; timing of day, week, or special event; common food combinations or pairings; image brightness, resolution, or lighting direction; infrared light reflection; spectroscopic analysis; and person-specific historical eating patterns.

Patient Monitoring

Patient monitoring can include determining the cardiac rhythm from the rate of pulsations of a vessel over a particular period of time and/or the displacement/changes of vessel(s) over time. The monitoring may be triggered, for example, based on a timer function, blink actuation, or upon receiving a signal from a wireless device in communication with the ophthalmic device. In some embodiments, the wireless may serve as a user interface and may be a drug pump, smartphone, personal computer, tablet, and the such. Transmission of information with the wireless device can occur, for example, via a RF frequency, a local area network (LAN), and/or a private area network (PAN), depending on the communication device and functionality implemented by the ophthalmic device. An audio/visual signal alert may be sent to the user when either the determined cardiac rhythm and/or determined rate of vascular displacement are outside a predetermined threshold. For example, a signal may be outputted when the system detects that the cardiac rhythm has increased/decreased to a hazardous level. The signal may be sent using a wireless device in communication with the ophthalmic device and/or through an audible signal using micro-acoustic elements included in the ophthalmic device. An n actuation signal may be sent to a drug delivery apparatus to deliver a drug/active agent. The drug delivery mechanism may include, for example, a drug pump in wireless communication with the ophthalmic device. Optionally the signal may be correlated with a specific event imputed by the patient using the wireless device as a user interface. For example, through a selection from a menu listing activities that can influence cardiac rhythm or blood pressure. The action and/or feedback can be recorded on a cloud to improve future analysis, keep a medical record that can be accessed by an eye care practitioner, and/or tailor the retinal vascularization monitoring system to the particular patient. In some embodiments, these recorded actions/records can also be sent/stored using the wireless cellular device.

In addition to identifying blood pressure using imaging techniques. The system can have a number of medical sensors. One embodiment includes bioelectrical impedance (BI) spectroscopy sensors in addition to or as alternates to EKG sensors and heart sound transducer sensors. BI spectroscopy is based on Ohm's Law: current in a circuit is directly proportional to voltage and inversely proportional to resistance in a DC circuit or impedance in an alternating current (AC) circuit. Bioelectric impedance exchanges electrical energy with the patient body or body segment. The exchanged electrical energy can include alternating current and/or voltage and direct current and/or voltage. The exchanged electrical energy can include alternating currents and/or voltages at one or more frequencies. For example, the alternating currents and/or voltages can be provided at one or more frequencies between 100 Hz and 1 MHz, preferably at one or more frequencies between 5 KHz and 250 KHz. A BI instrument operating at the single frequency of 50 KHz reflects primarily the extra cellular water compartment as a very small current passes through the cell. Because low frequency (<1 KHz) current does not penetrate the cells and that complete penetration occurs only at a very high frequency (>1 MHz), multi-frequency BI or bioelectrical impedance spectroscopy devices can be used to scan a wide range of frequencies.

In a tetrapolar implementation, two electrodes on the wrist watch or wrist band are used to apply AC or DC constant current into the body or body segment. The voltage signal from the surface of the body is measured in terms of impedance using the same or an additional two electrodes on the watch or wrist band. In a bipolar implementation, one electrode on the wrist watch or wrist band is used to apply AC or DC constant current into the body or body segment. The voltage signal from the surface of the body is measured in terms of impedance using the same or an alternative electrode on the watch or wrist band. The system may include a BI patch 1400 that wirelessly communicates BI information with the wrist watch. Other patches 1400 can be used to collect other medical information or vital parameter and communicate with the wrist watch or base station or the information could be relayed through each wireless node or appliance to reach a destination appliance such as the base station, for example. The system can also include a head-cap 1402 that allows a number of EEG probes access to the brain electrical activities, EKG probes to measure cranial EKG activity, as well as BI probes to determine cranial fluid presence indicative of a stroke. As will be discussed below, the EEG probes allow the system to determine cognitive status of the patient to determine whether a stroke had just occurred, the EKG and the BI probes provide information on the stroke to enable timely treatment to minimize loss of functionality to the patient if treatment is delayed.

Bipolar or tetrapolar electrode systems can be used in the BI instruments. Of these, the tetrapolar system provides a uniform current density distribution in the body segment and measures impedance with less electrode interface artifact and impedance errors. In the tetrapolar system, a pair of surface electrodes (I1, I2) is used as current electrodes to introduce a low intensity constant current at high frequency into the body. A pair of electrodes (E1, E2) measures changes accompanying physiological events. Voltage measured across E1-E2 is directly proportional to the segment electrical impedance of the human subject. Circular flat electrodes as well as band type electrodes can be used. In one embodiment, the electrodes are in direct contact with the skin surface. In other embodiments, the voltage measurements may employ one or more contactless, voltage sensitive electrodes such as inductively or capacitively coupled electrodes. The current application and the voltage measurement electrodess in these embodiments can be the same, adjacent to one another, or at significantly different locations. The electrode(s) can apply current levels from 20 uA to 10 mA rms at a frequency range of 20-100 KHz. A constant current source and high input impedance circuit is used in conjunction with the tetrapolar electrode configuration to avoid the contact pressure effects at the electrode-skin interface.

The BI sensor can be a Series Model which assumes that there is one conductive path and that the body consists of a series of resistors. An electrical current, injected at a single frequency, is used to measure whole body impedance (i.e., wrist to ankle) for the purpose of estimating total body water and fat free mass. Alternatively, the BI instrument can be a Parallel BI Model In this model of impedance, the resistors and capacitors are oriented both in series and in parallel in the human body. Whole body BI can be used to estimate TBW and FFM in healthy subjects or to estimate intracellular water (ICW) and body cell mass (BCM). High-low BI can be used to estimate extracellular water (ECW) and total body water (TBW). Multi-frequency BI can be used to estimate ECW, ICW, and TBW; to monitor changes in the ECW/BCM and ECW/TBW ratios in clinical populations. The instrument can also be a Segmental BI Model and can be used in the evaluation of regional fluid changes and in monitoring extra cellular water in patients with abnormal fluid distribution, such as those undergoing hemodialysis. Segmental BI can be used to measure fluid distribution or regional fluid accumulation in clinical populations. Upper-body and Lower-body BI can be used to estimate percentage BF in healthy subjects with normal hydration status and fluid distribution. The BI sensor can be used to detect acute dehydration, pulmonary edema (caused by mitral stenosis or left ventricular failure or congestive heart failure, among others), or hyperhydration cause by kidney dialysis, for example. In one embodiment, the system determines the impedance of skin and subcutaneous adipose tissue using tetrapolar and bipolar impedance measurements. In the bipolar arrangement the inner electrodes act both as the electrodes that send the current (outer electrodes in the tetrapolar arrangement) and as receiving electrodes. If the outer two electrodes (electrodes sending current) are superimposed onto the inner electrodes (receiving electrodes) then a bipolar BIA arrangement exists with the same electrodes acting as receiving and sending electrodes. The difference in impedance measurements between the tetrapolar and bipolar arrangement reflects the impedance of skin and subcutaneous fat. The difference between the two impedance measurements represents the combined impedance of skin and subcutaneous tissue at one or more sites. The system determines the resistivities of skin and subcutaneous adipose tissue, and then calculates the skinfold thickness (mainly due to adipose tissue).

Various BI analysis methods can be used in a variety of clinical applications such as to estimate body composition, to determine total body water, to assess compartmentalization of body fluids, to provide cardiac monitoring, measure blood flow, dehydration, blood loss, wound monitoring, ulcer detection and deep vein thrombosis. Other uses for the BI sensor includes detecting and/or monitoring hypovolemia, hemorrhage or blood loss. The impedance measurements can be made sequentially over a period of in time; and the system can determine whether the subject is externally or internally bleeding based on a change in measured impedance. The watch can also report temperature, heat flux, vasodilation and blood pressure along with the BI information.

In one embodiment, the BI system monitors cardiac function using impedance cardiography (ICG) technique. ICG provides a single impedance tracing, from which parameters related to the pump function of the heart, such as cardiac output (CO), are estimated. ICG measures the beat-to-beat changes of thoracic bioimpedance via four dual sensors applied on the neck and thorax in order to calculate stroke volume (SV). By using the resistivity p of blood and the length L of the chest, the impedance change AZ and base impedance (Zo) to the volume change AV of the tissue under measurement can be derived as follows:

$$\Delta V = \rho \frac{L^2}{Z_0^2} \Delta Z$$

In one embodiment, SV is determined as a function of the first derivative of the impedance waveform (dZ/dtmax) and the left ventricular ejection time (LVET)

$$SV = \rho \frac{L^2}{Z_0^2} \left(\frac{dZ}{dt}\right)_{max} LVET$$

In one embodiment, L is approximated to be 17% of the patient's height (H) to yield the following:

$$SV = \left(\frac{(0.17\ H)^3}{4.2}\right) \frac{\left(\frac{dZ}{dt}\right)_{max}}{Z_0} LVET$$

In another embodiment, δ or the actual weight divided by the ideal weight is used:

$$SV = \delta \times \left(\frac{(0.17\ H)^3}{4.2}\right) \frac{\left(\frac{dZ}{dt}\right)_{max}}{Z_0} LVET$$

The impedance cardiographic embodiment allows hemodynamic assessment to be regularly monitored to avoid the occurrence of an acute cardiac episode. The system provides an accurate, noninvasive measurement of cardiac output (CO) monitoring so that ill and surgical patients undergoing major operations such as coronary artery bypass graft (CABG) would benefit. In addition, many patients with chronic and comorbid diseases that ultimately lead to the need for major operations and other costly interventions might benefit from more routine monitoring of CO and its dependent parameters such as systemic vascular resistance (SVR).

Once SV has been determined, CO can be determined according to the following expression: CO=SV*HR, where HR=heart rate. CO can be determined for every heart-beat. Thus, the system can determine SV and CO on a beat-to-beat basis.

In one embodiment to monitor heart failure, an array of BI sensors are place in proximity to the heart. The array of BI sensors detect the presence or absence, or rate of change, or body fluids proximal to the heart. The BI sensors can be supplemented by the EKG sensors. A normal, healthy, heart beats at a regular rate. Irregular heart beats, known as cardiac arrhythmia, on the other hand, may characterize an unhealthy condition. Another unhealthy condition is known as congestive heart failure ("CHF"). CHF, also known as heart failure, is a condition where the heart has inadequate capacity to pump sufficient blood to meet metabolic demand. CHF may be caused by a variety of sources, including, coronary artery disease, myocardial infarction, high blood pressure, heart valve disease, cardiomyopathy, congenital heart disease, endocarditis, myocarditis, and others. Unhealthy heart conditions may be treated using a cardiac rhythm management (CRM) system. Examples of CRM systems, or pulse generator systems, include defibrillators (including implantable cardioverter defibrillator), pacemakers and other cardiac resynchronization devices.

In one implementation, BIA measurements can be made using an array of bipolar or tetrapolar electrodes that deliver a constant alternating current at 50 KHz frequency. Whole body measurements can be done using standard right-sided. The ability of any biological tissue to resist a constant electric current depends on the relative proportions of water and electrolytes it contains, and is called resistivity (in Ohms/cm 3). The measuring of bioimpedance to assess congestive heart failure employs the different bio-electric properties of blood and lung tissue to permit separate assessment of: (a) systemic venous congestion via a low frequency or direct current resistance measurement of the current path through the right ventricle, right atrium, superior vena cava, and subclavian vein, or by computing the real component of impedance at a high frequency, and (b) pulmonary congestion via a high frequency measurement of capacitive impedance of the lung. The resistance is impedance measured using direct current or alternating current (AC) which can flow through capacitors.

In one embodiment, a belt is worn by the patient with a plurality of BI probes positioned around the belt perimeter. The output of the tetrapolar probes is processed using a second-order Newton-Raphson method to estimate the left and right-lung resistivity values in the thoracic geometry. The locations of the electrodes are marked. During the measurements procedure, the belt is worn around the patient's thorax while sitting, and the reference electrode is attached to his waist. The data is collected during tidal respiration to minimize lung resistivity changes due to breathing, and lasts approximately one minute. The process is repeated periodically and the impedance trend is analyzed to detect CHF. Upon detection, the system provides vital parameters to a call center and the call center can refer to a physician for consultation or can call 911 for assistance.

In one embodiment, an array of noninvasive thoracic electrical bioimpedance monitoring probes can be used alone or in conjunction with other techniques such as impedance cardiography (ICG) for early comprehensive cardiovascular assessment and trending of acute trauma victims. This embodiment provides early, continuous cardiovascular assessment to help identify patients whose injuries were so severe that they were not likely to survive. This included severe blood and/or fluid volume deficits induced by trauma, which did not respond readily to expeditious volume resuscitation and vasopressor therapy. One exemplary system monitors cardiorespiratory variables that served as statistically significant measures of treatment outcomes: Qt, BP, pulse oximetry, and transcutaneous Po2 (Ptco2). A high Qt may not be sustainable in the presence of hypovolemia, acute anemia, pre-existing impaired cardiac function, acute myocardial injury, or coronary ischemia. Thus a fall in Ptco2 could also be interpreted as too high a metabolic demand for a patient's cardiovascular reserve. Too high a metabolic demand may compromise other critical organs. Acute lung injury from hypotension, blunt trauma, and massive fluid resuscitation can drastically reduce respiratory reserve.

One embodiment that measures thoracic impedance (a resistive or reactive impedance associated with at least a portion of a thorax of a living organism). The thoracic impedance signal is influenced by the patient's thoracic intravascular fluid tension, heart beat, and breathing (also referred to as "respiration" or "ventilation"). A "de" or "baseline" or "low frequency" component of the thoracic impedance signal (e.g., less than a cutoff value that is approximately between 0.1 Hz and 0.5 Hz, inclusive, such as, for example, a cutoff value of approximately 0.1 Hz) provides information about the subject patient's thoracic fluid tension, and is therefore influenced by intravascular fluid shifts to and away from the thorax. Higher frequency components of the thoracic impedance signal are influenced by the patient's breathing (e.g., approximately between 0.05 Hz and 2.0 Hz inclusive) and heartbeat (e.g., approximately between 0.5 Hz and 10 Hz inclusive). A low intravascular fluid tension in the thorax ("thoracic hypotension") may result from changes in posture. For example, in a person who has been in a recumbent position for some time, approximately ⅓ of the blood volume is in the thorax. When that person then sits upright, approximately ⅓ of the blood that was in the thorax migrates to the lower body. This increases thoracic impedance. Approximately 90% of this fluid shift takes place within 2 to 3 minutes after the person sits upright.

The accelerometer can be used to provide reproducible measurements. Body activity will increase cardiac output and also change the amount of blood in the systemic venous system or lungs. Measurements of congestion may be most reproducible when body activity is at a minimum and the patient is at rest. The use of an accelerometer allows one to sense both body position and body activity. Comparative measurements over time may best be taken under reproducible conditions of body position and activity. Ideally, measurements for the upright position should be compared as among themselves. Likewise measurements in the supine, prone, left lateral decubitus and right lateral decubitus should be compared as among themselves. Other variables can be used to permit reproducible measurements, i.e. variations of the cardiac cycle and variations in the respiratory cycle. The ventricles are at their most compliant during diastole. The end of the diastolic period is marked by the QRS on the electrocardiographic means (EKG) for monitoring the cardiac cycle. The second variable is respiratory variation in impedance, which is used to monitor respiratory rate and volume. As the lungs fill with air during inspiration, impedance increases, and during expiration, impedance decreases. Impedance can be measured during expiration to minimize the effect of breathing on central systemic venous volume. While respiration and CHF both cause variations in impedance, the rates and magnitudes of the impedance variation are different enough to separate out the respiratory variations which have a frequency of about 8 to 60 cycles per minute and congestion changes which take at least several minutes to hours or even days to occur. Also, the magnitude of impedance change is likely to be much greater for congestive changes than for normal respiratory variation. Thus, the system can detect congestive heart failure (CHF) in early stages and alert a patient to prevent disabling and even lethal episodes of CHF. Early treatment can avert progression of the disorder to a dangerous stage.

In an embodiment to monitor wounds such as diabetic related wounds, the conductivity of a region of the patient with a wound or is susceptible to wound formation is monitored by the system. The system determines healing wounds if the impedance and reactance of the wound region increases as the skin region becomes dry. The system detects infected, open, interrupted healing, or draining wounds through lower regional electric impedances. In yet another embodiment, the bioimpedance sensor can be used to determine body fat. In one embodiment, the BI system determines Total Body Water (TBW) which is an estimate of total hydration level, including intracellular and extracellular water; Intracellular Water (ICW) which is an estimate of the water in active tissue and as a percent of a normal range (near 60% of TBW); Extracellular Water (ECW) which is water in tissues and plasma and as a percent of a normal range (near 40% of TBW); Body Cell Mass (BCM) which is an estimate of total pounds/kg of all active cells; Extracellular Tissue (ECT)/Extracellular Mass (ECM) which is an estimate of the mass of all other non-muscle inactive tissues including ligaments, bone and ECW; Fat Free Mass (FFM)/ Lean Body Mass (LBM) which is an estimate of the entire mass that is not fat. It should be available in pounds/kg and may be presented as a percent with a normal range; Fat Mass (FM) which is an estimate of pounds/kg of body fat and percentage body fat; and Phase Angle (PA) which is associated with both nutrition and physical fitness.

In addition to eye mounted sensors, the system can work with wearable sensors, for example devices for sensing ECG, EKG, blood pressure, sugar level, among others. In one embodiment, the sensors are mounted on the patient's wrist (such as a wristwatch sensor) and other convenient anatomical locations. Exemplary sensors 40 include standard medical diagnostics for detecting the body's electrical signals emanating from muscles (EMG and EOG) and brain (EEG) and cardiovascular system (ECG). Leg sensors can include piezoelectric accelerometers designed to give qualitative assessment of limb movement. Additionally, thoracic and abdominal bands used to measure expansion and contraction of the thorax and abdomen respectively. A small sensor can be mounted on the subject's finger in order to detect blood-oxygen levels and pulse rate. Additionally, a microphone can be attached to throat and used in sleep diagnostic recordings for detecting breathing and other noise. One or more position sensors can be used for detecting orientation of body (lying on left side, right side or back) during sleep diagnostic recordings. Each of sensors can individually transmit data to a cloud server using wired or wireless transmission. Alternatively, all sensors 40 can be fed through a common bus into a single transceiver for wired or wireless transmission. The transmission can be done using a magnetic medium such as a floppy disk or a flash memory card, or can be done using infrared or radio network link, among others. The sensor can also include an indoor positioning system or alternatively a global position system (GPS) receiver that relays the position and ambulatory patterns of the patient to the server 20 for mobility tracking.

In one embodiment, the sensors for monitoring vital signs are enclosed in a wrist-watch sized case supported on a wrist band. The sensors can be attached to the back of the case. In another embodiment, EKG/ECG contact points are positioned on the back of the wrist-watch case. In yet another embodiment that provides continuous, beat-to-beat wrist arterial pulse rate measurements, a pressure sensor is housed in a casing with a 'free-floating' plunger as the sensor applanates the radial artery. A strap provides a constant force for effective applanation and ensuring the position of the sensor housing to remain constant after any wrist movements. The change in the electrical signals due to change in pressure is detected as a result of the piezoresistive nature of the sensor are then analyzed to arrive at various arterial pressure, systolic pressure, diastolic pressure, time indices, and other blood pressure parameters.

An embodiment provides a system and a method for rendering augmented/virtual reality content and enabling users to modify the augmented reality content. The system may include one or more image capturing devices through which data from the instant surrounding of the user may be captured. Further, the system may communicate with one or more multimedia content servers to access files from the multimedia content servers. Such files may be stored in a database within the system. Examples of multimedia files may include images, text and icons or moving content such as video clips, among others. The system may render augmented reality content to be displayed to the user by integrating the data captured through the image capturing device and data retrieved from the multimedia servers in the database. The system may include one or more sensors through which input may be provided to a processor. The input may for example include data corresponding to tactile data, gestures data, movement and positional data of the user, among others. Semantics corresponding to such input may be stored in a gesture recognition database. The system may further determine one or more outcomes based on the input received through the sensors. The outcomes corresponding to the input may be stored in the gesture recognition database, which is accessible to the processor. One or more objects of the augmented reality content may be altered by applying the outcomes based on the input to the content that is presented to the user. The augmented reality content may be presented on an augmented/virtual reality display device which may be integrated with the system.

Alternatively, the virtual/augmented reality content may be projected on surfaces such as for example, walls, tables, floors and ceilings, among others. The virtual reality content may be displayed either in two dimensional or three dimensional formats. A rendering module may render the content to be displayed such that, the user may experience the event occurring in a three-dimensional space and interact with the contents of the event.

Another embodiment provides a system for enabling a plurality of users to participate in an activity and communicate in virtual reality. The system may be implemented in a plurality of scenarios where the user of the system, while being engaged in an activity, may be willing to experience the virtual presence of other users, taking part in the same activity, while the activity is in progress. For example, the system may be used in a scenario when the user is performing yoga at home. The user may be willing to experience the virtual presence of one or more of his friends performing yoga beside him. The system may be configured to render virtual content showing virtual images or videos of one or more other users who may or may not be performing yoga. The users may be able to communicate with one another through voice or text or both voice and text. The system may be used in all possible scenarios where virtual interaction may be desired by the user with his/her family, friends or any person whom the user may be interested in interacting virtually. One or more of the other users may be connected to the user on one or more social networking platforms. The system may retrieve information corresponding to the other users, who may be connected to the user on one or more social networking platforms by accessing the user's profile. The system may be configured to render a virtual reality environment based on the type of activity the user may be engaged in. The processor, input units, database, image capturing device may be embedded within the augmented/virtual reality (AR/VR) devices. Each user participating in an activity in virtual reality with one another may interact through their respective AR/VR devices.

The database may include information corresponding to the user's profile as retrieved from one or more social networking platforms. Alternatively, the user may feed data corresponding to his profile in the system, which may be stored in the database. The database may communicate with servers associated with one or more social networking portals and retrieve the user's relationship information with other users on the portal. Profiles of a plurality of users with whom the user may be connected may be stored in the database. Such information may also be fed into the system by the user and may be stored in the database. The system may be configured to generate virtual content based on the user's profile information and profiles of the plurality of users stored in the database. The database may also store preconfigured profiles of users who may not be connected with the user. Such profiles may include profiles of celebrities, animated characters or other profiles or personalities in whom the user may have shown interest. The processor may be configured to access the database and generate content based on the user's preference and profile. The database may store a set of preconfigured or configurable rules that the processor may access to determine the type of content to be rendered based on at least the preference and profile of the user for whom the content is to be displayed.

Figure 3:
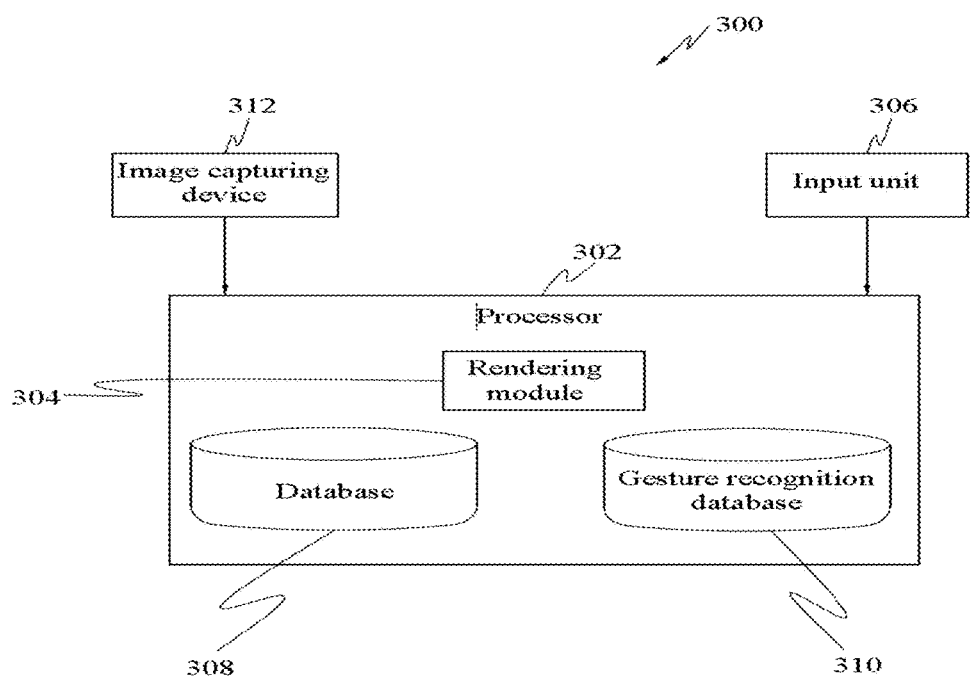
FIG. 3 illustrates a block diagram of a system for displaying virtual reality content to users and enabling users to modify the augmented reality content.

Referring to the figures and more particularly to FIG. 3, an embodiment discloses a system 300 for displaying augmented/virtual reality content to users and enables users to modify the augmented reality content. The system 300 may include a processor 302 and the processor 302 may include a rendering module 304. The system 300 may include one or more input units 306, a database 308 and a gesture recognition database 310. The system 300 may further include one or more image capturing devices 312. Further, the processor 302 may be configured to establish a connection with an AR device. The processor 302 may be embedded into the AR device. The processor 302 may be, for example, a graphics processing unit (GPU).

The AR device may be a device which may be wearable by the user like a goggle or it may be a head mounted device. The AR device may house a projector comprising of lenses that beams images onto the user's eyes creating an optical signal on the retina. The AR goggle may be the display device. The augmented reality content may be projected onto the AR display device. Alternatively, the AR device may project content onto display surfaces. This may be the case when the AR device is a head mounted device.

The system 300 may communicate with one or more multimedia content servers. Data from the multimedia content servers may be accessible to the processor 302. The multimedia content server and the system 300 may communicate with each other using a network module. The network module may be a mobile network, internet or a local area network, among others. The files/data received from the multimedia content servers may be stored in the database 308. The database 308 may be within the processor 302. Alternatively, the database 308 may not be within the processor 302 but data stored in the database 308 may be accessible to the processor 302.

In an embodiment, the multimedia content may be streamed from the multimedia server to the database 308. In another embodiment, the system 300 may download the multimedia content from the multimedia server and store the content in the database 308, thereby enabling the processor 302 to utilize the multimedia content even when it is not connected to the multimedia server.

Figure 4A:
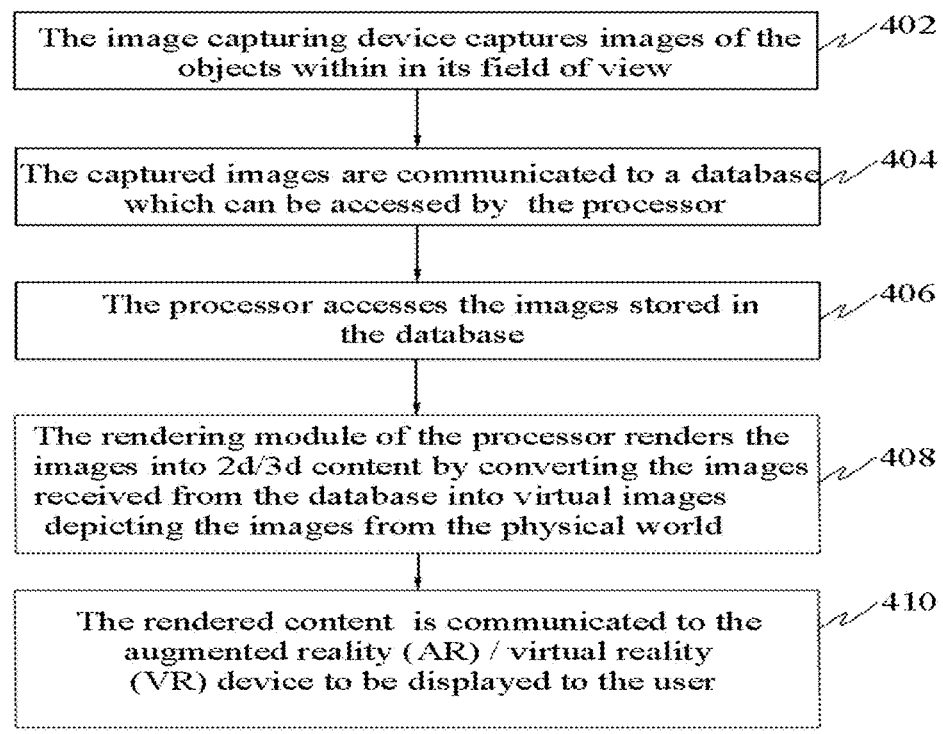
FIGS. 4A-4B are flowcharts illustrating different methods of rendering virtual reality content to be displayed to a user in accordance with an embodiment.

Referring to FIG. 4A, an embodiment discloses a method of rendering content to be displayed to the user, in accordance with an embodiment. At step 402, an image capturing device 312 may capture images of the objects within the field of view of the image capturing device 312. The field of view may include the instant surrounding of the user. The image-capturing device 312 may be a camera or other image sensors and may capture images from the instant surrounding within its field of view. At step 404, the captured images is communicated with the database 308, which can be accessed by the processor 302. At step 406, the processor 302 may access the images stored in the database 308. At step 408, the rendering module 304 of the processor 302 may render the images into two or three-dimensional content by converting the images received from the database into virtual images depicting the images from the instant surrounding of the physical world. The images may be rendered such that the user may see the images in either two or three dimensional formats. At step 410, the rendered content may be communicated to the AR device to be displayed to the user. The AR device may project the virtual content on the AR display device or on one or more display surfaces. This virtual content may be a portion of the entire content such as, the background scenery. The system 300 may further integrate simulated virtual images with the images depicting the instant surrounding and a combined virtual content may be rendered for display to the user. The user may be provided an option to choose content to be integrated with the images of the instant surrounding.

The processor 302 may generate virtual images by accessing the multimedia content. In an embodiment, the AR device may simulate data from the multimedia content and generate images of virtual objects. Such virtual images may be generated based on selection by the user. Virtual content may be generated by integrating the virtual images with the images of the surrounding by simulating the data in time, frequency and space.

Figure 4B:
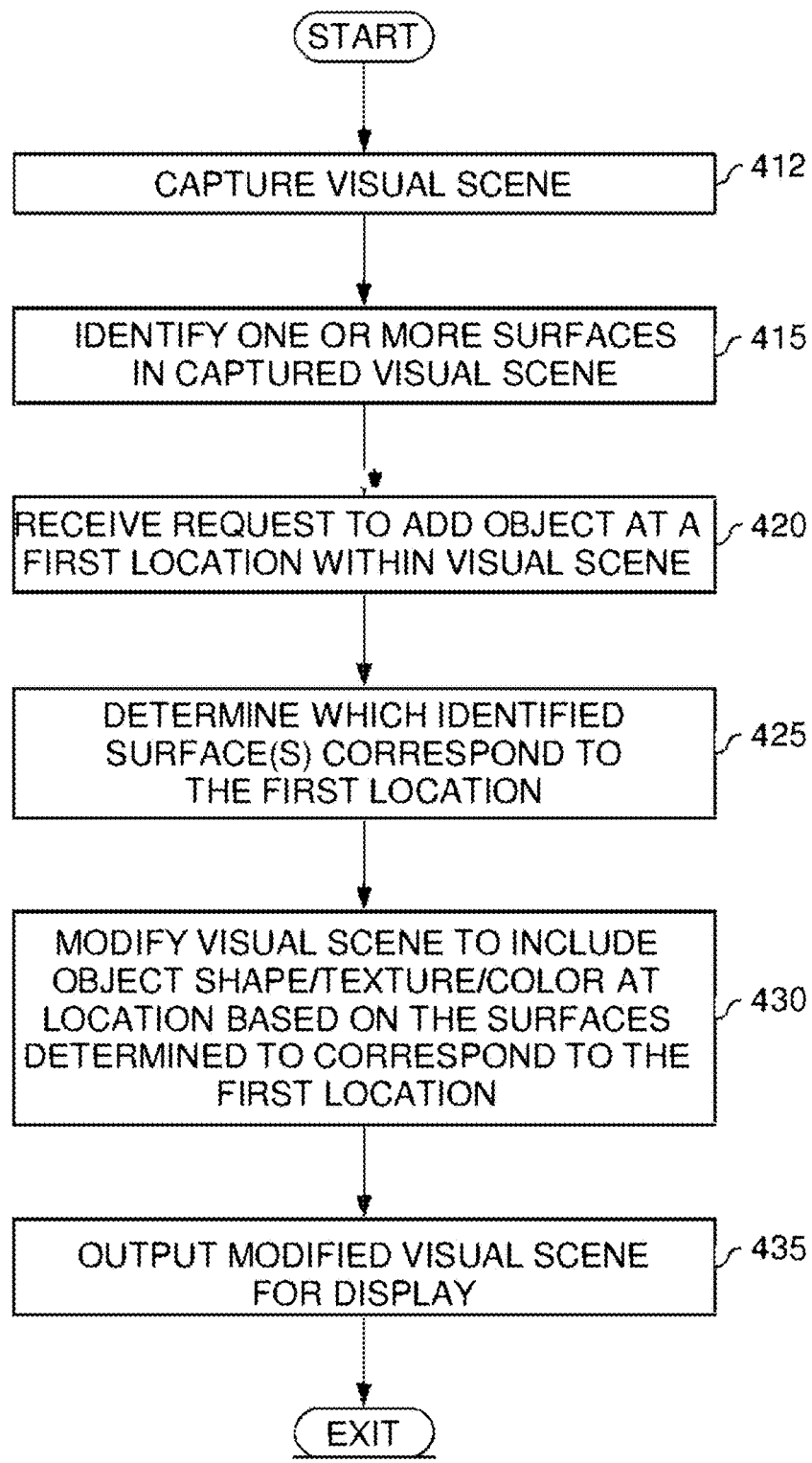

FIG. 4B is a flow diagram illustrating a method for adding new objects and then texturing/painting surfaces within a scene displayed on an augmented reality device, according to one embodiment described herein. As shown, the method begins at step 412, where an augmented reality device captures a visual scene. As discussed above, the visual scene may include a plurality of frames representing a physical, real-world environment and captured using one or more cameras of the augmented reality device. The an object placement component receives an object to be place, and then estimates one or more surfaces of objects within the captured visual scene (step 415). For instance, the placement component could be preconfigured with geometric data (e.g., dimensions information, shape information, etc.) for particular physical objects, and could use this geometric data to determine the surfaces of instances of these particular objects within the captured visual scene. In one embodiment, the placement component is configured to identify the edges of objects within the captured visual scene, and to estimate the three-dimensional surfaces of these objects based on the determined edges.

In the depicted embodiment, the object placement component then receives a request to place and texturize/paint at a first location within the visual scene (step 420). Such a request could be formulated, for instance, based on user interaction with an interface of the augmented reality device. As an example, the object placement component could select a paintbrush icon displayed on the screen of the augmented reality device, and could then draw a freeform shape the user wishes to paint at first location within the scene displayed on the augmented reality device (e.g., using the user's finger to manipulate a touch screen of the augmented reality device). In a particular embodiment, the user may select a predefined virtual object to paint within the visual scene. For instance, the user could select a particular predefined object and could select a location within the visual scene in which to paint the selected predefined object.

In one embodiment, the user may draw the freeform shape using a physical paint brush or other stylus tool. For instance, the augmented reality device could be implemented as a pair of glasses worn by the user and configured to augment the area of the physical environment the user is looking at. As an example, the user could use a physical paint brush in order to paint onto the surface of an object in the physical environment. In such an embodiment, the object placement component could determine that the user is requesting to paint an object within the physical environment when the user touches the paint brush to the surface of the object. The object placement component could track the paint brush's motion (e.g., by analyzing frames captured using a camera of the augmented reality device) and could determine the freeform shape that the user wishes to paint based on the user's movement of the paint brush.

Upon receiving the request to paint within the visual scene at a specified location, the object placement component determines one or more object surfaces associated with the location specified by the request. That is, although the augmented reality device is displaying a two-dimensional image, the displayed two-dimensional image represents a view of a three-dimensional augmented reality space. As such, the object placement component determines which surface(s) of the three-dimensional objects in the three-dimensional augmented reality space correspond to the specified location of the two-dimensional displayed image displayed on the augmented reality device.

The object placement component then paints the determined surfaces as specified in the request (step 430). In one embodiment, the object placement component could recolor the surface of an object within the augmented reality space based on the user request. For instance, an interface of the augmented reality device could select a color and could use a fill tool to select a surface within the augmented reality scene to paint the selected color. In one embodiment, the user could select a freeform drawing tool and could use this tool to manually color in the surface of an object. In such an embodiment, the object placement component could be configured to detect when the user's freeform drawing covers more than a threshold amount of an object's surface and, if so, could determine that the user intends to paint the entire surface of the object in the specified color. The object placement component could then paint the surface accordingly. As another example, the object placement component could project a drawing (e.g., a freeform drawing or a predefined drawing selected by the user) onto the surface of an object. The modified visual scene including the painted objects is then output for display (step 435), and the method ends.

As discussed above, because the object placement component is configured to place the object and paint the surfaces of three-dimensional objects within the augmented reality space, rather than to paint at the specified fixed location within the displayed two-dimensional scene, the painted surfaces may persist even when the objects are viewed from different perspectives using the augmented reality device. Thus, for example, although the painted objects may appear as having a different shape from viewed from certain perspectives (e.g., a coffee cup viewed from the side versus the same coffee cup viewed from above), or a different size when viewed from some perspectives (e.g., the same coffee cup when viewed up close versus far away), the objects will remain painted in the specified fashion. Additionally, the painted surface may be partially or completely occluded by other objects when viewed from other perspectives, but may still remain painted in the specified fashion when once again viewed from a perspective where all or part of the surface can be seen. Advantageously, doing so provides a more realistic augmented reality experience for users of the augmented reality device, as painted objects will appear as painted regardless of the angle from which the user views the objects using the augmented reality device.

Figure 4C:
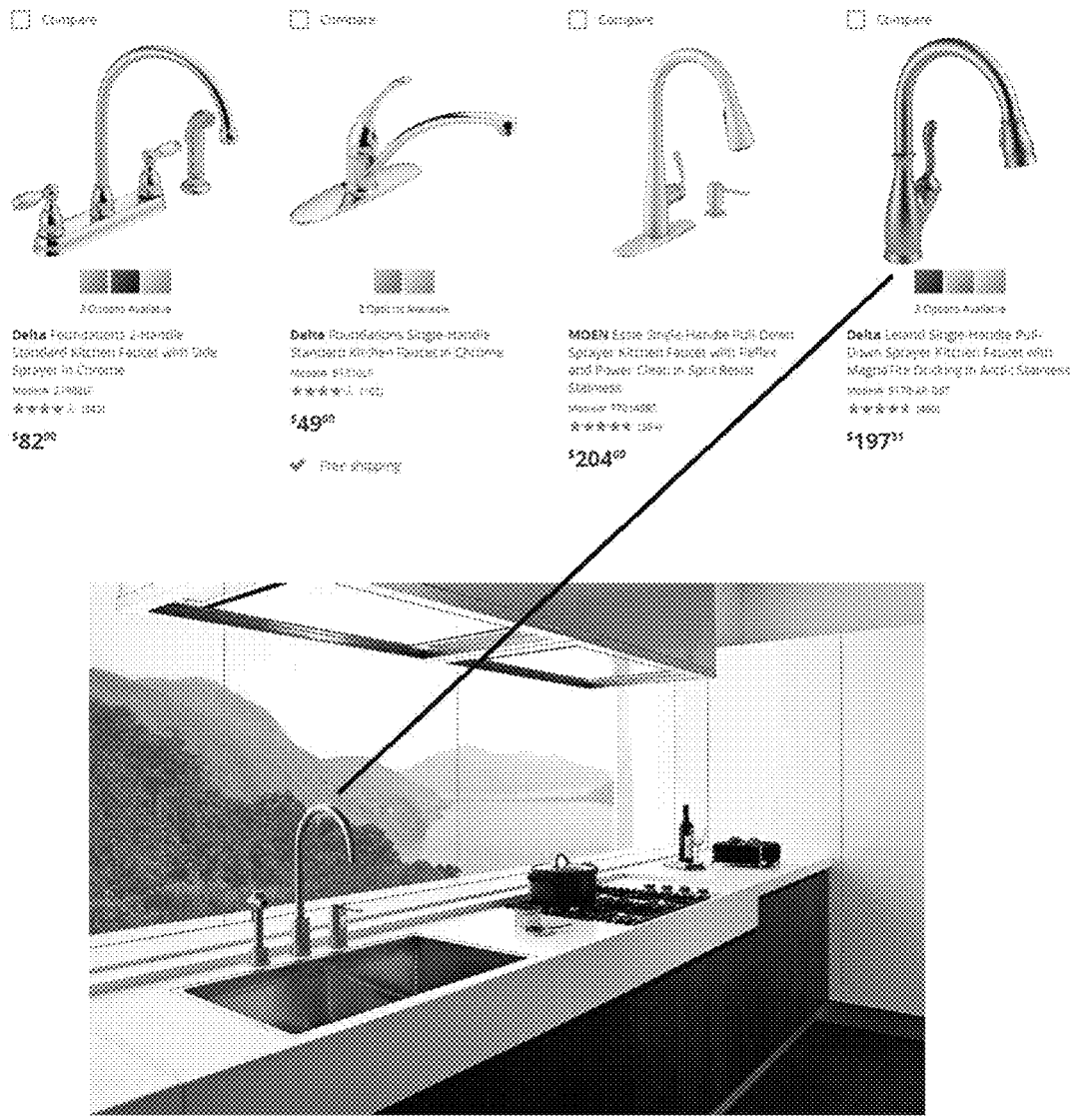
FIG. 4C shows an exemplary AR user interface where the user shops online for a faucet and the system displays the new faucet augmented with the existing kitchen environment.

FIG. 4C shows an exemplary AR user interface where the user shops online for a faucet and the system displays the new faucet augmented with the existing kitchen environment. In this example, the user or the contractor goes on line to select one or more products. The system downloads the images, and searches the seller site using an API to determine if a 3D model is available. If so, the system downloads the 3D models and superimposes the 3D model with the environment and renders the augmented view with the products in proper dimension and position. If the 3D model is not available, the system converts the image into a 3D model using image based 3D modeling software. In one embodiment, insight3D available at http://insight3d.sourceforge.net/ can be used on a series of photos of a real scene (e.g., of a building), and the system automatically matches them and then calculates positions in space from which each photo has been taken (plus camera's optical parameters) along with a 3D pointcloud of the scene. Insight3d's modeling tools can create textured polygonal model. Other 3d generators such as Autodesk 123d Catch can be used as well.

With the 3D model, the system can perform the following:

capturing a view of a facility and selecting a place to insert the 3D model;

overlaying the 3D model with the view of the facility in a mashed-up and aligned manner wherein the 3D model view is displayed contemporaneously and contiguously to form an augmented reality view; and enabling user interaction with the displayed 3D model view to update the 3D model of the facility in the 3D modeling system.

Figure 5:
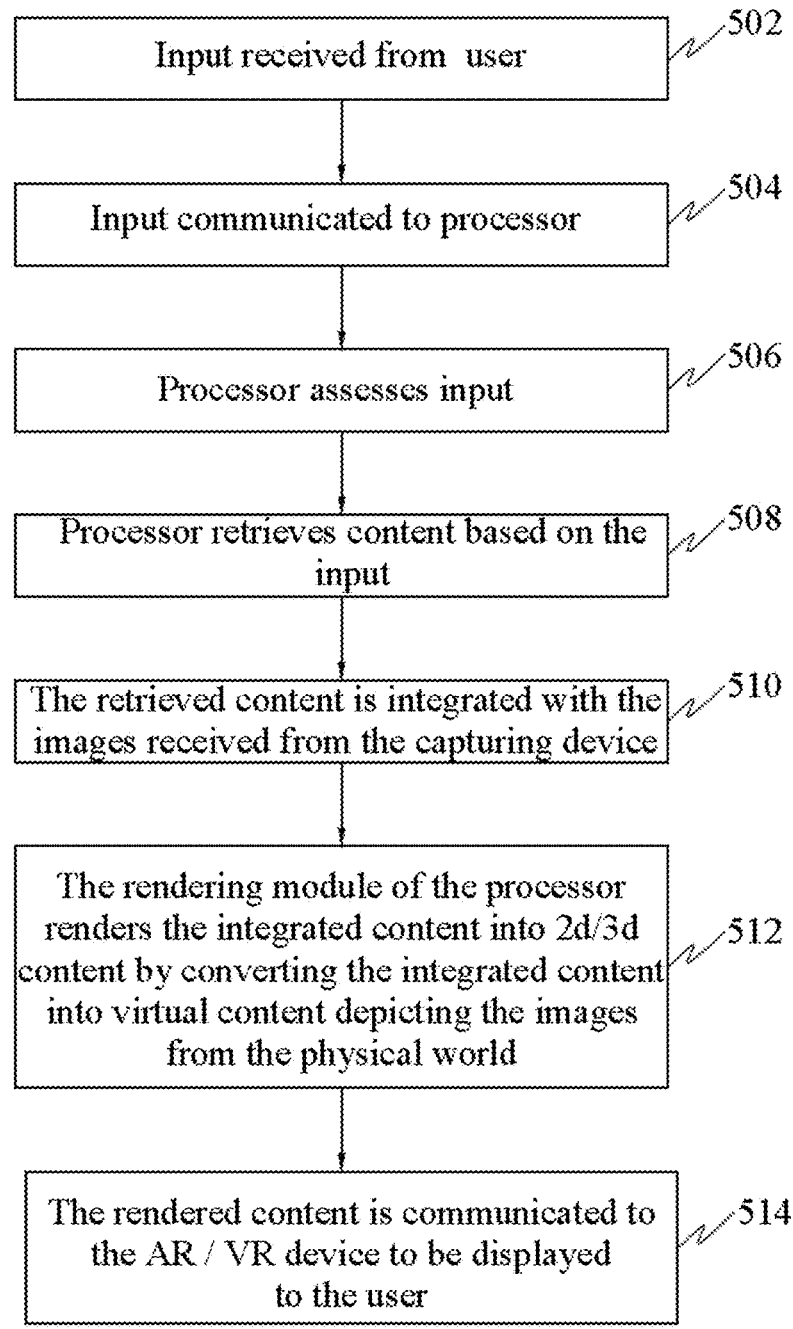
FIG. 5 is a flowchart illustrating the method of rendering virtual reality content to be displayed to the user, based on the input provided by the user.

FIG. 5 is a flowchart illustrating the method of rendering virtual reality content to be displayed to the user, based on the input provided by the user, in accordance with an embodiment. At step 502, the system 300 may receive input from the user. Such input may be information corresponding to what type of content the user is interested in viewing. The input may be provided through a physical keypad, which may be connected to the system 300 or a virtual keypad that the system 300 provides to the user. Alternatively, such input may also be provided by the user by touching or tapping options being provided to the user on a display interface. Such input may also be provided through voice. At step 504, the input received at the previous step may be communicated to the processor 302. At step 506, the processor 302 may assess the input. At step 508, the processor 302 may retrieve content based on the input. The content may be retrieved by accessing the multimedia servers or the database 308. At step 510, the retrieved content may be integrated with the images received from the image-capturing device 312. For this purpose, the processor 302 may determine interest points, define interest operators and construct an optical flow of the images of the instant environment captured through the image capturing device 312. The instant surrounding's pixel coordinates may be determined from the data obtained by processing the image. The processor 302, upon receiving input from users about the type or theme of the content to be rendered, may generate the image and, subsequently, determine the interest points, define interest operators and construct an optical flow of the virtual images that may be retrieved from the multimedia content. At step 512, the rendering module 304 of the processor 302 may render the integrated content into two or three dimensional content by integrating the content depicting the images from the physical world. At step 514, the rendered content may be communicated to the AR device to be displayed to the user. The AR device may display the content on the AR display device or a surface such as a wall, floor, table and ceilings, among others. The display surface may depend on the type of AR device. For example, if the AR device is a device worn like an eyewear, the display may be on the AR device's display surface. If the AR device is a head mounted device, then the display surface may be one or more of the display surfaces mentioned above. The processor 302 may be a self learning artificially intelligent processor to determine the type of content to be presented to the user. The processor 302 may learn from previous activities or selections made by the user and take into consideration such information while generating the content including the virtual images to be integrated with the images of the surroundings.

The sensors may receive inputs corresponding to parameters indicating a set of defined user characteristics. Characteristics may, for example, include head movement speed, head movement acceleration, and/or relationship between head movement and eye movement (e.g., ratio of one to the other), limb movement speed. The characteristics may even include indications of the tendency of a user to pay attention to certain virtual objects such as virtual object type (e.g., text, charts), movement of a virtual object (e.g., large shifts from image to image, fast or rapid movement, direction of movement), and characteristics of the virtual object (e.g., color, brightness, size), among others.

The user's eye and head movements and changes in position may be constantly monitored for displaying virtual content. A sensor, such as a position sensor may be integrated in the AR device which may be configured to monitor the viewer's (user) head and eye positions. The position information may be constantly communicated to the processor 302 and stored in the database 308. The processor 302 may determine the direction of light entering into the eye depending on the eye position. The line of sight may also be determined based on the eye position. The virtual content may be displayed to the user, based on the line of sight of the user.

Figure 6:
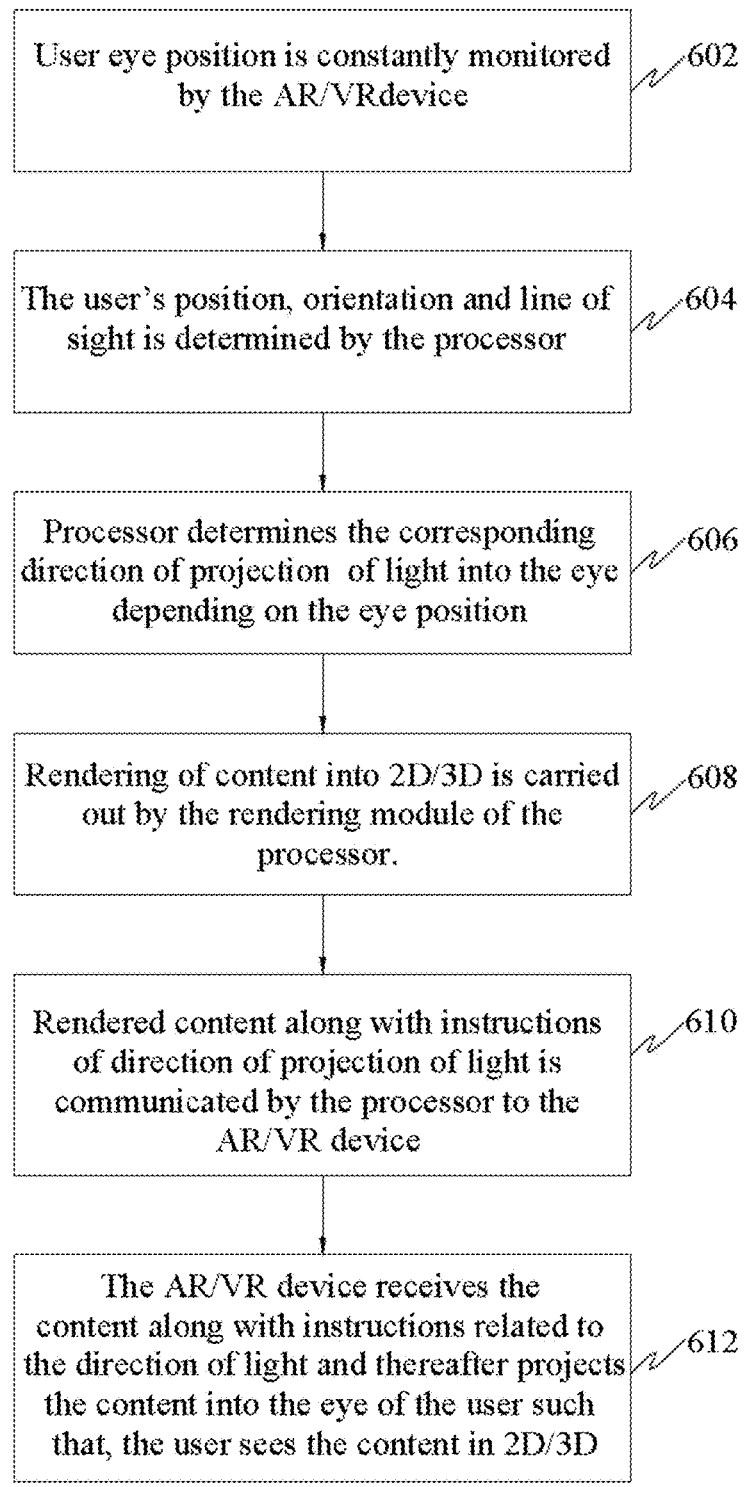
FIG. 6 is a flowchart illustrating the method of displaying virtual reality content to the user, in accordance with an embodiment.

FIG. 6 is a flowchart illustrating the method of displaying virtual reality content to the user, in accordance with an embodiment. At step 602, the user's eye position may be constantly monitored by the augmented reality device. At step 604, the information relating to the eye position may be constantly communicated to the processor 302. Such information may include how fast the eye movement changes, the position of the eye for each change and the line of sight, among others. Such information may be stored in the database 308 and retrieved by the processor 302 to determine the instantaneous velocity at which the eye may move. At step 606, the processor 302 may determine the corresponding direction of projection of light into the eye depending on the eye position. The determined direction of projection of light into the eye depending on the eye position may be stored in the database 308 for the processor 302 to retrieve in future. At step 608, the rendering module 304 of the processor 302 may carry out rendering of content into two or three-dimensional formats. At step 610, the processor 302 may communicate the rendered content, along with instructions of direction of projection of light to the AR device. At step 612, the AR device may receive the content along with instructions related to the direction of projection of light and thereafter project the content into the eye of the user such that, the user sees the content in two or three-dimensional formats. The processor 302 may further determine the velocity at which frames of images may be rendered based on the user's eye position. The processor 302 may estimate an instantaneous velocity at which the eye position changes and the information relating to the velocity may be communicated to the rendering module 304, such that images may be presented as continuous scene according to change in position of the eye.

Figure 7:
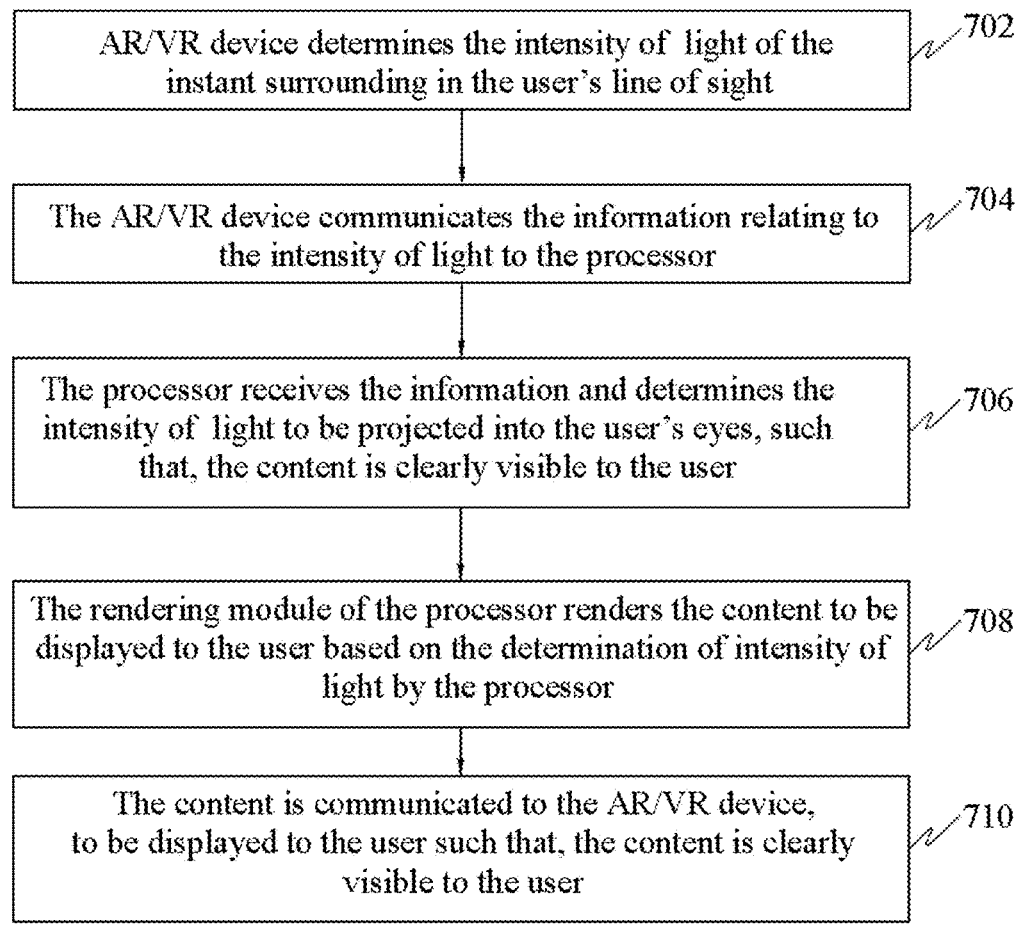
FIG. 7 is a flowchart illustrating the method of displaying virtual reality content to the user, such that the content is clearly visible to the user, in accordance with an embodiment.

Referring to FIG. 7, a method of displaying virtual reality content to the user, such that the content is clearly visible to the user, is illustrated. At step 702, the AR device may determine the intensity of light of the instant surrounding in the user's line of sight. At step 704, the AR device may communicate the information relating to the intensity of light to the processor 302. Such information may include information corresponding to ambient lighting of the environment, brightness of the objects and foreground and background lighting, among others. At step 706, the processor 302 may receive the information and determines the intensity of light to be projected into the user's eyes, such that, the content is clearly visible to the user. For example, the processor 302 may determine the intensity of light to be projected into the user's eye such that the user is clearly able to view an image of the surrounding, depending on the amount of brightness or darkness of the instant surrounding. The processor 302 may define areas of brightness and darkness in a scene and accordingly execute image correction algorithms and apply it on the images to be rendered. At step 708, the rendering module 304 of the processor 302 may render the content to be displayed to the user based on the determination of intensity of light by the processor 302. At step 710, the content may be communicated to the AR device, to be displayed to the user such that, the content is clearly visible to the user.

One or more sensors may receive input such as, tactile and gesture input, data indicating pressure and force vectors, applied through the user's limbs, among others. In an embodiment, the processor 302 may further receive voice data from the one or more sensors such as a microphone. This may be voice input provided by the user, wherein the voice input may correspond to a command. The processor 302 may be configured to receive input from the sensors and synthesize the input and derive the visual output or outcome based on the input. The derived visual output may be applied to the virtual images to alter one or more parameters (location, size etc) of the objects in the image. For example, in a car racing game, the input may correspond to pitch, yaw or roll data of a user's limbs. The user may change the position of the hands to steer a vehicle in the game, thereby altering the pitch, yaw or roll values of the hands. The processor 302 may determine the outcomes of the pitch, yaw and roll data and their effect on the content. The outcome, for example, may be, steering the vehicle to the left or right, or increasing or decreasing the speed of the vehicle.

In an embodiment, the gesture recognition database 310 may store gestures along with the semantics of each gesture received through the sensors. The semantics of the gestures may be predefined and stored in the gesture recognition database 310. The gesture recognition database 310 may also store outcomes of such input. The outcomes may indicate one or more physical actions carried by the user which may be applied to the virtual content to modify or alter parameters of the content. For example, if the user were to provide a gesture indicating expanding or zooming a particular object which is displayed to the user, the outcome would be zooming of the object. The gesture can be the action of zooming with his fingers. The system 300 may receive the input and accesses the gesture recognition database 310 to determine the outcome of the gesture input. The rendering module 304 may receive the outcome of the gesture input and render it in real time to the virtual content in order to alter details of the content. The gesture inputs may for example imply, resizing, adding, deleting, and shifting one or more items or objects of the content from one location to another. Gesture input may not only be limited to gestures made with fingers or hand, such input may also include tactile input, voice input and movement data of the user, among others.

Figure 8A:
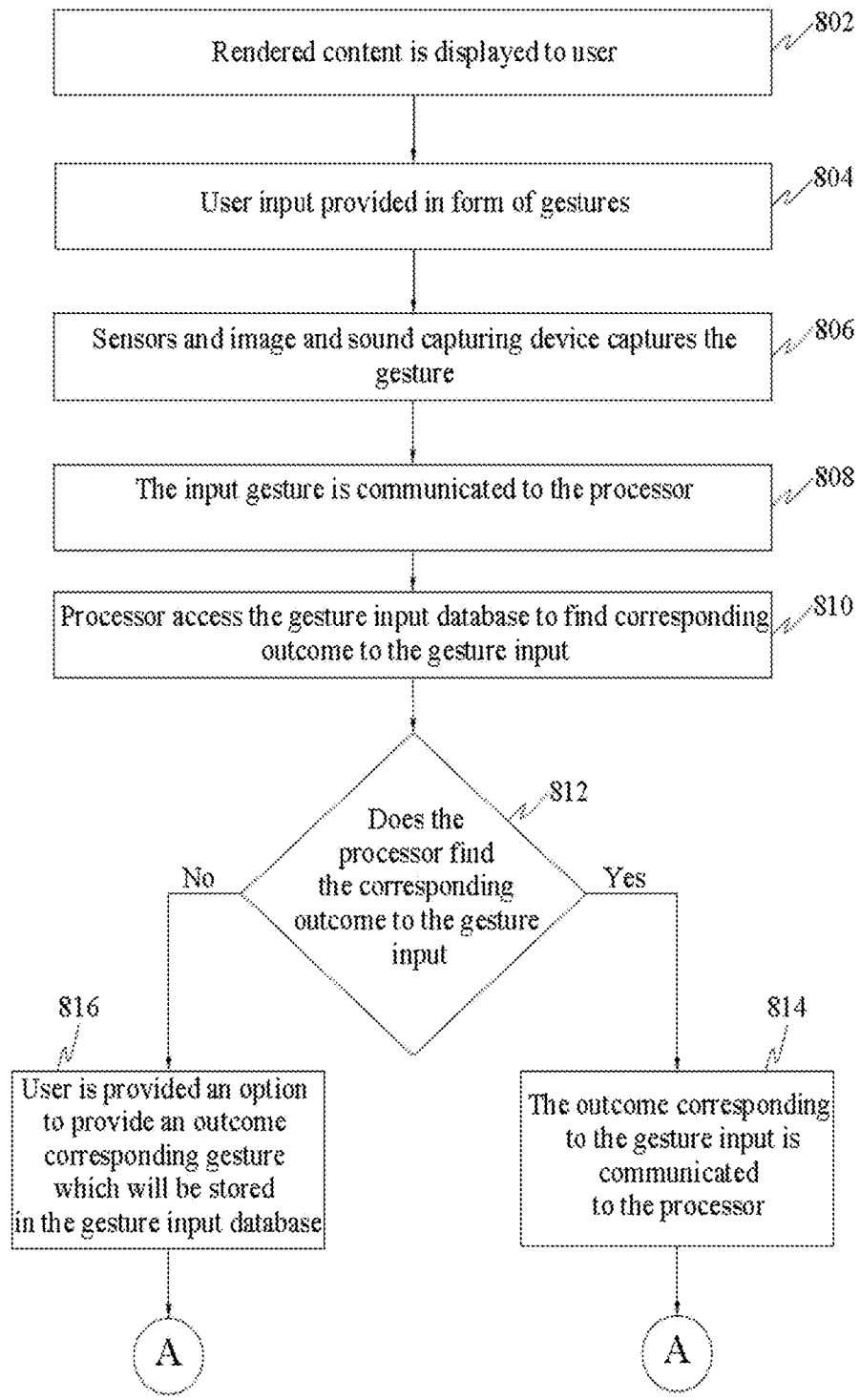
FIGS. 8A-8B is a flowchart illustrating the method of receiving gesture input from the user and thereafter rendering content to be displayed to the user, based on the gesture input, in accordance with an embodiment.
Figure 8B:
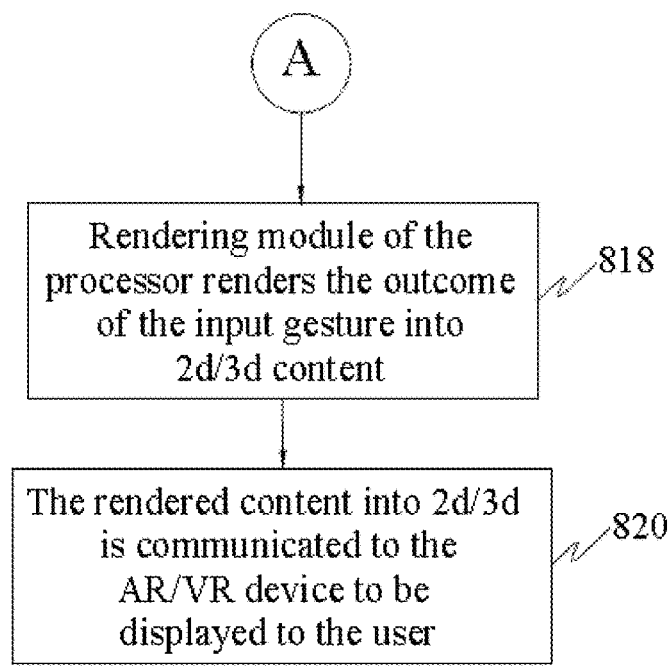

FIGS. 8A-8B is a flowchart illustrating the method of receiving gesture input from the user and thereafter rendering content to be displayed to the user, based on the gesture input, in accordance with an embodiment. At step 802, rendered content may be displayed to user. This rendered content may include the image of the instant surrounding combined with the images of virtual objects. At step 804, user input may be provided in form of gestures. At step 806, sensors and image or sound capturing device may capture the gesture. The image-capturing device 312 may be the image-capturing device that may be implemented to capture gestures. Sound may be captured through one or more microphones. These devices may be the parts of the input unit 306. These devices may be integrated into the system 300 or may be peripheral devices connected to the system 300. Such devices may be detachable from the system 300. At step 808, the input gesture may be communicated to the processor 302. The processor 302 may communicate with the gesture recognition database 310 to find the semantics of such input and derive an outcome corresponding to the input. At step 810, the processor 302 may access the gesture recognition database 310 to determine corresponding outcome to the gesture input. At step 812, the processor 302 may find the corresponding outcome to the gesture input. If the processor 302 is able to find the outcome corresponding to the gesture input, then at step 814, the outcome corresponding to the gesture input may be communicated to the processor 302. If the processor 302 is not able to find the outcome corresponding to the gesture input at step 812, then at step 816, the user may be provided an option to provide an outcome corresponding gesture which will be stored in the gesture recognition database 310. The user may provide outcome corresponding to the gestures through virtual keypads that may be displayed to the user. The user may also provide such input through a physical keypad connected to the system 300. At step 818, the rendering module 304 of the processor 302 may render the outcome of the input gesture into the two or three dimensional augmented reality content. At step 820, the rendered content may be communicated to the AR device to be displayed to the user. The outcome of the gestures may be used to alter, edit, add or delete one or more content in the images that are presented as the augmented reality content. The corresponding outcome may define one or more physical activities performed by the user such as, pointing at some object, moving an object, scrolling, deleting an object, adding objects, walking in virtual reality and speaking, among others. Some or all of the virtual reality content may get altered based on the input provided by the user.

As an example, the rendering module 304 may render the image of a desktop in either 2 dimensional or 3 dimensional form. The user may have set a password for one particular file on the actual desktop. The user may be currently viewing the desktop in virtual reality and the password protected file needs to be unlocked. The user may use the virtual keypad to enter input mapping to the password which may result in unlocking the file on the virtual as well as actual desktop. In another example, the user may be enabled to unlock a programme or show on a television in virtual reality. The system 300 may also enable locking and unlocking of physical or mechanical locks to virtual doors, gates and cars, among others. For example, a door may be rendered in virtual reality and the user may be required to walk through the door which is locked using a mechanical lock. The user may make gestures in space. The gesture may be communicated to the processor 302 to determine the outcome that may imply an unlocking action. The outcome may be rendered to the virtual reality content, thereby allowing the user to unlock the door.

In another example, the system 300 may display a virtual desktop. The files in the desktop may be arranged and displayed on the left side of the desktop. The user may require moving a file from the left hand side of the virtual desktop to the right hand side or to the taskbar of the virtual desktop. The user may use the physical or virtual keypad to enter inputs to the content that may be used to alter the file location on the virtual desktop. Alternatively, user may provide a gesture indicating moving the file from the left hand side to the right hand side. The gesture input may be communicated to the processor 302 through the motion sensors. The processor 302 may determine the outcome of the gesture and communicate the implication of the outcome to the rendering module 304. The rendering module 304 may render the implication and display the change in the virtual content by moving the file from the original position to the desired position.

In yet another example, the user may be enabled to alter content in a virtual football game. The user may be required to run and kick the ball by moving his feet in space to score goals. Pressure sensors may communicate the pressure and force applied by the user's feet. The user may be required to provide an input indicating forwarding the ball to another player. The motion, force and pressure vectors may be taken into account to determine the direction and force at which the ball may move. The output data corresponding to movements of the user's limbs may be rendered on the display. Whether a goal is being scored or whether the user has made a successful pass to another player may be rendered on the virtual reality content display based on the user's inputs.

In an alternate embodiment, the processor 302 may be configured to receive input from the virtual or physical keypad to alter or modify one or more details or objects of the virtual reality content.

Figure 9:
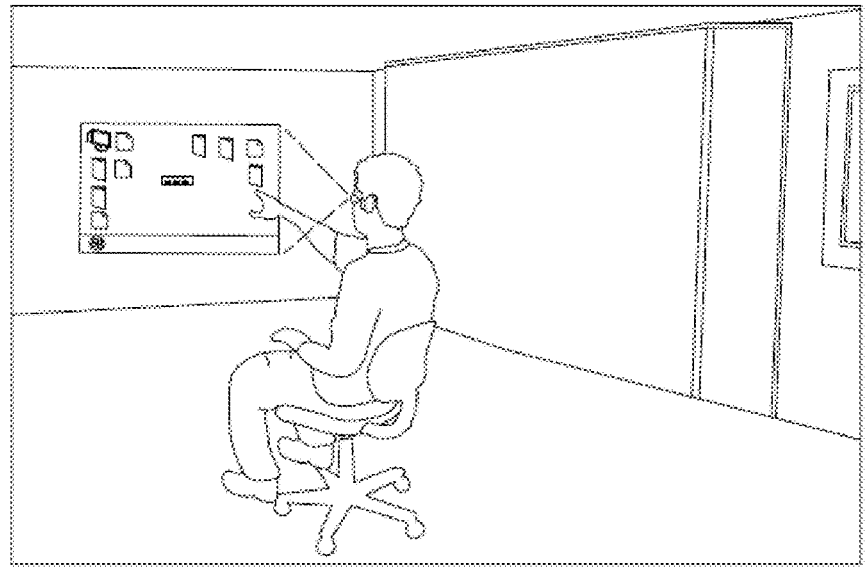
FIG. 9 is an illustration of the virtual reality content being altered by the outcome of a gesture input, in accordance with an embodiment.

FIG. 9 is an illustration of the virtual reality content being altered by the outcome of a gesture input, in accordance with an embodiment. The virtual content is being displayed to the user. The user may wish to view a particular object in the content by expanding the dimensions of the virtual object. The user may provide gesture with his fingers, which may correspond to expand. The portion of the content may be altered by rendering the outcome of the corresponding gesture.

In an embodiment, the depth of field of the user's eye may be calculated based on the eye movement and positions. The rendering module 304 may be configured to render the content into one or more resolutions to enable highlighting certain aspects of the content compared to other aspects of the content. For example, the content in the foreground may be of higher resolution compared to the content in the background. This may enable the user to have a more realistic view of the content, wherein objects nearer to the user are more pronounced in the visibility compared to objects which are farther from the user. The measure of depth of field may and the content being rendered based on the measurement may be applicable in enabling a user to view content in either two or three dimensional formats.

In an embodiment, the field of view of the user's eye may also be calculated based on the eye movement and positions. The field of view may be used to determine the extent to which the user may view the instant surrounding at any given instant.

Figure 10:
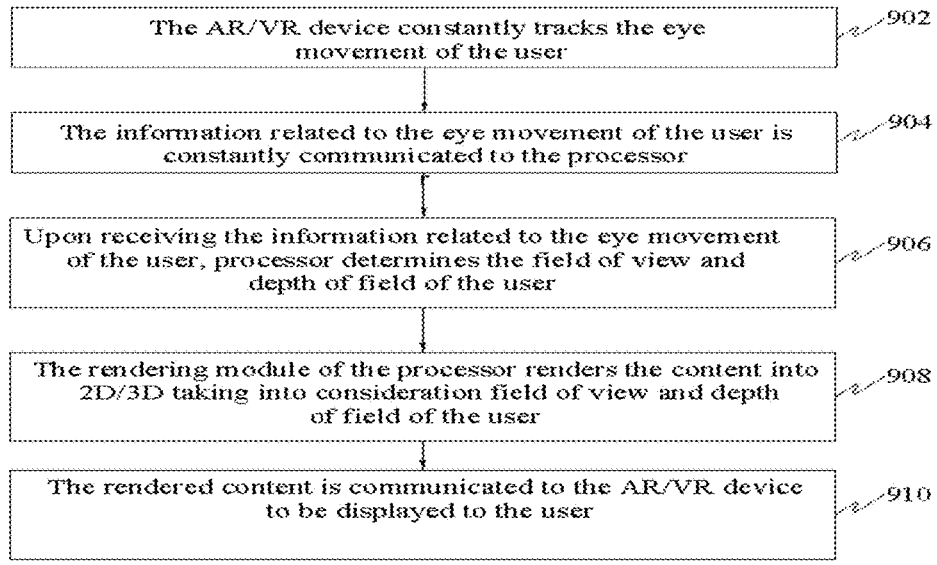
FIG. 10 is a flowchart illustrating the method of displaying virtual reality content to the user considering the field of view and depth of field of the user, in accordance with an embodiment.

FIG. 10 is a flowchart illustrating the method of displaying virtual reality content to the user considering the field of view and depth of field of the user, in accordance with an embodiment. At step 902, the AR device may constantly track the eye movement of the user. At step 904, the information related to the eye movement of the user may be constantly communicated to the processor 302. Such information may include how fast or slow the user' eye may move and change its position and line of sight, among others. Upon receiving the information related to the eye movement of the user, at step 906, the processor 302 may determine the field of view and depth of field of the user's eye. At step 908, the rendering module 304 of the processor 302 may render the content into two or three-dimensional formats taking into consideration field of view and depth of field of the user. At step 910, the rendered content may be communicated to the AR device to be displayed to the user. The user's head position may be constantly changing and the eye position may change relative to the movement of the head. The field of view of the user's eye may be calculated based on the line of sight and the position of the eye. Additionally, the horizontal and vertical field of view of the image-capturing device 312 or the focal length of the image-capturing device 312 may be measured to calculate the field of view of the user's eye.

Further, the rendering module 304 of the processor 302 may render the virtual reality content based on the user's position and orientation. The rendering module 304 may receive from the processor 302 data corresponding to the user's position and orientation. The processor may include pre-configured set of rules pertaining to the user's preferences of the format of display based on the user's position and orientation.

Figure 11:
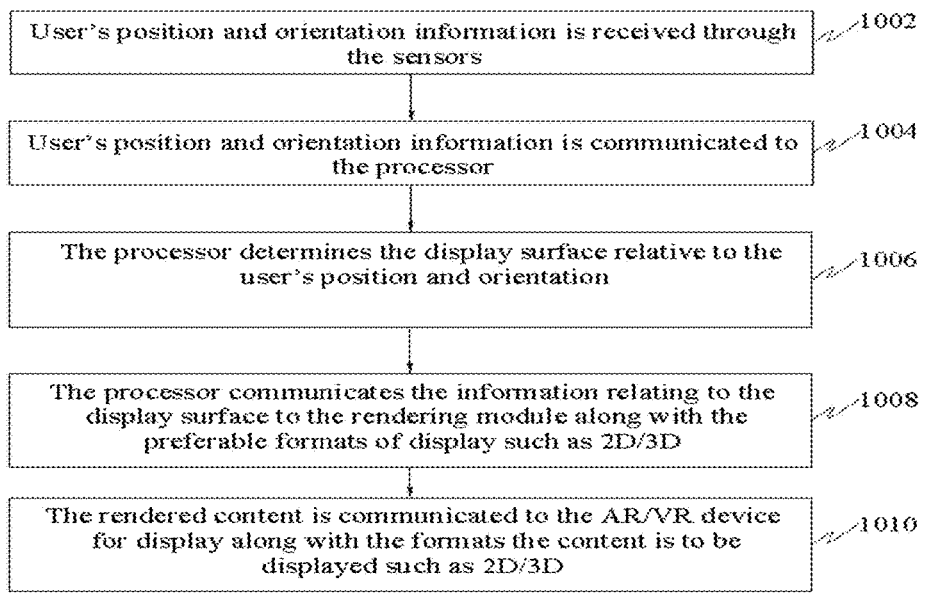
FIG. 11 is a flowchart illustrating the method of rendering virtual reality content based on the display surface, in accordance with an embodiment.

FIG. 11 is a flowchart illustrating the method of rendering virtual reality content based on the display surface, in accordance with an embodiment. At step 1002, the user's position and orientation information may be received through the sensors. At step 1004, the user's position and orientation information may be communicated to the processor 302. Such information may include information corresponding to a user's position such as sitting, standing, walking and lying in a horizontal position, among others. At step 1006, the processor 302 determines the display surface relative to the user's position and orientation. At step 1008, the processor 302 may communicate the information relating to the display surface to the rendering module 304 along with the preferable formats of display such as two or three-dimensional formats. At step 1010, the rendered content may be communicated to the AR device for display along with the formats the content to be displayed.

Displays may be presented to the user based on the user's position and orientation, in accordance with an embodiment. As an example, the user may be presented a holographic display interface based on the position and orientation. Users may be provided options to choose interfaces based on preference, location and orientation, among others. For example, one interface could be displayed while the user is working or taking part in a conference or event, another interface could be displayed while the user is participating in a leisurely activity such as a game. Furthermore, another interface could be displayed while the user is sitting on a couch and watching a movie. Each of these display interfaces may be different from one another. Each of these display interfaces may be configured to display virtual reality content based on the user's position data, movement data, orientation of head and eyes and orientation of limbs, among others.

Further, the display interfaces may be changed for the user based on the theme of the content being displayed. For example, when the user is watching a movie on Netflix, the display interface may be different from the display interface that is presented while the user is watching sports on ESPN. For example, while watching ESPN posters of players or advertisements may be rendered for display on blank walls.

The processor 302 may be a self learning artificially intelligent processor to determine the format of display to be presented, based on the user's position and orientation. Upon rendering the content based on the user's position and orientation, the virtual reality content may be communicated to the VR device to be displayed on the display surface. As an example, if the user is sitting on a couch and the head is tilted towards the right, the display may also be tilted relative to the position of the head. Further, relative to the overall orientation of the user's body, the display surface may be selected by the system 300, such as, wall, ceiling and floor, among others. Furthermore, the display may be a curved display of a straight display. The virtual reality content may be rendered to be displayed on curved display surfaces. The virtual reality content or at least a portion of the content may be remapped such that the virtual reality content may be displayed on curved display surfaces. The rendering module 304 may remap the virtual reality content and render the content to be displayed on curved surfaces.

The rendering module 304 may render two dimensional or three dimensional visual content for display based on the user's position and orientation data. The virtual reality content may, as an example, also be displayed or projected in space as holographic display.

Figure 12:
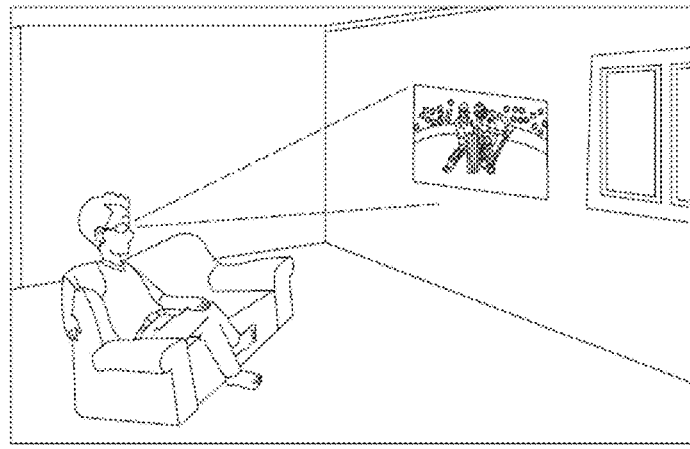
FIG. 12 illustrates display interfaces which may be presented to the user based on the user's position and orientation, in accordance with an embodiment.

Referring to FIG. 12, in another embodiment the system 300 may enable a plurality of users to participate in an activity and communicate, in virtual reality. The system 300 may include a communication module 1202. The system 300 may be configured to communicate with one or more remote servers 1204 via the communication module 1202. The system 300 may be located on a server which may not be located on the VR device and the system 300 may be configured to communicate with the VR device. Alternatively, the system 300 may be located on the VR device. The VR device may project the virtual content based on the instructions received from the processor 302. The virtual content may be images of other users or videos of other users. The system 300 may include one or more image capturing devices. The rendering module 304 may be configured to render virtual content in one or more formats upon receiving instruction from the processor 302.

In an embodiment, the system 300 may be configured to communicate with one or more servers 1204 to retrieve user information. The communication module 1202 may enable the system 300 to communicate with the servers 1204. The communication module 1202 may also enable communication of data from the processor 302 to the AR device. The processor 302 may be configured to store information retrieved from the server 1204 in the database 308. The stored information may be information corresponding to the user's profile, relationship information with other users on one or more social networking platforms and one or more activities the user may be performing, among others. Based on the data stored, the processor 302 may generate lists of preconfigured themes that may represent the activities of the user. The user may be provided an option to select one or more themes depending on the type of the activity, the user may be indulged in. Such lists may be provided to the user on a virtual interface such that the user may select one or more options from the lists.

Figure 13A:
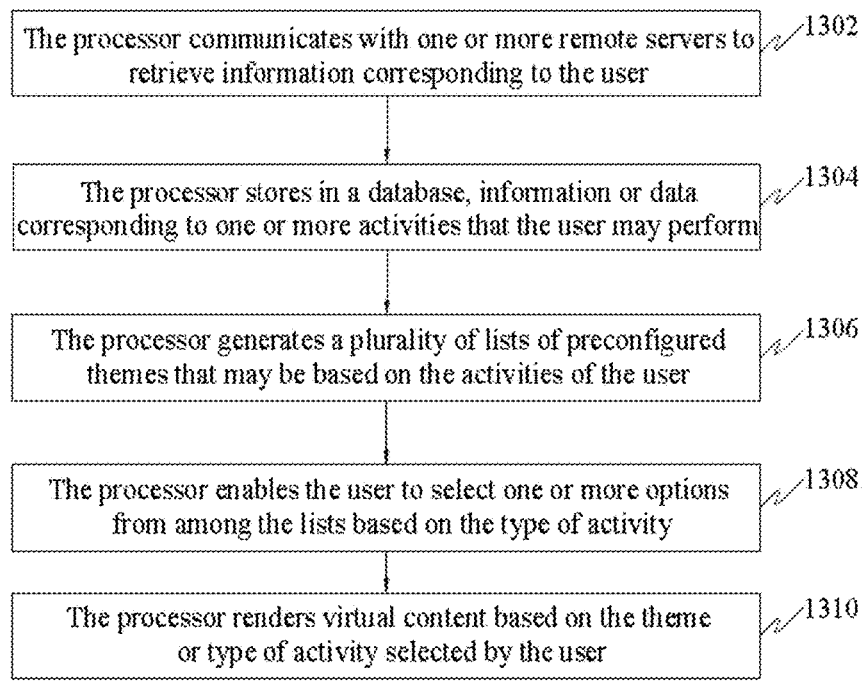
FIG. 13A is a flowchart illustrating the method of rendering virtual content based on the theme or the type of activity a user may be performing, in accordance with an embodiment.

FIG. 13A is a flowchart illustrating the method of rendering virtual content based on the theme or the type of activity the user may be performing, in accordance with an embodiment. At step 1302, the processor 302 may communicate with one or more remote servers 1204 to retrieve information corresponding to the user. At step 1304, the processor 302 may store in the database 308, information or data corresponding to one or more activities that the user may perform. At step 1306, the processor 302 may generate a plurality of lists of preconfigured themes that may be based on the activities. At step 1308, the processor 302 may enable the user to select one or more options from among the lists of themes, which may be based on the type of activity the user may be involved in. At step 1310, the processor 302 may render virtual content based on the theme or type of activity selected by the first user.

Further, a set of machine learning algorithms may enable the processor 302 to learn from the previous choices of theme for an activity selected by the user and thereby automatically select themes based on the activity of the user. Machine learning algorithms may be stored in the database 308 and accessed by the processor 302. Upon selecting the theme, content may be rendered into virtual reality. Further, the user may be required to provide necessary additional information such that the processor 302 may be able to select the theme based on input provided by the user. Such content may correspond to sceneries that may be able to provide the user experience of the activity the user may be participating in.

Figure 13B:
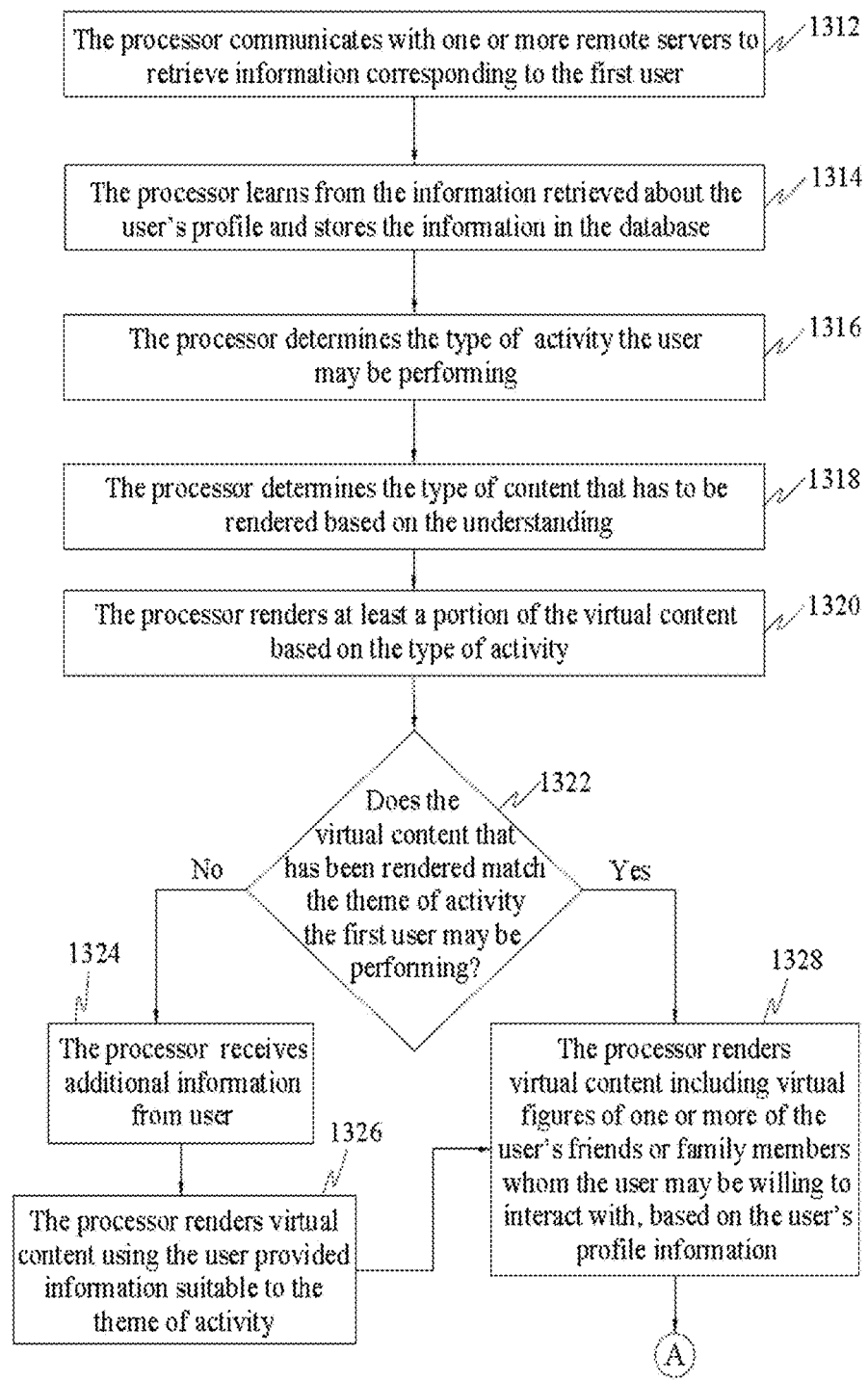
FIG. 13B-13C is another flowchart illustrating the method of rendering virtual content to the user based on the theme or the type of activity the user may be performing, in accordance with an embodiment.
Figure 13C:
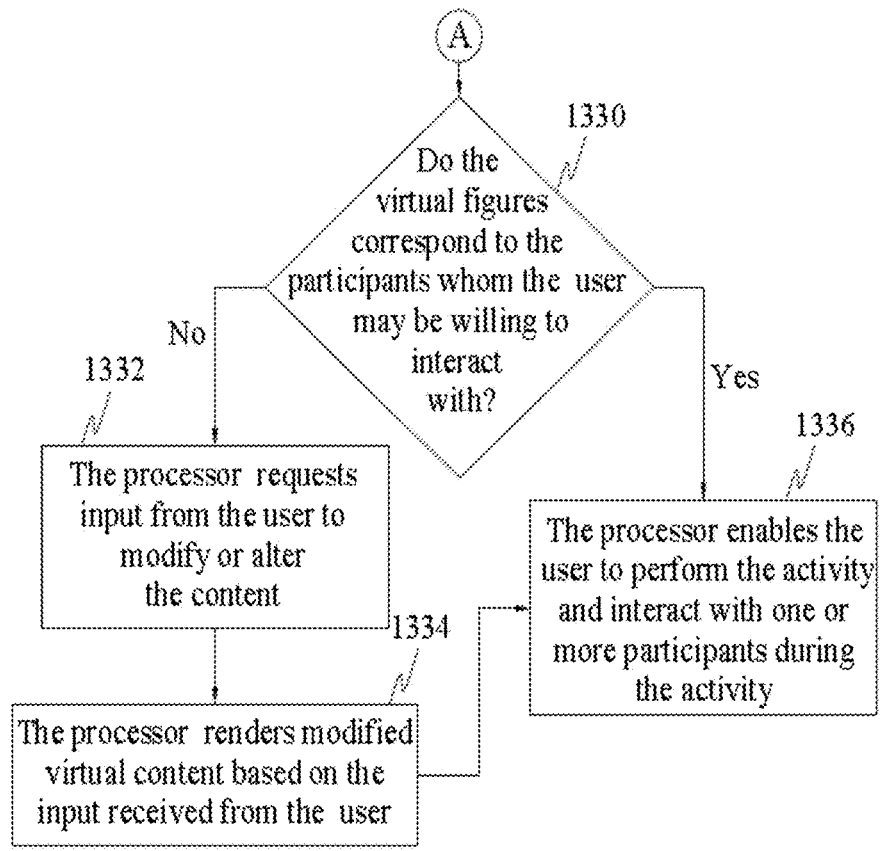

FIG. 13B is another flowchart illustrating the method of rendering virtual content to the user based on the theme or the type of activity the user may be performing, in accordance with an embodiment. At step 1312, the processor 302 may communicate with one or more remote servers 1204 to retrieve information corresponding to the user. At step 1314, the processor 302 may learn from the previous activities of the user, choice of themes by the user, relationships, preferences, hobbies, work schedule among other information and store the information in the database 308. At step 1316, the processor 302 may determine the type of activity the user may be performing. At step 1318, the processor 302 may determine the type of content that has to be rendered based on the determination of the activity. At step 1320, the processor 302 may render at least a portion of the virtual content based on the type of activity. Such virtual content rendered at this step may be only a portion of the entire content, such as, for example, the background and scenery that may form the background, among others. Such content may also include one or more other participant's virtual model. At step 1322, whether the virtual content matches the theme of activity the first user may be performing, may be determined. At step 1324, if the virtual content does not match the theme of activity which the user may be performing, then the processor 302 may request additional information from the user. Based on the received additional information, the processor 302 may, at step 1326, render virtual content using the user provided information suitable to the theme of activity. At step 1322, if the virtual content matches the theme of the activity, then at step 1328, the processor 302 may render virtual images of one or more other participants whom the user wishes to be participants in the activity. The selection of other participants in the activity may also be based on the user's profile information. The processor 302 may be configured to execute step 1328 after step 1326. The virtual images of one or more of the user's friends or family members whom the user may be willing to participate with depends on the information corresponding to the user's profile. For example, the user may wish to perform yoga with his family members. The processor 302 may receive this information from the user and subsequently may provide or render the virtual images of one or more family members of the user. At step 1330, whether the virtual images correspond to the participants whom the user may be willing to participate with, may be determined. If the virtual images do not correspond to the participants whom the user may be willing to participate with, then the processor 302, at step 1332, may request for input from the user to modify or alter the content based on the input provided by the user. At step 1334, the processor 302 may render modified virtual content based on the input received from the user. If the virtual figures correspond to the users whom the user may be willing to participate with, then, at step 1336, the processor 302 may enable the user to perform the desired activity and interact with one or more participants during the activity. Further, the processor 302 may also be configured to render images of other participants, who may not engage in the activity. The processor 302 may only display images of participants who may not engage in the activity. The processor 302 may be configured to execute step 1336 after step 1334.

In an embodiment, the content that may form the scenery may be displayed on one or more display interfaces. Such content may be in two or three dimensional format based on one or more factors, such as, the type of content, type of display interface and user's preference among others. The display interfaces may be, for example, a wall, floor and ceiling among others. The AR device may be configured to project the rendered images onto the display interface.

Figure 14A:
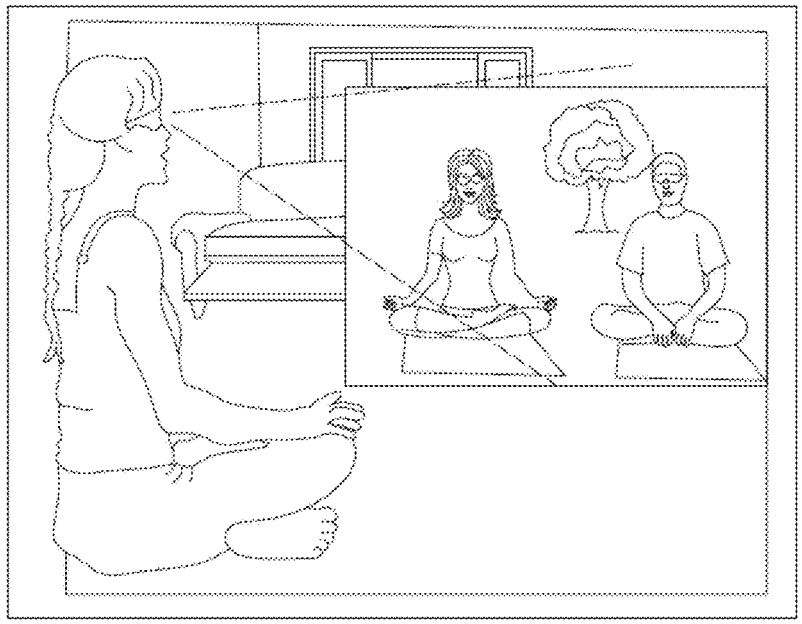
FIGS. 14A-14C illustrate exemplary scenarios wherein the system may be implemented, in accordance with an embodiment.
Figure 14B:
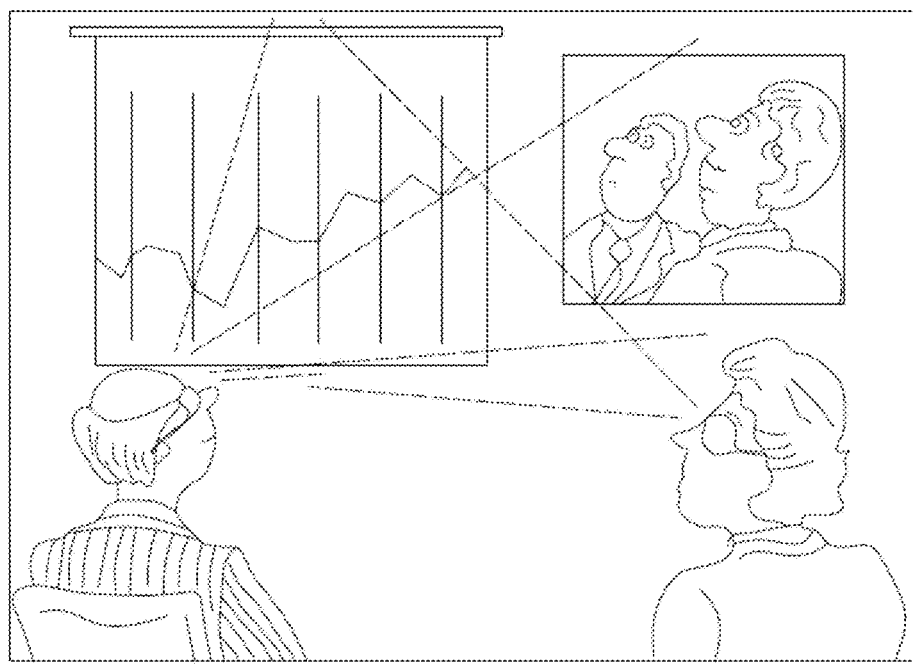
Figure 14C:
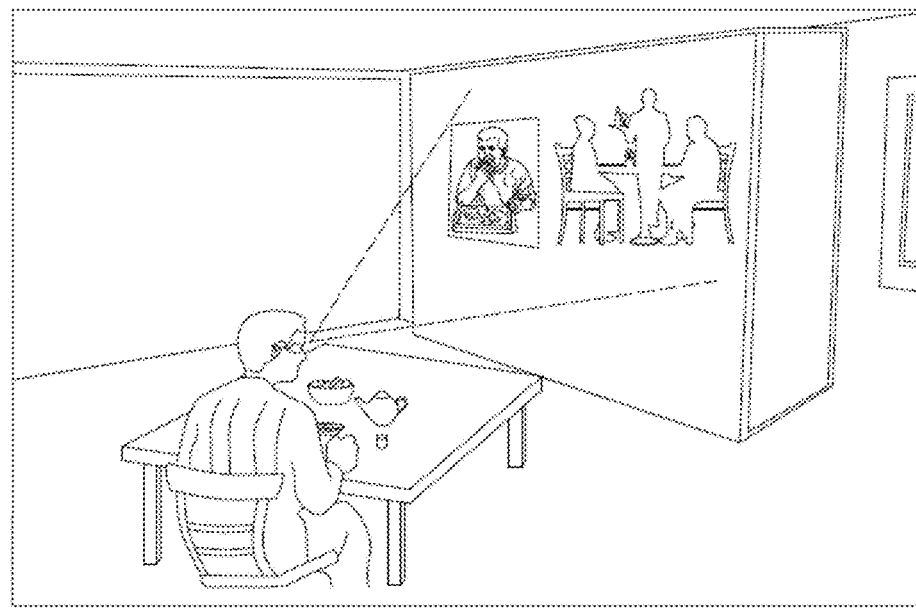

FIGS. 14A to 14C illustrate exemplary scenarios wherein the system 300 may be implemented, in accordance with an embodiment. In an example and referring to FIG. 14A, the system 300 may be configured to render virtual content, showing the virtual presence of one or more participants to a user while the user is at home preparing for a yoga session. The user may be wearing his/her AR device. The system 300 may render virtual content displaying the virtual images of one or more participants whom the user may or may not know in person. The system 300 may also allow the one or more participants to communicate with the user through the communication module 1202 during the session through voice or through texts or both voice and text. The system 300 may render the virtual content such that the user may experience an environment where the user is performing yoga with the plurality of other participants. The system 300 may also render the virtual image of an instructor whom the user may or may not know in person. The system 300 may further render suitable background scenery of a meadow or a meditation hall, among other backgrounds.

In a second exemplary scenario and referring to FIG. 14B, the system 300 may be implemented in a scenario to replace business travel by virtual teleconferences where participants may experience the feeling of physically being present at the location, interacting with their co-workers or clients, even though they may not be physically present at the location. The participants who may be wearing the VR devices may be provided access to other participants who may be participating in the conference virtually. However, the participants participating virtually may be able to see all the participants, who are physically present at the conference and who are virtually participating in the conference. Similarly, the participants, who are physically present at the conference, may be able to see all the virtual participants. This can be enabled by providing a video camera at the conference, which may record the events at the conference as well as images and videos of the participants of the conference. One or more of the participants may be enabled to take control of the session. The participant(s) who may be taking control of the session may be able to initiate the session and allow other participants to provide data to be displayed as virtual content, while the session is in progress. The data provided by the participants may be data related to the teleconference.

In a third exemplary scenario and referring to FIG. 14C, the system 300 may be implemented in a scenario where the user may be willing to dine at home as well as feel the presence of one or more of his friends or family members beside him. The processor 302 may render virtual content by receiving input from the user. The processor 302 displays the background as the scenery of a restaurant. The virtual content representing the scenery of a restaurant may be displayed to the user. The user may be enabled to select one or more friends and family members whose presence the user wishes to feel or whom the user wishes to have as participants while dining. The processor 302 may render the virtual images of those people selected by the user. The processor 302 may render the virtual image of his/her friends on a display interface such as holographic display interface. The user may be enabled to communicate with his friends while dining, through the communication module 1202.

In an embodiment, and referring to the above examples, the processor 302 may, retrieve from the database 308, information corresponding to the user's social networking profile and the user's relationship information with other users on the social networking platform. The profiles of one or more users with whom the user may be connected on the social networking platform may be retrieved and stored in the database 308. The processor 302 may generate the virtual content based on the information retrieved. The processor 302 may further instruct the VR device to display virtual models of one or more of the user's friends whose profiles may be stored in the database 308.

Alternatively or additionally, the system 300 may be configured to receive inputs from the user wherein the input may include information corresponding to the user. Such information may include a user's name, place of work, contact details, home address, list of friends of the user and their contact information, hobbies, activities the user may be involved in and recent activities the user was engaged in and daily activity schedule, among other information. Such information can also be fed to the system 100 by the user, such as, for example, by filling a questionnaire and may be stored in the database 308. The user may also provide information corresponding to his/her friends and family members such as, place of work, hobbies, activities they may like doing and recent activities they were engaged in and daily activity schedule among other such information.

In an embodiment, the processor 302 may be configured to understand the user's interest, preferences and priorities among others based on the information corresponding to the user's profile. The processor 302 may also be configured to learn what activity the user may be performing at a particular time of the day, or on any particular day, based on the user's daily activities and previous activities. Such information may be stored in the database 308 and retrieved from the same whenever necessary. Based on the learning, the processor 302 may generate the virtual content by retrieving the user's profile information from the database 308.

Figure 15A:
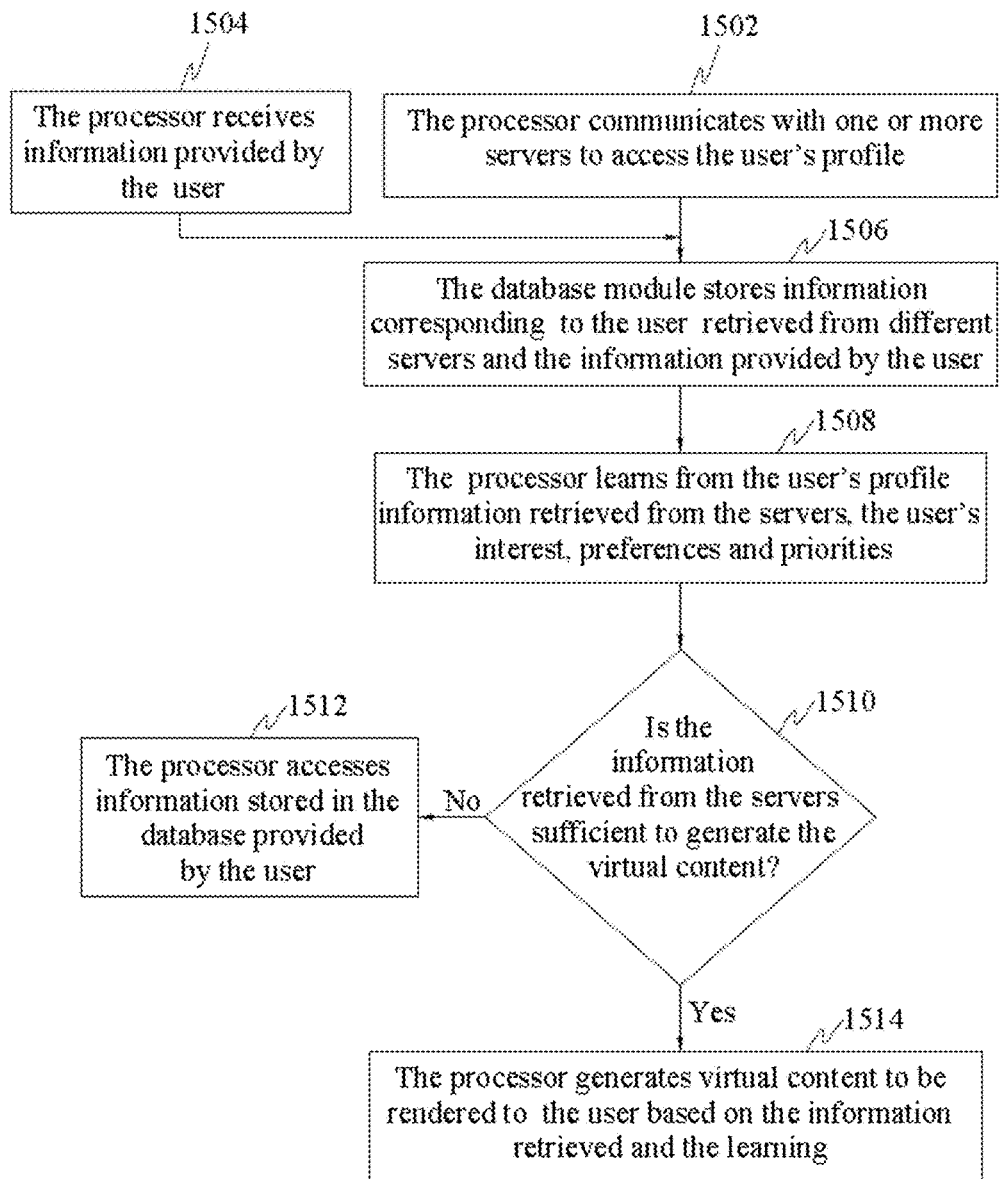
FIG. 15A is a flowchart illustrating a method of receiving information corresponding to the user and generating virtual content based on the information corresponding to the user retrieved from a database module 308, in accordance with an embodiment.

FIG. 15A is a flowchart illustrating a method of receiving information corresponding to the user and generating virtual content based on the information corresponding to the user retrieved from the database 308, in accordance with an embodiment. At step 1502, the processor 302 may communicate with one or more servers 1204 to retrieve information corresponding to the user and other participants the user may be connected with on one or more platforms. The platforms may be for example, social networking platforms. At step 1504, the processor 302 may further receive information corresponding to the user and other participants the user may be connected with on one or more platforms provided by the user. The user may provide such information manually through a user interface that may be associated with the system 300. At step 1506, the database 308 may store the information corresponding to the user retrieved from different servers 1204 and the information provided by the user. Information provided by the user may include information corresponding to one or more users the user may know or may be willing to participate with, in an activity. At step 1508, the processor 302 may learn from the user's profile information retrieved from the servers 1204, the user's interest, preferences and priorities. At step 1510, whether the information retrieved from the servers 1204 is sufficient to generate the virtual content, may be determined. If the information from the servers 1204 is not sufficient, the processor 302, at step 1512, may access the information stored in the database 308, which may be provided by the user. If the information from the servers 1204 is sufficient to generate the virtual content, then, at step 1514, the processor 102 may generate virtual content to be rendered and displayed to the user based on the information retrieved. Also step 1514 may be executed after step 1512.

In an embodiment, the processor 302 may instruct the VR device to display a list showing the names or profiles of one or more users whom the user might have interacted with on one or more platforms earlier. Such profiles may be stored in the database 308. The user may be provided an option to select one or more users to participate in an activity with from the displayed list. Such a list may be generated by the processor 302 by accessing the database 308. The processor 302 may instruct the VR device to provide virtual images of one or more of the users whose names and profile information may be displayed on the list. The processor 302 may render the virtual content and communicate it to the VR device for display.

The processor 302 through the communication module 1202 may further be configured to notify the participants, whose profiles have been selected by the user, about the user's interest in participating in the activity with them. One or more of the participants to whom the notification may have been communicated, may show interest in joining the user in the activity. The processor 302 may accept response from one or more participants who may show interest in joining the user in the activity. The processor 302 may render the virtual content displaying the presence of the participants who may have responded showing interest in joining the user. The virtual content may be videos of the other users. The user may be enabled to communicate or interact with the other users through the communication module 1204. The image capturing device of the system 300 may capture images of the user and communicate it to the other users. Similarly, the respective image capturing devices of the systems 300 of the other users may capture the image and voice of the other users and communicate it to the user.

In yet another embodiment, the user may be enabled to send requests to one or more participants, whom the user may be acquainted with, to join the user during the yoga session. The other participants may accept or decline the request. The processor 302 may display the virtual presence of the participants who may have accepted the user's request. The virtual content may be videos of the other users. The user may be enabled to communicate with the other participants through voice data. Alternatively, the user may be able to send requests to one or more users whom the user may be connected with on a social networking platform. The image capturing device of the system 100 may capture images of the user and communicate it to the other users. Similarly, the respective image capturing devices of the systems 100 of the other users may capture the image and voice of the other users and communicate it to the user. The other users may replicate the actions performed by the user.

Figure 15B:
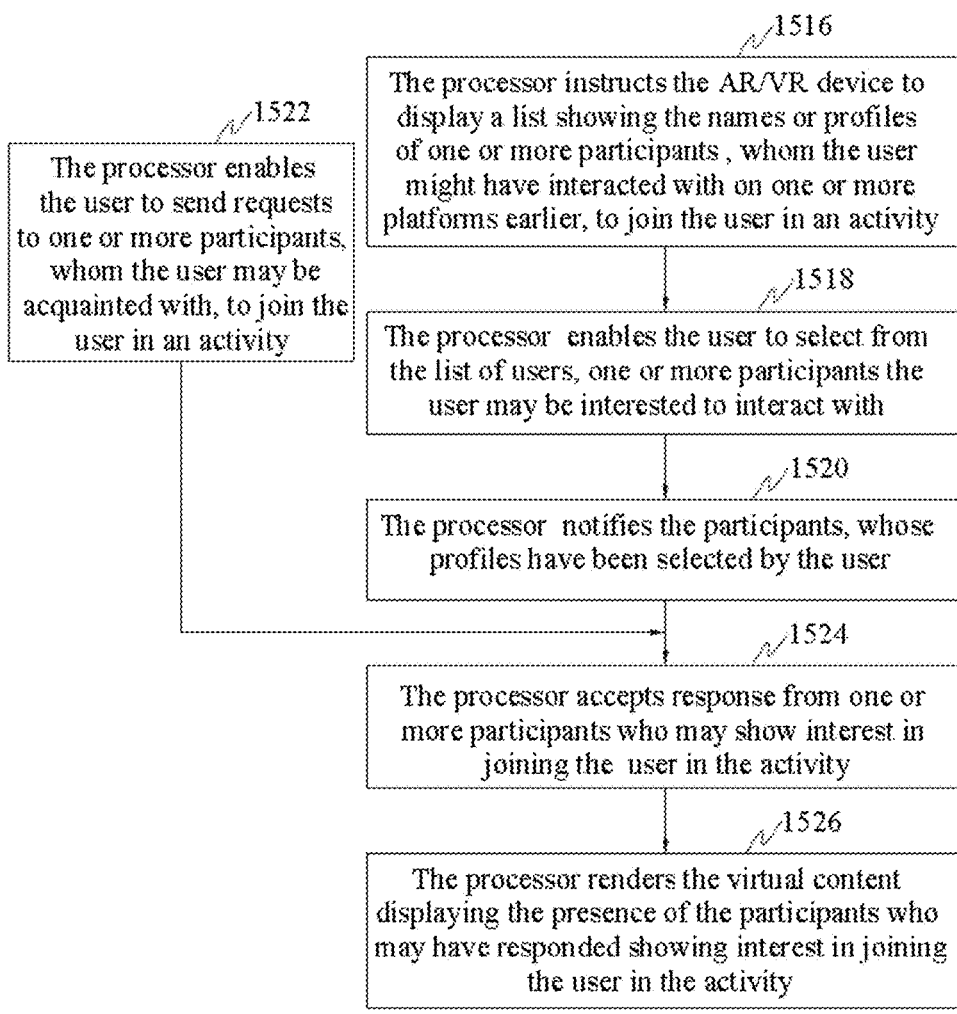
FIG. 15B is a flowchart illustrating the method of rendering virtual content based on the user's selection of participants in the activity, in accordance with an embodiment.

FIG. 15B is a flowchart illustrating the method of rendering virtual content based on the user's selection of participants in the activity, in accordance with an embodiment. At step 1516, the processor 302 may instruct the VR device to display a list to the user, displaying the names or profiles of one or more participants, whom the user might have interacted with on one or more platforms earlier, to join the user in an activity. At step 1518, the processor 302, may enable the user to select from the list of users, one or more participants the user may be interested to participate with. At step 1520, the processor 302 may notify the participants, whose profiles have been selected by the user. At step 1522, the processor 302 may further enable the user to send requests to one or more participants, whom the user may be acquainted with, to join the user in an activity. It may be noted that the steps 1516 and 1522 can be optional and may be executed individually in two different scenarios. At step 1524, the processor 302 may accept response from one or more participants who may show interest in joining the user in the activity. At step 1526, the processor 302 may render the virtual content displaying the presence of the participants who may have responded showing interest in joining the user in the activity.

In another embodiment, the processor 302 may be configured to render virtual content displaying virtual presence of one or more participants whom the user may be willing to participate with, based on preconfigured or configurable set of rules incorporated in the processor 302. The processor 302 may learn from the user's previous interactions and types of activities and thereby determine, whom the user may be willing to participate with for one particular activity. For example, the user may have participated in yoga sessions with users A, B and C on one particular day and with users B, D and G on a second day. On a third day, the processor 302 may render virtual content wherein the virtual content may display virtual model of user B and allow the user to select other users in addition to user B to perform yoga.

Figure 15C:
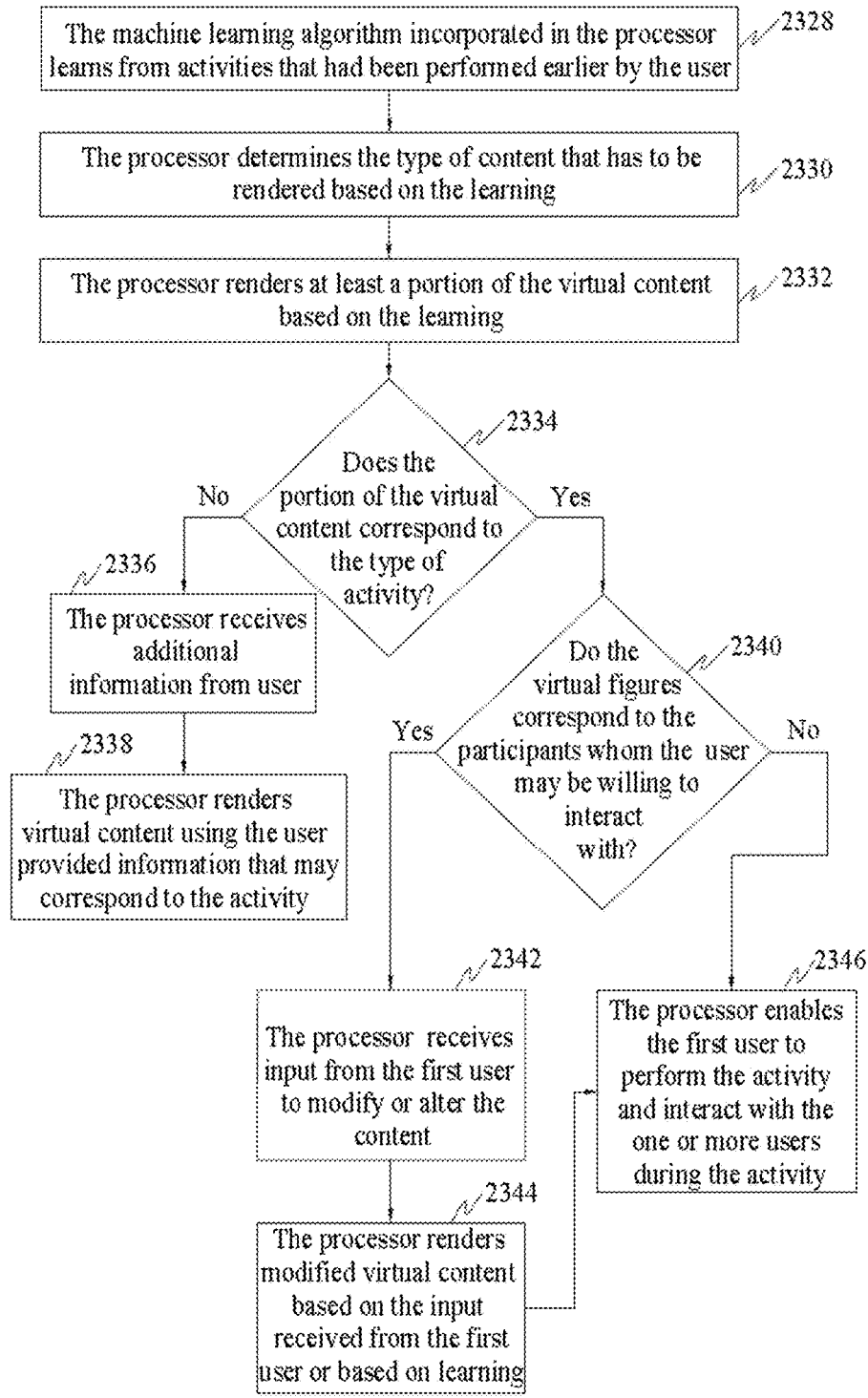
FIG. 15C is a flowchart illustrating the method of rendering virtual content based on machine learning algorithm incorporated in the processor, in accordance with an embodiment.

FIG. 15C is a flowchart illustrating the method of rendering virtual content based on machine learning algorithm incorporated in the processor 302, in accordance with an embodiment. At step 1528, the machine learning algorithm incorporated in the processor 302 may be configured to learn from activities that had been performed earlier by the user. At step 1530, the processor 302 may determine the type of content that has to be rendered based on the learning. At step 1532, the processor 302 may render at least a portion of the virtual content based on the learning. Such content may include images of one or more participants whom the user may have performed an activity with earlier. At step 1534, the processor 302 may determine whether the portion of the virtual content displayed corresponds to a particular activity. For example, the processor 302 may determine whether the model of the user rendered, corresponds to the participant who might have performed the activity with the user earlier. If the portion of the virtual content displayed does not correspond to the particular activity, then, at step 1536, the processor 302 may request for additional information from user. At step 1538, the processor 302 may render virtual content using the user provided information that may correspond to the activity. If the portion of the virtual content displayed corresponds to the particular activity, then, at step 1540, the processor 302 may provide an option to the user to modify the content. Modifying the content may include adding more participants to the content, removing participants from the content and changing the type of activity, among others. If the user wishes to modify the content, then at step 1542, the processor 302 may receive input from the user to modify or alter the content. At step 1544, the processor 102 may render modified virtual content based on the input received from the user. If the user does not wish to modify the content, then at step 1546, the processor 302 may enable the user to perform the activity and communicate with the one or more users during the activity.

The processor 302 may render virtual content to the user, displaying videos of the participants the user might be willing to participate with. The video data may be integrated with voice data. Alternatively, the processor 302 may generate virtual two or three dimensional models of the participants the user might be willing to participate with. The virtual two or three dimensional models of the participants may be integrated with voice data. Further, the processor 302 may be able to render pre recorded voice data to the virtual two or three dimensional models. The user may be able to communicate with the virtual content displaying presence of the participants the user might be willing to participate with, through voice and text.

The system 300 may be integrated with one or more social networking servers 1204 such as Facebook. The system 300 may enable the users to log in to the social networking portal. The user's profile may be connected or related with a plurality of other users on the portal. The user may be provided an option to communicate with one or more of the plurality of users who may be available or online as seen on the page of the social networking portal. The user may be provided an option to participate with a plurality of users whom the user may prefer to communicate with. Virtual models of one or more of the plurality of users may be rendered and displayed to the user for communication. The communication may happen in the form of voice or text.

In an embodiment, the processor 302 may render virtual two or three dimensional models of random users/people that the user may not know in person. Such random profiles of users whom the user may or may not know in person may be preconfigured by the processor 302 by receiving input from the user. Further, such profiles may be preconfigured profiles of other users by the processor 302 may be created by applying intelligence based on the user's preference, interest and priorities, among others. These preconfigured profiles of random people may be stored in the database 308. Examples of random models may include models of celebrities or animated characters, among other profiles. The processor 302 may be configured to voice attributes among other such attributes to such models. Such random virtual three dimensional models of random participants may be rendered when the user may not be willing to communicate with the users who may be connected with the user or such users may not be available to communicate at that instant.

In one embodiment, for the system 300 to enable the users to participate in an activity and communicate with the user in virtual reality, it may be required that all the other users wear their respective VR devices.

Input such as, tactile and gesture input, data indicating pressure and force vectors, applied through the user's limbs, among others may be received through one or more sensors included in the system 300. The processor 302 may be configured to synthesize the input and determine the visual output or outcome based on the input. The outcome may be applied to the virtual images to alter one or more parameters (location, size etc) of the objects in the virtual images. Gestures along with the semantics of each gesture received through the sensors may be stored in the database 308. The semantics of the gestures may be predefined and stored in the database 308. The database 308 may also store outcomes of such input. The outcomes may indicate one or more physical actions carried by the user which may be applied to the virtual content to modify or alter parameters of the content.

Figure 16A:
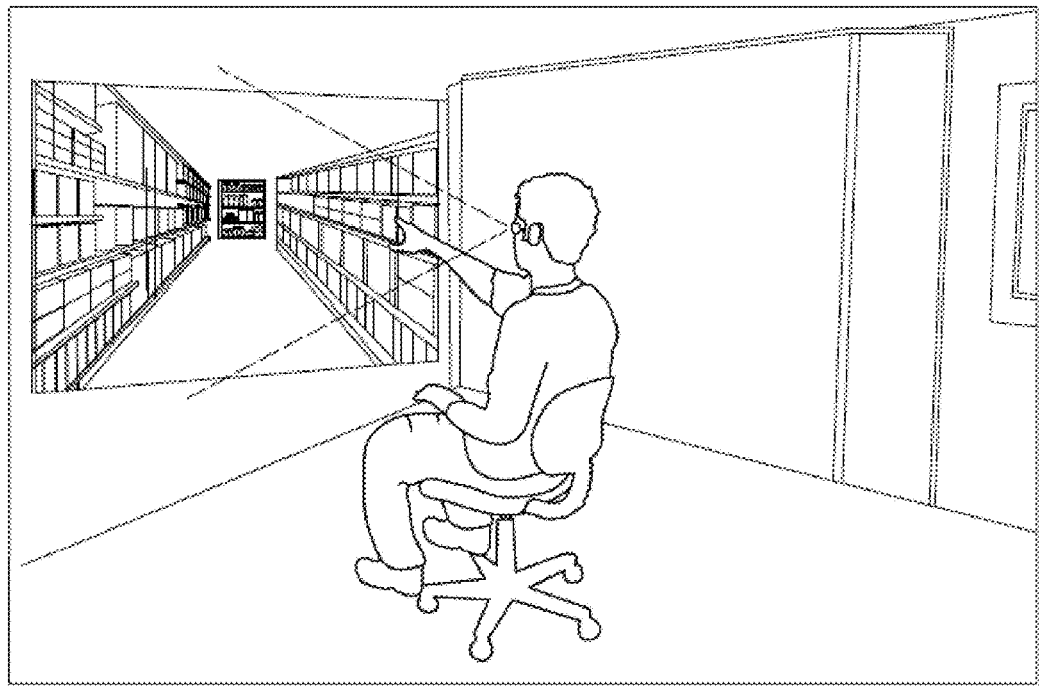
FIGS. 16A and 16B are illustrations of exemplary scenarios wherein virtual content is rendered to a user to provide the user with a shopping experience.
Figure 16B:
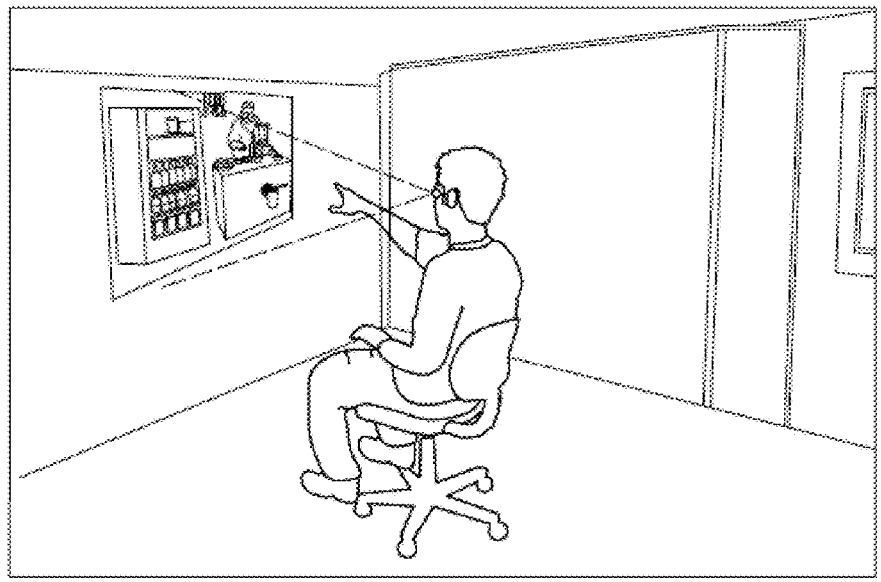

In another exemplary scenario, and referring to FIGS. 16A and 16B, virtual content may be displayed to the user to provide the user with the experience of physically shopping at a location, though the user is indulging in virtual shopping. The system 300 may be able to communicate with one or more remote servers 1204 via the communication module 1202. The servers 1204 may be associated with one or more service providers such as, store websites, online shopping websites and super markets among other service providers. Input may be accepted from the users, through a user interface. The user interface may be portals pertaining to the service providers. Input may include requests to view a shopping location, having at least one store, and displaying the shopping location to the user via the virtual interface of the system 300. The input may be in the form of URLs provided through a virtual browser that may identify a particular service provider's website. The system 300 may provide users with experience of walking beside aisles of the stores, entering the store by opening and walking through its doors, examining the items on the shelves, and placing them into the shopping cart. The gesture of picking up an item and placing it in the shopping cart may be perceived as placing an item in the shopping cart.

The virtual content may be preconfigured or configurable by the service providers. The processor 302 may access the servers 1204 associated with the plurality of service providers and render and display the virtual content to the users. The content may be customized for each user and the customization may be based on the user's profile. The user's profile may include information corresponding to the user's history of purchase, age, gender, location of the user and the user's preferences, among others. The user may create a profile on the portals of the service providers. Alternatively, the servers associated with the service providers may be able to retrieve such information from one or more servers 1204 associated with one or more platforms where the user may have already created a profile. Further, the servers associated with the service providers may be able to retrieve such information corresponding to the user from the processor 302.

In an embodiment, if the user is virtually shopping at a store, the user may request to interact with one or more of the store's shopping assistant while purchasing. The users may post queries and the shopping assistant, who may provide answers to the queries. In addition, the virtual content that may be presented to the users by the service providers may enable the users to learn about the store, its brands, or any other information the store may wish to covey to the user. Further, the users may be able to provide feedback based on their experience.

Alternatively, the users may be assisted by virtual shopping assistants at one or more sections while purchasing. For example, when the user may not be able to decide between two similar items and spends more time browsing at one particular section without placing any item into the shopping cart, the shopping assistant's virtual model may be displayed to the user to assist the user in the purchase. The store keeper may provide reviews and feedbacks of other customers to the user and help the user make the purchase.

In another embodiment, virtual assistance may be rendered into virtual reality by means of one or more among text and voice as opposed to virtual models of shopping assistants providing assistance.

In an embodiment, virtual content for an online shopping website may be pre configured or configurable by the service provider. The processor 302 may access the servers associated with a plurality of service providers and render and display the virtual content to the users. The user may request for the shopping assistant to assist him/her with the purchase. For example, if the user is shopping for apparels, he/she may request virtual assistance from a stylist or may request for the specifications of the product. If the user is purchasing a book, the user may scan through the cover and request for reviews. Reviews provided by other users may be displayed in virtual reality. Virtual assistance may also be rendered into virtual reality by means of one or more among text and voice as opposed to virtual models of random people.

In an embodiment, all information corresponding to a particular product may be rendered and displayed as soon as the user selects the product or places it into the shopping cart, in virtual reality. Information may include all reviews provided by users from across the world, specification of a particular product and a comparison chart between two or more similar products among others may be rendered to the user in virtual reality. Such information may appear as texts. Such information may be presented by random models of users who may have purchased the product earlier or who may be associated with the product through audio output. Further such information may be presented as one or more among texts and voices.

In an embodiment, virtual assistance may be provided to the user based on the user's profile and purchase history, among others. Alternatively, the users may be provided with options to select assistance whenever the user might require assistance.

Figure 16C:
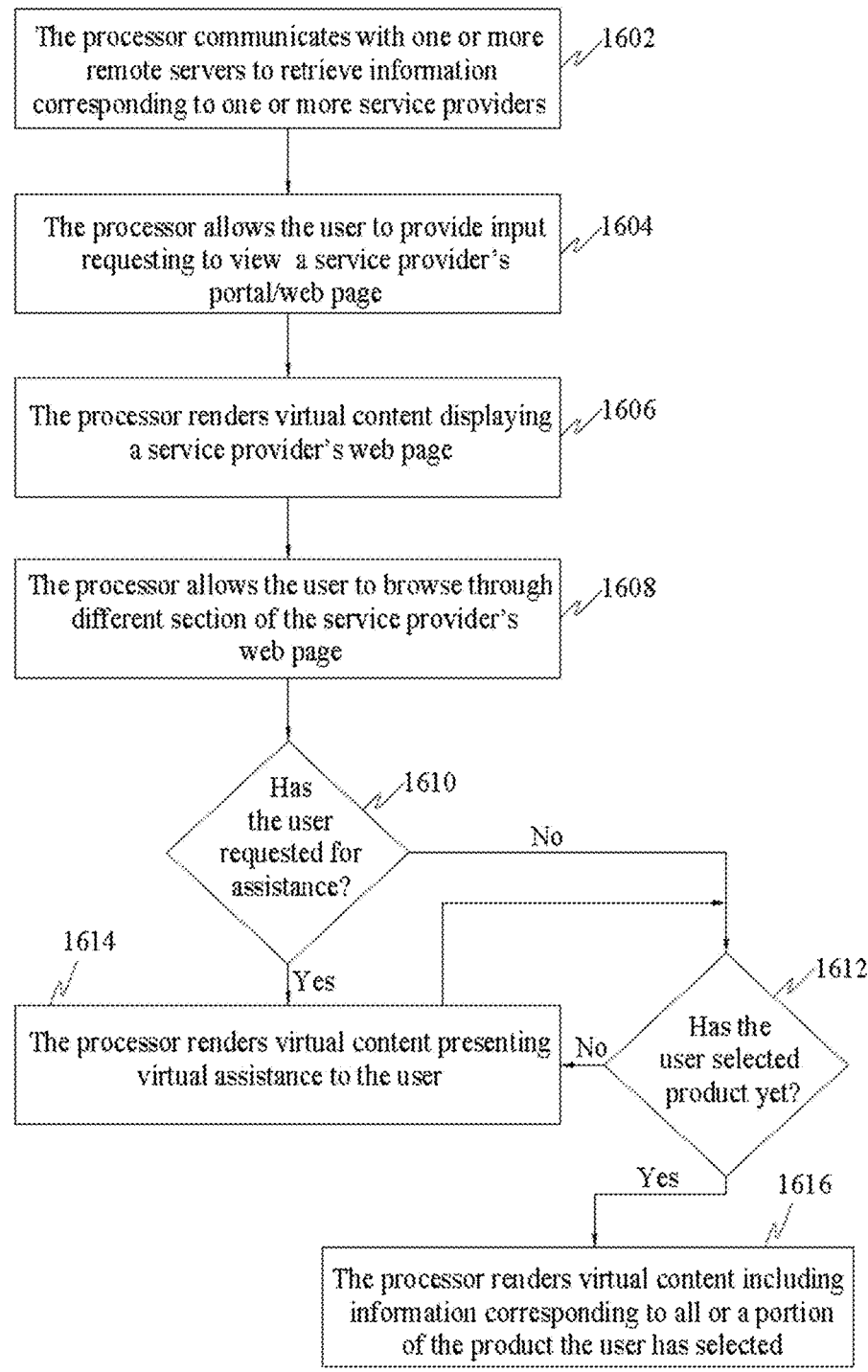
FIG. 16C is a flowchart illustrating the method of rendering virtual content to the user to enable the user to shop online or at virtual stores, in accordance with an embodiment.

FIG. 16C is a flowchart illustrating the method of rendering virtual content to the user to enable the user to shop online or at stores, in accordance with an embodiment. At step 1602, the processor 302 may communicate with one or more remote servers to retrieve information corresponding to one or more service providers. At step 1604, the processor 302 may allow the user to provide input requesting to view a service provider's portal/webpage. At step 1606, the processor 302 may render virtual content displaying a service provider's webpage. At step 1608, the processor 302 may allow the user to browse through different sections of the service provider's webpage. At step 1610, the processor 302 may determine if the user has requested for assistance to make a purchase. If the user has not requested assistance, then the processor 302, at step 1612, determines whether the user has selected any product. If the processor 302 determines that the user has requested for assistance to make a purchase, then at step 1614 the processor 302 may render virtual content presenting virtual assistance to the user. After step 1614 has been executed, the processor 302 may execute step 1612 again until the processor determines that the user has made a selection at step 1612. If the processor 302 determines that the user has made a selection, then, the processor 302, at step 1616 may render virtual content including information corresponding to all or a portion of the products the user has selected.

In an embodiment, the user may be provided an option to proceed with payment after making selection. The user may also be assisted during the payment. Virtual assistance may be provided to the user to select a payment method and accordingly proceed with the steps of payment. Such virtual assistance may be in the form of voice or text or virtual models may be presented to assist the user.

In another embodiment, the system 300 may be integrated with an application module that may be implemented for the purpose of enabling the user to shop online or at physical stores virtually in a two or three dimensional virtual reality interface. The user may be required to log into the application module and browse for shops or products or categories of products through the virtual interface.

In some embodiments, one or more of users participating in the activities in all the above examples may have cameras or any image or video capturing devices integrated with their respective VR devices. Images, photos, videos or live webcam feeds of the users may be communicated to the other users whom they are participating and communicating with.

In an embodiment, the users may communicate with one another in virtual reality via voice communication modules. The users may also communicate with other users using voice data through a telephone module. The users may be enabled to provide voice data through a microphone and receive voice data from other users through headphones or speakers.

In an embodiment, the rendering module 304 may render enlarged lifesize views of three-dimensional content on display surfaces such as walls, floor, ceiling and table surfaces among others.

In an embodiment, live feeds from one or more servers 1204 may be received and processed by the processor 302 in near real time to generate the virtual content.

The system can be used in industrial applications, for example in repair/maintenance augmentation. One exemplary pseudo-code is Repair Augmentation User selects AR assisted repair mode, System identifies surface and components mounted thereon System looks up repair sequence:

determines type of component, location of component, identifies or highlights on the HUD each component to be opened or removed and provides instructions on removal techniques, wait until each component is opened or removed and then show next component until done accesses the target component to replace or repair and show instructions to repair or replace, sequentially shows instructions to put back components previously opened or removed.

In one example, the AR interface may overlay the objects observed on the sorting surface with highlight in which the various objects are outlined in different colors: e.g. PET as red, PVC, as blue, PE as green, and polycarbonate as purple. Additional information may include compositional information appearing as text or additional coding in the AR interface. In one system, the criticality associated with each object may be indicated by the brightness of the outline color; more vivid colors may indicate that high attention should be paid to the object. Alternatively, object criticality may be displayed in terms of the jaggedness of outlined shapes in which more jagged outlines indicate lesser criticality. In yet another alternative example, the function of the object may be displayed as text superimposed on the object image.

In another implementation, objects may be presented to the illumination and sensors so that their content may be analyzed and their placement on the repair surface may be determined by the computing system. The computing system may then supply augmented reality data streams to the AR interface users to inform them of the composition of each of the sortable objects.

In one embodiment for sorting a stream of small objects, a sorting machine can have a number of lanes on a moving sorting surface, each lane containing objects having the same composition. For example, as the sorting surface moves between a group of sorters, the sorters may simply push the objects into a specific lane based on composition. The AR system can color code each object to be sorted into a particular lane. At the end of the moving surface, a sorter may have pre-arranged bins placed to receive the objects from each lane as they fall off the surface into the appropriate bin. The AR system can provide sensors such as spectral sensors for a majority determination of composition. In the event that an object does not have a consistent spectral response, information may be presented over the AR interface to a sorter, letting him or her know that the object should be set aside for further consideration. The computing system may provide a group of sorters, using augmented reality interfaces, with information regarding how to bin each object. The sorters may continue to place objects by composition into appropriate bins until the bins become full. In one configuration, a sorter may then stop sorting and move the bin to a shipping location. During the time the sorter is away from his or her position by the sorting surface, the sorter may notify a facility operator of this break in the sorting process over a voice transmitting channel associated with the AR interface. Alternatively, another facility worker may move the bin to a post-processing station (such as a station to box the items for shipping to another facility). If the post-processing station becomes overburdened due to a large amount of material to ship out, the post-processing worker may notify the facility operator over an AR interface voice channel that the sorting process for that particular material should be delayed. In either alternative, the facility operator may then direct the computing system to slow the travel of the moving sorting surface or even stop it entirely. In this manner, the sorting process may be adapted to changes in the work flow.

Figure 17A:
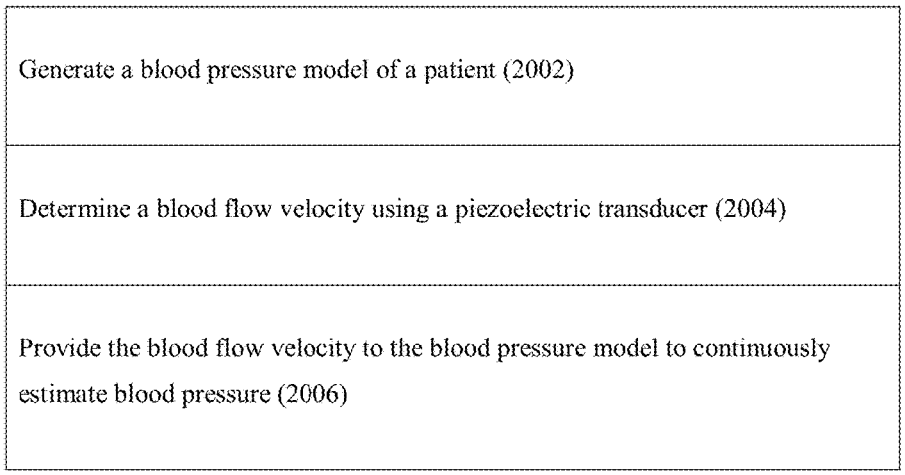
FIGS. 17A to 17B shows exemplary processes to estimate blood pressure for the system of FIG. 2D.
Figure 17B:
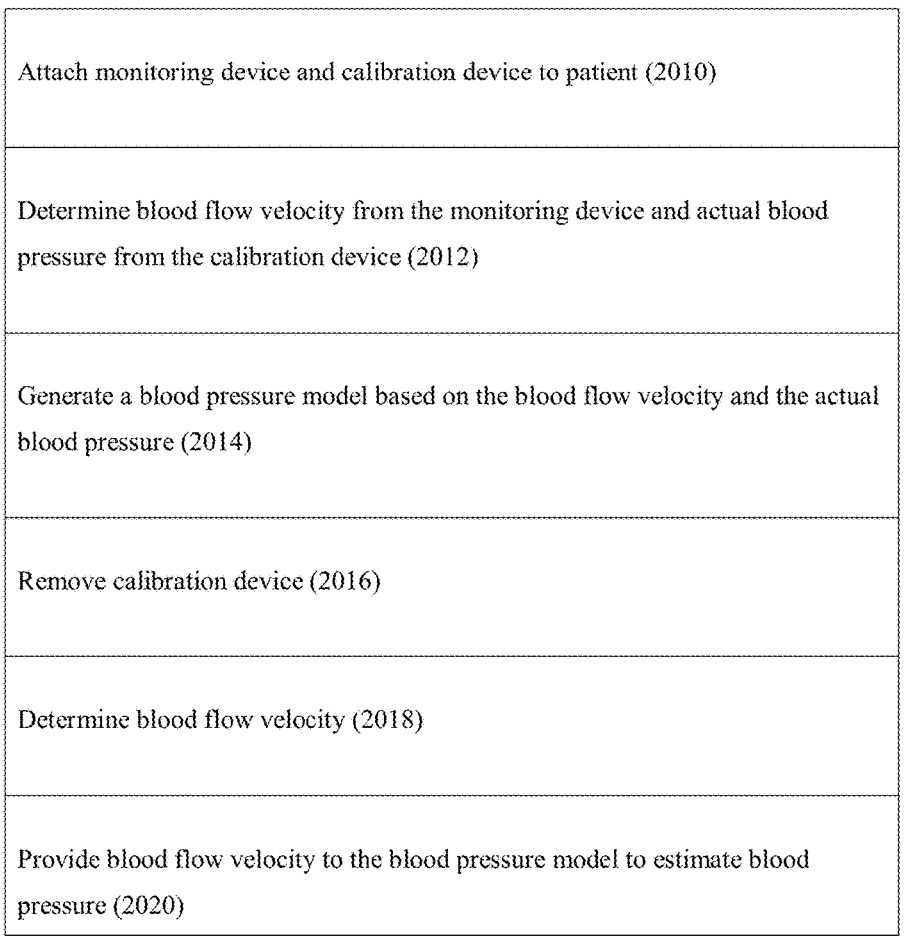

FIG. 17A shows ant exemplary process to continuously determine blood pressure of a patient. The process generates a blood pressure model of a patient (2002); determines a blood flow velocity using a piezoelectric transducer (2004); and provides the blood flow velocity to the blood pressure model to continuously estimate blood pressure (2006). FIG. 17B shows another exemplary process to continuously determine blood pressure of a patient. First, during an initialization mode, a monitoring device and calibration device are attached to patient (2010). The monitoring device generates patient blood flow velocity, while actual blood pressure is measured by a calibration device (2012). Next, the process generates a blood pressure model based on the blood flow velocity and the actual blood pressure (2014). Once this is done, the calibration device can be removed (2016). Next, during an operation mode, the process periodically samples blood flow velocity from the monitoring device on a real-time basis (18) and provides the blood flow velocity as input information to the blood pressure model to estimate blood pressure (20). This process can be done in continuously or periodically as specified by a user.

In one embodiment, to determine blood flow velocity, acoustic pulses are generated and transmitted into the artery using an ultrasonic transducer positioned near a wrist artery. These pulses are reflected by various structures or entities within the artery (such as the artery walls, and the red blood cells within the subject's blood), and subsequently received as frequency shifts by the ultrasonic transducer. Next, the blood flow velocity is determined. In this process, the frequencies of those echoes reflected by blood cells within the blood flowing in the artery differ from that of the transmitted acoustic pulses due to the motion of the blood cells. This well known "Doppler shift" in frequency is used to calculate the blood flow velocity. In one embodiment for determining blood flow velocity, the Doppler frequency is used to determine mean blood velocity. For example, U.S. Pat. No. 6,514,211, the content of which is incorporated by reference, discusses blood flow velocity using a time-frequency representation.

In one implementation, the system can obtain one or more numerical calibration curves describing the patient's vital signs such as blood pressure. The system can then direct energy such as infrared or ultrasound at the patient's artery and detecting reflections thereof to determine blood flow velocity from the detected reflections. The system can numerically fit or map the blood flow velocity to one or more calibration parameters describing a vital-sign value. The calibration parameters can then be compared with one or more numerical calibration curves to determine the blood pressure.

Additionally, the system can analyze blood pressure, and heart rate, and pulse oximetry values to characterize the user's cardiac condition. These programs, for example, may provide a report that features statistical analysis of these data to determine averages, data displayed in a graphical format, trends, and comparisons to doctor-recommended values.

In one embodiment, feed forward artificial neural networks (NNs) are used to classify valve-related heart disorders. The heart sounds are captured using the microphone or piezoelectric transducer. Relevant features were extracted using several signal processing tools, discrete wavelet transfer, fast fourier transform, and linear prediction coding. The heart beat sounds are processed to extract the necessary features by: a) denoising using wavelet analysis, b) separating one beat out of each record c) identifying each of the first heart sound (FHS) and the second heart sound (SHS). Valve problems are classified according to the time separation between the FHS and th SHS relative to cardiac cycle time, namely whether it is greater or smaller than 20% of cardiac cycle time. In one embodiment, the NN comprises 6 nodes at both ends, with one hidden layer containing 10 nodes. In another embodiment, linear predictive code (LPC) coefficients for each event were fed to two separate neural networks containing hidden neurons.

In another embodiment, a normalized energy spectrum of the sound data is obtained by applying a Fast Fourier Transform. The various spectral resolutions and frequency ranges were used as inputs into the NN to optimize these parameters to obtain the most favorable results.

In another embodiment, the heart sounds are denoised using six-stage wavelet decomposition, thresholding, and then reconstruction. Three feature extraction techniques were used: the Decimation method, and the wavelet method. Classification of the heart diseases is done using Hidden Markov Models (HMMs).

In yet another embodiment, a wavelet transform is applied to a window of two periods of heart sounds. Two analyses are realized for the signals in the window: segmentation of first and second heart sounds, and the extraction of the features. After segmentation, feature vectors are formed by using he wavelet detail coefficients at the sixth decomposition level. The best feature elements are analyzed by using dynamic programming.

In another embodiment, the wavelet decomposition and reconstruction method extract features from the heart sound recordings. An artificial neural network classification method classifies the heart sound signals into physiological and pathological murmurs. The heart sounds are segmented into four parts: the first heart sound, the systolic period, the second heart sound, and the diastolic period. The following features can be extracted and used in the classification algorithm: a) Peak intensity, peak timing, and the duration of the first heart sound b) the duration of the second heart sound c) peak intensity of the aortic component of S2(A2) and the pulmonic component of S2 (P2), the splitting interval and the reverse flag of A2 and P2, and the timing of A2 d) the duration, the three largest frequency components of the systolic signal and the shape of the envelope of systolic murmur e) the duration the three largest frequency components of the diastolic signal and the shape of the envelope of the diastolic murmur.

In one embodiment, the time intervals between the ECG R-waves are detected using an envelope detection process. The intervals between R and T waves are also determined. The Fourier transform is applied to the sound to detect S1 and S2. To expedite processing, the system applies Fourier transform to detect S1 in the interval 0.1-0.5 R-R. The system looks for S2 the intervals R-T and 0.6 R-R. S2 has an aortic component A2 and a pulmonary component P2. The interval between these two components and its changes with respiration has clinical significance. A2 sound occurs before P2, and the intensity of each component depends on the closing pressure and hence A2 is louder than P2. The third heard sound S3 results from the sudden halt in the movement of the ventricle in response to filling in early diastole after the AV valves and is normally observed in children and young adults. The fourth heart sound S4 is caused by the sudden halt of the ventricle in response to filling in presystole due to atrial contraction.

In yet another embodiment, the S2 is identified and a normalized splitting interval between A2 and P2 is determined. If there is no overlap, A2 and P2 are determined from the heart sound. When overlap exists between A2 and P2, the sound is dechirped for identification and extraction of A2 and P2 from S2. The A2-P2 splitting interval (SI) is calculated by computing the cross-correlation function between A2 and P2 and measuring the time of occurrence of its maximum amplitude. SI is then normalized (NSI) for heart rate as follows: NSI=SI/cardiac cycle time. The duration of the cardiac cycle can be the average interval of QRS waves of the ECG. It could also be estimated by computing the mean interval between a series of consecutive S1 and S2 from the heart sound data. A non linear regressive analysis maps the relationship between the normalized NSI and PAP. A mapping process such as a curve-fitting procedure determines the curve that provides the best fit with the patient data. Once the mathematical relationship is determined, NSI can be used to provide an accurate quantitative estimate of the systolic and mean PAP relatively independent of heart rate and systemic arterial pressure.

In another embodiment, the first heart sound (S1) is detected using a time-delayed neural network (TDNN). The network consists of a single hidden layer, with time-delayed links connecting the hidden units to the time-frequency energy coefficients of a Morlet wavelet decomposition of the input phonocardiogram (PCG) signal. The neural network operates on a 200 msec sliding window with each time-delay hidden unit spanning 100 msec of wavelet data.

In yet another embodiment, a local signal analysis is used with a classifier to detect, characterize, and interpret sounds corresponding to symptoms important for cardiac diagnosis. The system detects a plurality of different heart conditions. Heart sounds are automatically segmented into a segment of a single heart beat cycle. Each segment are then transformed using 7 level wavelet decomposition, based on Coifman 4th order wavelet kernel. The resulting vectors 4096 values, are reduced to 256 element feature vectors, this simplified the neural network and reduced noise.

In another embodiment, feature vectors are formed by using the wavelet detail and approximation coefficients at the second and sixth decomposition levels. The classification (decision making) is performed in 4 steps: segmentation of the first and second heart sounds, normalization process, feature extraction, and classification by the artificial neural network.

In another embodiment using decision trees, the system distinguishes (1) the Aortic Stenosis (AS) from the Mitral Regurgitation (MR) and (2) the Opening Snap (OS), the Second Heart Sound Split (A2_P2) and the Third Heart Sound (S3). The heart sound signals are processed to detect the first and second heart sounds in the following steps: a) wavelet decomposition, b) calculation of normalized average Shannon Energy, c) a morphological transform action that amplifies the sharp peaks and attenuates the broad ones d) a method that selects and recovers the peaks corresponding to S1 and S2 and rejects others e) algorithm that determines the boundaries of S1 and S2 in each heart cycle f) a method that distinguishes S1 from S2.

In one embodiment, once the heart sound signal has been digitized and captured into the memory, the digitized heart sound signal is parameterized into acoustic features by a feature extractor. The output of the feature extractor is delivered to a sound recognizer. The feature extractor can include the short time energy, the zero crossing rates, the level crossing rates, the filter-bank spectrum, the linear predictive coding (LPC), and the fractal method of analysis. In addition, vector quantization may be utilized in combination with any representation techniques. Further, one skilled in the art may use an auditory signal-processing model in place of the spectral models to enhance the system's robustness to noise and reverberation.

In one embodiment of the feature extractor, the digitized heart sound signal series s(n) is put through a low-order filter, typically a first-order finite impulse response filter, to spectrally flatten the signal and to make the signal less susceptible to finite precision effects encountered later in the signal processing. The signal is preemphasized preferably using a fixed pre-emphasis network, or preemphasizer. The signal can also be passed through a slowly adaptive pre-emphasizer. The preemphasized heart sound signal is next presented to a frame blocker to be blocked into frames of N samples with adjacent frames being separated by M samples. In one implementation, frame 1 contains the first 400 samples. The frame 2 also contains 400 samples, but begins at the 300th sample and continues until the 700th sample. Because the adjacent frames overlap, the resulting LPC spectral analysis will be correlated from frame to frame. Each frame is windowed to minimize signal discontinuities at the beginning and end of each frame. The windower tapers the signal to zero at the beginning and end of each frame. Preferably, the window used for the autocorrelation method of LPC is the Hamming window. A noise canceller operates in conjunction with the autocorrelator to minimize noise. Noise in the heart sound pattern is estimated during quiet periods, and the temporally stationary noise sources are damped by means of spectral subtraction, where the autocorrelation of a clean heart sound signal is obtained by subtracting the autocorrelation of noise from that of corrupted heart sound. In the noise cancellation unit, if the energy of the current frame exceeds a reference threshold level, the heart is generating sound and the autocorrelation of coefficients representing noise is not updated. However, if the energy of the current frame is below the reference threshold level, the effect of noise on the correlation coefficients is subtracted off in the spectral domain. The result is half-wave rectified with proper threshold setting and then converted to the desired autocorrelation coefficients. The output of the autocorrelator and the noise canceller are presented to one or more parameterization units, including an LPC parameter unit, an FFT parameter unit, an auditory model parameter unit, a fractal parameter unit, or a wavelet parameter unit, among others. The LPC parameter is then converted into cepstral coefficients. The cepstral coefficients are the coefficients of the Fourier transform representation of the log magnitude spectrum. A filter bank spectral analysis, which uses the short-time Fourier transformation (STFT) may also be used alone or in conjunction with other parameter blocks. FFT is well known in the art of digital signal processing. Such a transform converts a time domain signal, measured as amplitude over time, into a frequency domain spectrum, which expresses the frequency content of the time domain signal as a number of different frequency bands. The FFT thus produces a vector of values corresponding to the energy amplitude in each of the frequency bands. The FFT converts the energy amplitude values into a logarithmic value which reduces subsequent computation since the logarithmic values are more simple to perform calculations on than the longer linear energy amplitude values produced by the FFT, while representing the same dynamic range. Ways for improving logarithmic conversions are well known in the art, one of the simplest being use of a look-up table. In addition, the FFT modifies its output to simplify computations based on the amplitude of a given frame. This modification is made by deriving an average value of the logarithms of the amplitudes for all bands. This average value is then subtracted from each of a predetermined group of logarithms, representative of a predetermined group of frequencies. The predetermined group consists of the logarithmic values, representing each of the frequency bands. Thus, utterances are converted from acoustic data to a sequence of vectors of k dimensions, each sequence of vectors identified as an acoustic frame, each frame represents a portion of the utterance. Alternatively, auditory modeling parameter unit can be used alone or in conjunction with others to improve the parameterization of heart sound signals in noisy and reverberant environments. In this approach, the filtering section may be represented by a plurality of filters equally spaced on a log-frequency scale from 0 Hz to about 3000 Hz and having a prescribed response corresponding to the cochlea. The nerve fiber firing mechanism is simulated by a multilevel crossing detector at the output of each cochlear filter. The ensemble of the multilevel crossing intervals corresponding to the firing activity at the auditory nerve fiber-array. The interval between each successive pair of same direction, either positive or negative going, crossings of each predetermined sound intensity level is determined and a count of the inverse of these interspike intervals of the multilevel detectors for each spectral portion is stored as a function of frequency. The resulting histogram of the ensemble of inverse interspike intervals forms a spectral pattern that is representative of the spectral distribution of the auditory neural response to the input sound and is relatively insensitive to noise. The use of a plurality of logarithmically related sound intensity levels accounts for the intensity of the input signal in a particular frequency range. Thus, a signal of a particular frequency having high intensity peaks results in a much larger count for that frequency than a low intensity signal of the same frequency. The multiple level histograms of the type described herein readily indicate the intensity levels of the nerve firing spectral distribution and cancel noise effects in the individual intensity level histograms. Alternatively, the fractal parameter block can further be used alone or in conjunction with others to represent spectral information. Fractals have the property of self-similarity as the spatial scale is changed over many orders of magnitude. A fractal function includes both the basic form inherent in a shape and the statistical or random properties of the replacement of that shape in space. As is known in the art, a fractal generator employs mathematical operations known as local affine transformations. These transformations are employed in the process of encoding digital data representing spectral data. The encoded output constitutes a "fractal transform" of the spectral data and consists of coefficients of the affine transformations. Different fractal transforms correspond to different images or sounds.

Alternatively, a wavelet parameterization block can be used alone or in conjunction with others to generate the parameters. Like the FFT, the discrete wavelet transform (DWT) can be viewed as a rotation in function space, from the input space, or time domain, to a different domain. The DWT consists of applying a wavelet coefficient matrix hierarchically, first to the full data vector of length N, then to a smooth vector of length N/2, then to the smooth-smooth vector of length N/4, and so on. Most of the usefulness of wavelets rests on the fact that wavelet transforms can usefully be severely truncated, or turned into sparse expansions. In the DWT parameterization block, the wavelet transform of the heart sound signal is performed. The wavelet coefficients are allocated in a non-uniform, optimized manner. In general, large wavelet coefficients are quantized accurately, while small coefficients are quantized coarsely or even truncated completely to achieve the parameterization. Due to the sensitivity of the low-order cepstral coefficients to the overall spectral slope and the sensitivity of the high-order cepstral coefficients to noise variations, the parameters generated may be weighted by a parameter weighing block, which is a tapered window, so as to minimize these sensitivities. Next, a temporal derivator measures the dynamic changes in the spectra. Power features are also generated to enable the system to distinguish heart sound from silence.

After the feature extraction has been performed, the heart sound parameters are next assembled into a multidimensional vector and a large collection of such feature signal vectors can be used to generate a much smaller set of vector quantized (VQ) feature signals by a vector quantizer that cover the range of the larger collection. In addition to reducing the storage space, the VQ representation simplifies the computation for determining the similarity of spectral analysis vectors and reduces the similarity computation to a look-up table of similarities between pairs of codebook vectors. To reduce the quantization error and to increase the dynamic range and the precision of the vector quantizer, the preferred embodiment partitions the feature parameters into separate codebooks, preferably three. In the preferred embodiment, the first, second and third codebooks correspond to the cepstral coefficients, the differenced cepstral coefficients, and the differenced power coefficients.

With conventional vector quantization, an input vector is represented by the codeword closest to the input vector in terms of distortion. In conventional set theory, an object either belongs to or does not belong to a set. This is in contrast to fuzzy sets where the membership of an object to a set is not so clearly defined so that the object can be a part member of a set. Data are assigned to fuzzy sets based upon the degree of membership therein, which ranges from 0 (no membership) to 1.0 (full membership). A fuzzy set theory uses membership functions to determine the fuzzy set or sets to which a particular data value belongs and its degree of membership therein.

To handle the variance of heart sound patterns of individuals over time and to perform speaker adaptation in an automatic, self-organizing manner, an adaptive clustering technique called hierarchical spectral clustering is used. Such speaker changes can result from temporary or permanent changes in vocal tract characteristics or from environmental effects. Thus, the codebook performance is improved by collecting heart sound patterns over a long period of time to account for natural variations in speaker behavior. In one embodiment, data from the vector quantizer is presented to one or more recognition models, including an HMM model, a dynamic time warping model, a neural network, a fuzzy logic, or a template matcher, among others. These models may be used singly or in combination.

In dynamic processing, at the time of recognition, dynamic programming slides, or expands and contracts, an operating region, or window, relative to the frames of heart sound so as to align those frames with the node models of each S1-S4 pattern to find a relatively optimal time alignment between those frames and those nodes. The dynamic processing in effect calculates the probability that a given sequence of frames matches a given word model as a function of how well each such frame matches the node model with which it has been time-aligned. The word model which has the highest probability score is selected as corresponding to the heart sound.

Dynamic programming obtains a relatively optimal time alignment between the heart sound to be recognized and the nodes of each word model, which compensates for the unavoidable differences in speaking rates which occur in different utterances of the same word. In addition, since dynamic programming scores words as a function of the fit between word models and the heart sound over many frames, it usually gives the correct word the best score, even if the word has been slightly misspoken or obscured by background sound. This is important, because humans often mispronounce words either by deleting or mispronouncing proper sounds, or by inserting sounds which do not belong.

In dynamic time warping (DTW), the input heart sound A, defined as the sampled time values 1) . . . a(n), and the vocabulary candidate B, defined as the sampled time values B=b(1) . . . b(n), are matched up to minimize the discrepancy in each matched pair of samples. Computing the warping function can be viewed as the process of finding the minimum cost path from the beginning to the end of the words, where the cost is a function of the discrepancy between the corresponding points of the two words to be compared. Dynamic programming considers all possible points within the permitted domain for each value of i. Because the best path from the current point to the next point is independent of what happens beyond that point. Thus, the total cost of [i(k), j(k)] is the cost of the point itself plus the cost of the minimum path to it. Preferably, the values of the predecessors can be kept in an M×N array, and the accumulated cost kept in a 2.times.N array to contain the accumulated costs of the immediately preceding column and the current column. However, this method requires significant computing resources. For the heart sound recognizer to find the optimal time alignment between a sequence of frames and a sequence of node models, it must compare most frames against a plurality of node models. One method of reducing the amount of computation required for dynamic programming is to use pruning. Pruning terminates the dynamic programming of a given portion of heart sound against a given word model if the partial probability score for that comparison drops below a given threshold. This greatly reduces computation, since the dynamic programming of a given portion of heart sound against most words produces poor dynamic programming scores rather quickly, enabling most words to be pruned after only a small percent of their comparison has been performed. To reduce the computations involved, one embodiment limits the search to that within a legal path of the warping.

A Hidden Markov model can be used in one embodiment to evaluate the probability of occurrence of a sequence of observations O(1), O(2), . . . O(t), . . . , O(T), where each observation O(t) may be either a discrete symbol under the VQ approach or a continuous vector. The sequence of observations may be modeled as a probabilistic function of an underlying Markov chain having state transitions that are not directly observable. The transitions between states are represented by a transition matrix A=[a(i,j)]. Each a(i,j) term of the transition matrix is the probability of making a transition to state j given that the model is in state i. The output symbol probability of the model is represented by a set of functions B=[b(j)(O(t)], where the b(j)(O(t) term of the output symbol matrix is the probability of outputting observation O(t), given that the model is in state j. The first state is always constrained to be the initial state for the first time frame of the utterance, as only a prescribed set of left-to-right state transitions are possible. A predetermined final state is defined from which transitions to other states cannot occur. Transitions are restricted to reentry of a state or entry to one of the next two states. Such transitions are defined in the model as transition probabilities. For example, a heart sound pattern currently having a frame of feature signals in state 2 has a probability of reentering state 2 of a(2,2), a probability a(2,3) of entering state 3 and a probability of a(2,4)=1-a(2, 1)-a(2,2) of entering state 4. The probability a(2, 1) of entering state 1 or the probability a(2,5) of entering state 5 is zero and the sum of the probabilities a(2,1) through a(2,5) is one. Although the preferred embodiment restricts the flow graphs to the present state or to the next two states, one skilled in the art can build an HMM model without any transition restrictions.

The Markov model is formed for a reference pattern from a plurality of sequences of training patterns and the output symbol probabilities are multivariate Gaussian function probability densities. The heart sound traverses through the feature extractor. During learning, the resulting feature vector series is processed by a parameter estimator, whose output is provided to the hidden Markov model. The hidden Markov model is used to derive a set of reference pattern templates, each template representative of an identified S1-S4 pattern in a vocabulary set of reference patterns. The Markov model reference templates are next utilized to classify a sequence of observations into one of the reference patterns based on the probability of generating the observations from each Markov model reference pattern template. During recognition, the unknown pattern can then be identified as the reference pattern with the highest probability in the likelihood calculator.

Figure 18A:
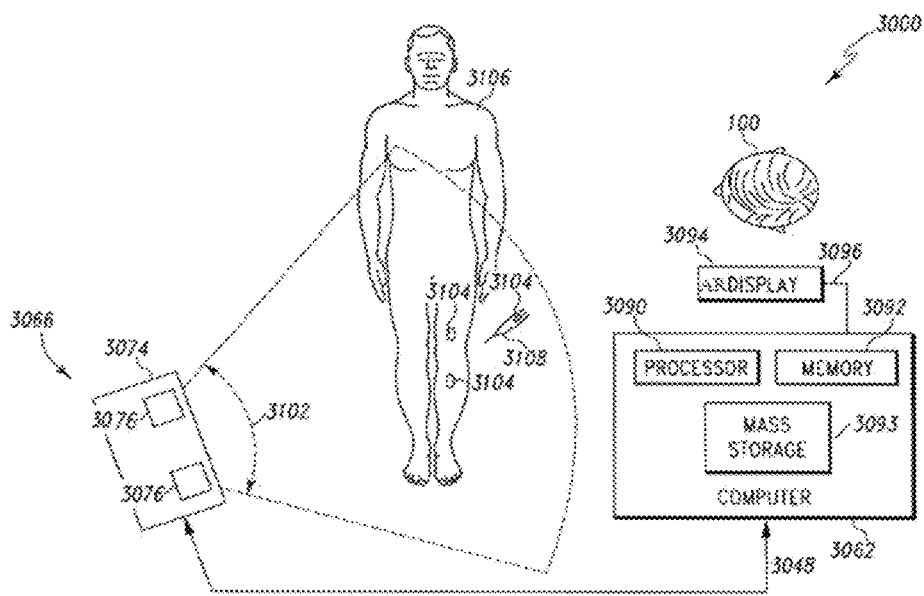

FIG. 18A shows an exemplary AR surgical system 3000. The system may include a processor 3090, a memory device 3092, and mass storage device 3093. The computing device is communicatively coupled with a display device 3094. The AR display device 3094 may be a body mounted display such as a heads-up display or a glass mounted in an AR system such as that of FIG. 1, or an additional display device may be positioned away from the computing device. For example, the display device 3094 may be positioned upon the ceiling or wall of the operating room wherein the orthopaedic surgical procedure is to be performed. Additionally or alternatively, the display device 3094 may include a virtual display such as a holographic display and/or other types of displays. The computing device may be communicatively coupled to one or more camera units. The system 3000 may also include sensors or reference arrays 3104 which may be coupled to relevant bones of a patient 3106 and/or with orthopaedic surgical tools 3108. For example, a tibial array can be used that includes a reference array and bone clamp. The bone clamp may be coupled with a tibia bone of the patient using a Schantz pin, but other types of bone clamps may be used. The reference array may be coupled with the bone clamp via an extension arm. The reference array may include a frame and three reflective elements. The reflective elements in one embodiment are spherical, but may have other geometric shapes. Additionally, in other embodiments sensor arrays having more than three reflective elements may be used. The reflective elements may be positioned in a predefined configuration that enables the computing device to determine the identity of the tibial array based on the configuration. That is, when the tibial array is positioned in a field of view of the camera head, the computing device may determine the identity of the tibial array based on the images received from the camera head. Additionally, based on the relative position of the reflective elements, the computing device may determine the location and orientation of the tibial array and, accordingly, the tibia to which the array is coupled.

Reference arrays may also be coupled to other surgical tools. For example, a registration tool may be used to register points of a bone. The registration tool may include a sensor array having reflective elements coupled with a handle of the tool. The registration tool may also include a pointer end that is used to register points of a bone. The reflective elements may be positioned in a configuration that enables the computing device to determine the identity of the registration tool and its relative location (i.e., the location of the pointer end). Additionally, reference arrays may be used on other surgical tools such as a tibial resection jig. The jig may include a resection guide portion that is coupled with a tibia bone at a location of the bone that is to be resected. The jig may include a reference array that is coupled with the portion via a frame. The reference array 146 may include three reflective elements 148 that may be positioned in a configuration that enables the computing device to determine the identity of the jig and its relative location (e.g., with respect to the tibia bone).

During the performance of the orthopaedic surgical procedure, a custom surgical plan may include one or more instructions that program or otherwise configure the HUD to display images of the individual surgical procedure steps which form the orthopaedic surgical procedure being performed. The images may be graphically rendered images or graphically enhanced photographic images. For example, the images may include three dimensional rendered images of the relevant anatomical portions of a patient. The surgeon may interact with the computing device to display the images of the various surgical steps in sequential order. In addition, the surgeon may interact with the computing device to view previously displayed images of surgical steps, selectively view images, instruct the computing device to render the anatomical result of a proposed surgical step or procedure, or perform other surgical related functions. For example, the surgeon may view rendered images of the resulting bone structure of different bone resection procedures. In this way, the custom surgical plan may configure the system 3000 to provide a surgical "walk-through" customized to the patient 106 that the surgeon may follow while performing the surgical procedure.

In one embodiment, the custom surgical plan may include an ordered selection of instructional images that depict individual surgical steps that make up at least a portion of the orthopaedic surgical procedure to be performed. The instructional images may include images of surgical tools and associated text information, graphically rendered images of surgical tools and relevant patient anatomy, and/or other images and/or text information that assist the surgeon during the surgical procedure. The instructional images may be stored in an electronic library, which may be embodied as, for example, a database, a file folder or storage location containing separate instructional images and an associated look-up table, hard-coded information. The surgical plan may include among other things an ordered selection of instructional images that are displayed to the surgeon via the display device 3094 such that the instructional images provide a surgical "walk-through" of the procedure or portion thereof. The surgical plan may also include a number of surgical sub-step images, some of which may or may not be displayed to and performed by the surgeon based on selections chosen by the surgeon during the performance of the orthopaedic surgical procedure.

In some embodiments, the surgeon may also interact with the computing device to control various devices of the system 3000. For example, the surgeon may interact with the system 3000 to control user preferences or settings of the AR display device 3094. Further, the computing device may prompt the surgeon for responses. For example, the computing device 62 may prompt the surgeon to inquire if the surgeon has completed the current surgical step, if the surgeon would like to view other images, and/or other surgical procedure inquiries.

The AR system may be used to generate pre-operative orthopaedic surgical plans, surgical notes created during an orthopaedic surgery, medical images of a patient's bone (and soft tissue) and/or orthopaedic implants coupled thereto, and/or other data. Such data generated via the system 3000 may be stored in the database by, for example, transmitting the data from the system 3000 to the database via the network. Additionally, other medical devices typically found in a hospital or other healthcare facility may be used to generate medical images of a bone (and, in some embodiments, soft tissue) of the patient. Such medical images may also be stored in the database. The medical images may be embodied as any type of medical image providing a visual indication of a relevant bone or bones (and soft tissue if desired) of a patient. For example, the medical images may be embodied as any number of X-ray images, magnetic resonance imaging (MRI) images, computerized tomography (CT) images, or the like. Regardless, such medical images may be stored in the database 28 along with associated data relevant to the particular medical images. Such associated data may include, but is not limited to, the patient's name and other patient identification information, date of the images, surgeon's or doctor's name, the name of the hospital or healthcare facility wherein the medical images were generated, and the like.

In operation, the system can receive a request for surgical plans for a patient, may generate a surgical plan that has been customized for the patient, and may provide the custom surgical plan for the patient to the healthcare facility.

The surgical plan request data may include any data relevant to the surgical plan being requested, any data related to the orthopaedic surgical procedure to be performed, any data related to the patient on which the orthopaedic surgical procedure to be performed, and/or any other data useful for customizing the orthopaedic surgical procedure to the patient. For example, the request data may include, but is not limited to, the type of orthopaedic surgical procedure to be performed, the type of orthopaedic implant to be used, rendered images of the relevant anatomical portions of the patient, digital templates of the orthopaedic implants and/or planned resection lines, pre-operative notes, diagrams, historic patient data, X-rays, medical images, patient medical records, patient identification data, and/or any other data useful for customizing the orthopaedic surgical procedure to the patient.

In creating the surgical plan, the surgical plan system may perform a digital templating procedure on medical images of the surgical plan request to determine an orthopaedic implant to recommend to the surgeon or healthcare facility for use with relevant bone(s) of the patient. To do so, the surgical plan system may be configured to determine relevant aspects of the patient's bone or bony anatomy from the medical images. For example, the surgical plan system may determine one or more mechanical axis of the relevant bones, determine one or more resection planes of the relevant bones, locate particular features of the relevant bones, and/or the like. Based on such determinations, the surgical plan system may select an appropriate orthopaedic implant type and size that also satisfies the implant constraint data of the surgical plan request. The surgical plan system may also be configured to determine recommended range of sizes of the orthopaedic implant. For example, in some embodiments, the surgical plan system may be configured to determine an orthopaedic implant within a range of plus or minus two sizes. For example, the surgical plan system may recommend an orthopaedic implant of a size 5+/−2 sizes (i.e., a range of size 3 to size 7). In creating the surgical plan, the surgical plan system may also retrieve a digital template(s) of the orthopaedic implant. The digital template may be retrieved from, for example, the memory device 48, mass storage device 49 or from any other storage location capable of storing a number of digital templates. The digital template may include one or more two-dimensional and/or three-dimensional electronic renderings of the orthopaedic implant selected for the surgical procedure, or components thereof, that is capable of being superimposed on a medical image of the patient. For example, a digital template may be embodied as a two-dimensional or three-dimensional electronic rendering of an orthopaedic knee implant component that is capable of being superimposed or otherwise incorporated into a medical image of a tibia or femur bone of the patient. As discussed in more detail below, the digital template may be used in conjunction with indicia of the determined aspects or features of the relevant bones such as lines or other indicia of the mechanical axis or resection points/planes of the relevant bones.

Figure 18B:
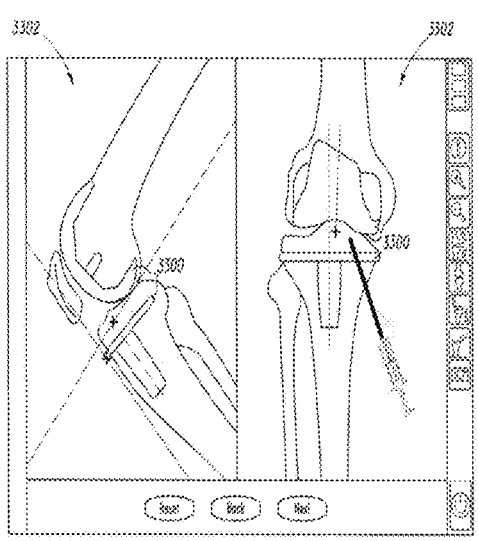
FIG. 18B shows an exemplary template superimposed on bones and tissues using the AR display of FIG. 1.

The surgical plan system may superimpose or otherwise incorporate the digital template into the medical images of the surgical plan request. For example, in one illustrative embodiment, as illustrated in FIG. 18B, a digital template 3300 of an orthopaedic implant is superimposed on a medical image 3302 of a bone of the patient. As discussed above, although the illustrative digital template 3300 is illustrated as a two-dimensional template, in other embodiments, the digital template may include any number of two-dimensional and/or three-dimensional electronic renderings of the orthopaedic implant.

The surgical plan system may be configured to use any suitable algorithm and data of the surgical plan request to determine a recommended location and orientation of the orthopaedic implant, as represented by the digital template, with respect to the patient's bone. For example, if implant constraint data provides an estimated amount of resection of the patients' bone, the surgical plan system may be configured to position the digital template in the medical images based on such estimated resection. In addition, any one or more of the aspects of the bone as determined above may be used to determine the proper positioning of the digital template. For example, the determined mechanical axis, resection planes, and/or other determined aspects of the relevant bones may be used to determine the proper positioning of the digital template. In this way, the surgical plan system generates a number of digital template medical images having indicia of the relevant bone's of the patient and indicia of the recommended orthopaedic implant positioned in a location and orientation.

In one embodiment, the implant is hyaluronic acid (HA). The HA is naturally found in the synovial fluid found between bones and acts as a lubricant. Current treatments like Hyalgan require weekly injections for three to five weeks. Pain relief is not experienced until a few weeks into the treatment. Even though the pain relief is not quick, it is longer lasting than other pain treatments like corticosteroids, which are fast acting but provide short relief. Using a "Visual Analogue Scale and Western Ontario McMaster Universities Osteoarthritis Index score", knees treated with the multiply cross-linked HA can benefit from decreased pain and increased movement as long as two years. Procedure for injections includes:

Knee area is cleaned

If area is swollen because of excess fluid in joint, a needle will be used to drain fluid after a local anesthetic is applied With drainage system in place, multiply cross-linked HA is injected into knee joint The same needle may be used for drainage and injections or two different syringes The system can be used for augmenting information to a doctor during implantation of HA into the knee as follows:

obtaining injection location from sensors (such as X-rays, MRI, and CT-Scans);

determining, from the 3D kinematic data, scores characterizing a joint function of the patient, the scores being relative to one or more and comparing the scores to data in a database which characterize a plurality of treatment plans and/or surgery plans to generate the list of one or more joint treatment plans and/or surgery plans which match the scores.

System identifies best injection points and displays the point using augmented reality to guide the doctor to inject HA at the right points on the knee.

In another embodiment, the system looks up surgical plan sequence:
  determines body landmarks or key positions,
  identifies or highlights on the HUD each surgical path to surgically operate and provides instructions on surgical techniques,
  optionally overlaying images of the anatomy to guide the doctor
  wait until each surgical technique and then show next technique until done
  accessing the target component to replace or repair and show instructions to repair or replace,
  sequentially showing instructions to seal body portions previously opened or removed.

While knee implant is discussed above, other implants can be used. For example, a surgeon holds a wireless wand-like device near a place where he plans to make an incision, the device sends data about that spot to a computer where it is combined with information from a CT scan of the patient's brain taken previously. This information is compiled into a single X-ray-like image that the surgeon can see in real time with VR/AR displays, allowing her to examine the blood vessels and nerves that surround the place of the incision so that the surgical tool is as precise as possible. Once the incision is made, the AR/VR display can help the surgeon damage as little as possible on its way to the desired nerve, where the surgeon can implant the neuromodulator device.

Figure 18C:
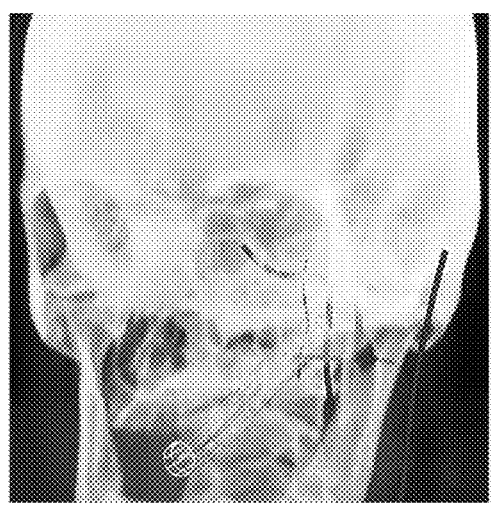
FIG. 18C shows an exemplary AR view of a placement of a neuromodulator to mask pain.

FIG. 18C shows an exemplary AR view of a placement of a neuromodulator to mask pain by actively stimulating nerves to produce a natural biological response or by applying targeted pharmaceutical agents in tiny doses directly to site of action. These precisely placed leads connect via an extension cable to a pulse generator and power source, which generates the necessary electrical stimulation. A low-voltage electrical current passes from the generator to the nerve, and can either inhibit pain signals or stimulate neural impulses where they were previously absent to the brain, the spinal cord or peripheral nerves. In the case of pharmacological agents delivered through implanted pumps, the drug can be administered in smaller doses because it does not have to be metabolized and pass through the body before reaching the target area. Smaller doses—in the range of 1/300 of an oral dose—can mean fewer side effects, increased patient comfort and improved quality of life.

While there have been shown what are presently considered to be preferred embodiments of the present invention, it will be apparent to those skilled in the art that various changes and modifications can be made herein without departing from the scope and spirit of the invention.

What is claimed is:

1. An augmented reality method, comprising:
  selecting an image of an object to be installed and generating a 3D model of the object from dimensions associated with the object;
  capturing a view of an environment using a mobile camera, generating a 3D model of the environment using the camera, and selecting a place to insert the 3D model of the object in the 3D model of the environment;
  motion-tracking visual features of the environment using concurrent odometry and mapping (COM) including feature points and planes to estimate a pose of the camera relative to the environment further including performing motion tracking and understanding an environment with points or planes using accelerometer sensor and estimating light or color in the environment using one video camera without a depth sensor in a mobile phone; determining a target volume or space; capturing images from a plurality of angles of the environment; acquiring sensor data from sensors and optimizing features extracted from each image and sensor data, where a feature conveys data unique to the image at a specific pixel location;
  understanding the environment using feature points and planes including plane boundary, in combination with accelerometer and gyroscope data, to track movements in space;
  determining intensity of light including lighting of the environment, brightness, foreground lighting, background lighting;
  overlaying the 3D model with the view of the environment wherein the 3D model is rendered with the environment and lighting of the environment to form an augmented reality view; and
  receiving user interaction with the displayed 3D model to update the 3D model of the object.

2. The method of claim 1 wherein the environment is a location, farm, building, plant, factory, refinery, city, a vehicle, a car, a plane, a ship, an entity or a physical asset, comprising applying a color for the 3D model.

3. The method of claim 1 comprising downloading either a file with 3D object data or downloading a plurality of images of the object for 3D reconstruction from a shopping web site.

4. The method of claim 1 wherein display of the augmented reality view and user interaction therewith are implemented by an augmented reality application; and the 3D database is one of external to or embedded in the augmented reality application.

5. The method of claim 4 further comprising the step of federating the 3D modeling system with the augmented reality application.

6. The method of claim 1 wherein the step of enabling user interaction with the displayed 3D model view is implemented by the 3D modeling system that was originally used to generate the 3D model of the environment or used to store said 3D model in the 3D database.

7. The method of claim 1, comprising in response to user interaction with the displayed 3D model view, the 3D modeling system updating the corresponding 3D model of the object and the 3D model of the environment in the 3D database.

8. The method of claim 1 wherein displaying of the 3D model view of the one environment object overlaying the augmented reality view is aligned in size, dimensions and/or orientation.

9. The method of claim 1, comprising:
  determining body landmarks or key positions;
  identifying a surgical path to operate and providing instruction on surgical technique;
  overlaying images of the anatomy to guide a user;
  accessing a target to replace or repair and show instruction to repair or replace.

10. The method of claim 1, comprising:
  identifying buildings and building structures positioned thereon; and
  retrieving a building repair sequence.

11. The method of claim 1, comprising:
  determining type and location of a building structure, and highlighting on the augmented reality view each building structure to be opened or removed and provides instructions on opening or removal techniques.

12. The method of claim 11, comprising:
iteratively providing instructions to allow each structure to be opened or removed and then show next structure;
accessing a target structure to replace or repair and showing instructions to repair or replace; and
showing instructions in sequence to put back structures previously opened or removed.

13. The method of claim 1, comprising rendering the 3D model as a perspective view relative to the environment, and sharing a waveguide or an image field where multiple viewers optically perceive a digital or virtual object from different viewing perspectives that match each viewer's respective locations relative to the waveguide.

14. The method of claim 1, comprising rendering video in the augmented view one or more maintenance or repair techniques.

15. The method of claim 1, comprising:
storing environment data in a map that can be re-used with metadata including notes, instructions, or points of interest.

16. The method of claim 1, comprising:
displaying a 3D model view of the object overlaying on the augmented reality view of the machine in a mashed-up and aligned manner such that the 3D model view is displayed contemporaneously and contiguously to the augmented reality view; and
identifying with the camera in the augmented reality view each object to be opened or removed and providing instructions on how to open or move the object in order to access a targeted object.

17. The method of claim 1, comprising automatically identifying the machine and retrieving parts and components in the machine with the camera.

18. The method of claim 1, comprising after each component is opened or removed, detecting with the camera the next object to be opened or removed to reach the targeted object to be replaced or repaired;
showing instructions to repair or replace the object; and
showing instructions in the augmented reality view to put back objects previously opened or removed.

19. A computer aided design (3D) modeling method comprising:
generating an augmented reality view of an environment, the environment having various objects displayed in the augmented reality view;
in response to user interaction with one of the environment objects as displayed in the augmented reality view, searching a 3D database for a corresponding 3D model of the one object, generating a 3D model of the environment from a camera to insert the 3D object from either obtaining the 3D model of the one object or generating the 3D model of the one object from a plurality of images;
motion-tracking with visual features of an environment including points and planes, in combination with accelerometer and gyroscope data, to track movements in space and understanding the environment; and determining intensity of light including lighting of the environment, brightness, foreground lighting, background lighting, further including performing motion tracking and understanding an environment with points or planes using accelerometer sensor and estimating light or color in the environment using one video camera without a depth sensor in a mobile phone: determining a tart et volume or space: capturing images from a plurality of angles of the environment; acquiring sensor data from sensors and optimizing features extracted from each image and sensor data, where a feature conveys data unique to the image at a specific pixel location;
determining intensity of light including lighting of the environment, brightness, foreground lighting, background lighting;
displaying a 3D model view of the one object overlaying on the augmented reality view of the environment and the one object; and
enabling user interaction with the displayed 3D model view to update the 3D model of the environment.

20. The method of claim 19, comprising:
motion-tracking with visual features of an environment, in combination with accelerometer and gyroscope data, to track movements in space;
storing environment data in a map that can be re-used with metadata including notes, instructions, or points of interest; and
detecting distances, sizes, and surfaces in the environment for depth perception.

* * * * *